(12) United States Patent
Kobayashi et al.

(10) Patent No.: US 7,993,643 B2
(45) Date of Patent: Aug. 9, 2011

(54) USES OF HUMAN MONOCLONAL ANTIBODIES AGAINST OXIDIZED LDL RECEPTOR

(75) Inventors: Yuko Kobayashi, Kanagawa (JP); Hiroyuki Tsuji, Kanagawa (JP); Masafumi Kamada, Kanagawa (JP); Tatsuya Sawamura, Kyoto (JP)

(73) Assignee: Amgen Fremont, Inc., Fremont, CA (US)

( * ) Notice: Subject to any disclaimer, the term of this patent is extended or adjusted under 35 U.S.C. 154(b) by 433 days.

(21) Appl. No.: 11/740,857

(22) Filed: Apr. 26, 2007

(65) Prior Publication Data

US 2008/0241134 A1 Oct. 2, 2008

Related U.S. Application Data

(62) Division of application No. 10/220,511, filed as application No. PCT/JP01/01636 on Mar. 2, 2001, now abandoned.

(30) Foreign Application Priority Data

Mar. 2, 2000 (JP) ................................ 2000-057745
Oct. 31, 2000 (JP) ................................ 2000-333116

(51) Int. Cl.
*A61K 39/395* (2006.01)
*C07K 16/28* (2006.01)
(52) U.S. Cl. ................................ 424/143.1; 530/388.15
(58) Field of Classification Search .................... None
See application file for complete search history.

(56) References Cited

U.S. PATENT DOCUMENTS

| 5,620,687 | A |   | 4/1997 | Hart et al. |
| 5,945,308 | A | * | 8/1999 | Tang et al. ................. 435/69.1 |
| 5,962,260 | A |   | 10/1999 | Sawamura et al. |
| 2001/0053539 | A1 |   | 12/2001 | Lauffer et al. |

FOREIGN PATENT DOCUMENTS

| CA | 2045869 |   | 12/1991 |
| CA | 2315280 |   | 7/1999 |
| EP | 0464533 |   | 1/1992 |
| EP | 626390 | A1 * | 11/1994 |
| EP | 0795605 |   | 9/1997 |
| JP | 9-121859 |   | 5/1997 |
| JP | 11-127855 |   | 5/1999 |
| JP | 11-239491 |   | 9/1999 |
| JP | 2000-109435 |   | 4/2000 |
| WO | WO 96/17058 |   | 6/1996 |
| WO | WO 99/32520 |   | 7/1999 |

OTHER PUBLICATIONS

Janeway et al. Immunobiology: the immune system in health and disease, Third Ed., New York: Garland Pub, 1997, pp. 2:19-2:20.*
Bianchi, Camillo, "Thrombocytopenia provoked by carrageenan in rabbits and the inhibitory effect of lysozyme" *Agents and Actions* (1982) 12(5): 657-661.
Campa, et al., "Polyinosinic acid induces TNF and NO production as well as NF-κB and AP-1 transcriptional activation in the monocyte-macrophage cell line RAW 264.7" *Inflamm. Res.* (2005) 54: 328-337.
Davidson, et al., "Haematological Changes Following Systemic Injection of Purified Carrageenans (Kappa, Lambda and Iota)" *Br. J. exp. Path.* (1981) 62: 529-539.
Fowler, et al, "Histological and Ultrastructural Changes Following Carrageenan Injection in the Mouse" *J. Pathology* (1980) 132: 63-79.
Gervasi, et al., "A New Low Molecular Weight Heparan Sulphate Antagonizes κ-Carrageenan-Induced Thrombosis in Rats" *Pharmacological Research* (1991) 24: 59-63.
Ishiguro, et al., "Syndecan-4 Deficiency Increases Susceptibility to κ-Carrageenan-Induced Renal Damage" *Laboratory Investigation* (2001) 81(4): 509-516.
Mehta, J.L. and D.Y. Li, "Identification and Autoregulation of Receptor for OX-LDL in Cultured Human Coronary Artery Endothelial Cells" *Biochemical and Biophysical Research Communications* (1998) 248: 511-514.
Popper, et al., "Reduction of carrageenan-bradykinin- and histamine-induced acute inflammation by experimental eosinophilia in rats" *Immunology* (1982) 46: 589-594.
Aoyama, et al., "Structure and chromosomal assignment of the human lectin-like oxidized low-density-lipoprotein receptor-1 (LOX-1) gene" *Biochem J.* 339(Pt. 1): 177-184 (1999).
Green, et al., "Antigen-specific human monoclonal antibodies from mice engineered with human Ig heavy and light chain YACs" *Nat. Genet.* 7(1):13-21 (1994).
Huang, et al., "Oxidized LDL-containing immune complexes induce Fc gamma receptor I-mediated mitogen-activated protein kinase activation in THP-1 macrophages" *Arterioscler Thromb. Vasc. Biol.* 19(7):1600-1607 (1999).
Jakobovits, "Production of fully human antibodies by transgenic mice" *Curr. Opin. Biotechnol.* 6(5):561-566 (1995).
Janeway, et al., *Immunobiology: the immune system in health and disease*, Third Ed., New York: Garland Pub. 1997.
Kakutani, et al., "A platelet-endothelium interaction mediated by lectin-like oxidized low-density lipoprotein receptor-1" *Proc. Natl. Acad. Sci. USA* 97(1):360-364 (2000).
Kataoka, et al., "Expression of Lectinlike Oxidized Low-Density Lipoprotein Receptor-1 in Human Atherosclerotic Lesions" *Circulation* 99(24):3110-3117 (1999).
Li Dy, et al., "Upregulation of Endothelial Receptor for Oxidized Low-Density Lipoprotein (LOX-1) in Cultured Human Coronary Artery Endothelial Cells by Angiotensin II Type 1 Receptor Activation" *Circ. Res.* 84(9):1043-1049 (1999).
Lipsky, et al., "The carboxyl-terminal cytoplasmic domain of CD36 is required for oxidized low-density lipoprotein modulation of NF-kappaB activity by tumor necrosis factor-alpha" *Recept. Signal Transduct.* 7(1):1-11 (1997).

(Continued)

*Primary Examiner* — Daniel E Kolker
*Assistant Examiner* — Gregory S Emch
(74) *Attorney, Agent, or Firm* — Knobbe, Martens, Olson & Bear LLP

(57) ABSTRACT

Various human monoclonal antibodies that bind to human LOX-1 and inhibit the binding of in-vivo LOX-1 ligands to LOX-1, and the LOX-1-mediated incorporation of the ligands into cells, were obtained by immunizing human antibody-producing transgenic mice (created by genetic engineering) with soluble human oxidized LDL receptor (LOX-1). Furthermore, the human monoclonal antibodies were found to be effective in preventing and treating a variety of diseases.

28 Claims, 15 Drawing Sheets

OTHER PUBLICATIONS

Morawietz, et al., "Angiotensin II Induces LOX-1, the Human Endothelial Receptor for Oxidized Low-Density Lipoprotein" *Circulation* 100(9):899-902 (1999).

Morganelli, et al., "Evidence that human Fc gamma receptor IIA (CD32) subtypes are not receptors for oxidized LDL" *Arterioscler. Thromb. Vasc. Biol.* 17(11):3248-3254 (1997).

Moriwaki, et al., "Expression of lectin-like oxidized low density lipoprotein receptor-1 in human and murine macrophages: upregulated expression by TNF-α" *FEBS Lett.* 440(1-2):29-32 (1998).

Murase, et al., "Fluid Shear Stress Transcriptionally Induces Lectin-like Oxidized LDL Receptor-1 in Vascular Endothelial Cells" *Circ. Res.* 83(3):328-333 (1998).

Nagase, et al., "Enhanced Expression of Endothelial Oxidized Low-Density Lipoprotein Receptor (LOX-1) in Hypertensive Rats" *Biochem Biophys Res. Commun.* 237(3):496-498 (1997).

Nagase, et al., "Genomic Organization and Regulation of Expression of the Lectin-like Oxidized Low-density Lipoprotein Receptor (LOX-1) Gene" *J. Biol. Chem.* 273(50):33702-33707 (1998).

Nagase, et al., "Unique repetitive sequence and unexpected regulation of expression of rat endothelial receptor for oxidized low-density lipoprotein (LOX-1)" *Biochem J.*, 330(Pt. 3):1417-1422 (1998).

Oka, et al., "Lectin-like oxidized low-density lipoprotein receptor 1 mediates phagocytosis of aged/apoptotic cells in endothelial cells" *Proc. Natl. Acad. Sci.* USA 95(16):9535-9540 (1998).

Sawamura, et al., "An endothelial receptor for oxidized low-density lipoprotein", *Nature*, 386(6620):73-77 (1997).

Woo, et al., Homologous human macrophage hybridomas that produce a novel cytotoxic factor in their culture supernatants *Microbiol. Immunol.* 32(1):97-114 (1988).

Yamanaka, et al., "The Human Gene Encoding the Lectin-Type Oxidized LDL Receptor (OLR1) is a Novel Member of the Natural Killer Gene Complex with a Unique Expression Profile" *Genomics* 54(2):191-199 (1998).

International Search Report, dated Jun. 12, 2007, issued in International Application No. PCT/JP01/01636.

* cited by examiner

| JMAb | Clone | Isotype | ELISA | | | | Uptake Inhibition | | | | | Kd(M) (Dissociation constant) | |
|---|---|---|---|---|---|---|---|---|---|---|---|---|---|
| | | | Human | Bovine | Pig | Rabbit | Human | Bovine | Pig | Rabbit | HeLa | hLox-Fc | bLox-Fc |
| 90 | LXP105-1-1 | hIgG2,k | O | O | x | O | O | x | | O | O | 2.1x10-8 | no binding |
| 91 | LXP291-A2-1 | hIgG2,k | O | O | O | O | O | O | O | O | O | 1.7x10-8 | 2.4x10-8 |
| 92 | LXP607-5-1 | hIgG2,k | O | O | O | O | O | O | | O | O | 2.4x10-8 | 3.9x10-8 |
| 93 | LXP109-5-1 | hIgG2,k | O | x | x | O | O | | | | O | 2.5x10-8 | |
| 94 | LXP230-1-1 | hIgG2,k | O | x | x | O | O | | | O | O | 2.4x10-8 | |
| 95 | LXP479-1-1 | hIgG2,k | O | x | x | x | O | | | | O | 2.7x10-8 | |
| 96 | LXP544-1-1 | hIgG2,k | O | O | x | x | O | | | | O | 8.3x10-8 | |
| 98 | LXR44-1-1 | hIgG2,k | O | x | x | O | O | O | | O | O | 8.6x10-8 | |
| 99 | LXR89-1-1 | hIgG2,k | O | O | O | O | O | | x | x | O | 6.8x10-8 | |
| 100 | LXp163-2-2 | hIgG4,k | O | x | x | O | O | x | | x | O | 4.4x10-8 | |
| 101 | LXp267-4-1 | hIgG4,k | O | O | O | O | O | △ | O | O | O | | |
| 102 | LXP36-3-1 | hIgG2,k | O | O | x | x | O | | | | O | 7.8x10-9 | |
| 103 | LXP299-2-4 | hIgG2,k | O | x | x | x | O | | | | O | 2.0x10-7 | |
| 104 | LXR147-3-1 | hIgG4,k | O | x | x | O | O | | | O | O | 3.9x10-6 | |
| 105 | LXp114-8-4 | hIgG2,k | O | x | x | x | O | | | | O | 7.5x10-9 | |
| 106 | LXP486-2-2 | hIgG2,k | O | O | x | x | O | | | x | O | 4.8x10-8 | |
| 107 | LXR11-1-1 | hIgG2,k | O | O | x | x | O | | | | O | 1.7x10-8 | |
| 108 | LXR155-1-1 | hIgG2,k | O | x | x | x | O | △ | | | O | 4.3x10-9 | |
| 111 | LXP140-1-1 | hIgG2,k | O | O | O | O | O | x | | O | O | 3.1x10-8 | |
| 112 | LXP464-1-1 | hIgG2,k | O | O | O | O | O | O | | O | O | 2.1x10-8 | |
| 113 | LXR340-8-3 | hIgG2,k | O | x | x | x | O | | | x | O | 1.7x10-8 | |
| 114 | LXS49-1-4 | hIgG2,k | O | O | O | O | O | O | O | O | O | 1.6x10-8 | |
| 115 | LXSS9-1-6 | hIgG2,k | O | O | x | O | O | | | O | O | 7.4x10-9 | |
| 116 | LXS130-1-1 | hIgG2,k | O | O | x | O | O | x | | x | O | 7.0x10-8 | |
| 117 | LXS260-1-1 | hIgG2,k | O | x | x | O | O | x | | O | O | 1.3x10-8 | |
| 118 | LXP262-3-2 | hIgG2,k | O | O | x | O | O | | | O | O | 3.7x10-6 | |
| 119 | LXP313-3-1 | hIgG2,k | O | O | x | O | O | | | x | O | 3.3x10-8 | |
| 121 | LXS279-1-1 | hIgG2,k | O | x | x | O | O | | | x | O | 6.1x10-8 | |
| 122 | LXp165-2-1 | hIgG2,k | O | (△) | x | O | O | | | | O | 2.2x10-8 | |
| 123 | LXp171-11-14 | hIgG4,k | O | x | x | x | O | | | x | O | | |
| 132 | LXS68-12-5 | hIgG2,k | O | O | x | O | O | x | | O | O | 1.1x10-7 | |
| 134 | LXP147-2-1 | hIgG2,k | O | O | x | O | O | | | O | O | 4.6x10-8 | |

FIG. 4

USES OF HUMAN MONOCLONAL ANTIBODIES AGAINST OXIDIZED LDL RECEPTOR

RELATED APPLICATIONS

This application is a divisional of pending U.S. application Ser. No. 10/220,511 filed Dec. 6, 2002, which is a national stage application under 35 USC §371 of International Application No. PCT/JP01/01636 filed Mar. 2, 2001, which claims priority to Japanese Application No. 2000-057745 filed Mar. 2, 2000, which PCT Application also claims priority to Japanese Application No. 2000-333116 filed Oct. 31, 2000. The International Application was not published in English under PCT Article 21(2).

TECHNICAL FIELD

The present invention relates to methods of treating disease using monoclonal antibodies binding to human oxidized LDL receptor (hereinafter, sometimes referred to as "LOX-1") and pharmaceutical compositions comprising a substance inhibiting the interaction between a human monoclonal antibody, or the oxidized LDL receptor, and the ligand thereof.

BACKGROUND ART

The various types of cholesterols (free, long chain fatty acid-type, and ester-type), found in a variety of tissues and in blood, are primarily biosynthesized in the liver. Free cholesterol biosynthesized in the liver binds to very low-density lipoprotein (VLDL), and is metabolized by lipoprotein lipase (LPL) and hepatic triglyceride lipase (HTGL) in blood into low-density lipoprotein (LDL) via intermediate density lipoprotein (IDL). IDL is incorporated into peripheral cells via the LDL receptor and plays an important role in the in-vivo constitution of the cell membrane.

However, LDL is oxidized by cells, such as vascular endothelial cells, various chemical and physical factors, and other factors such as heat, resulting in the generation of modified LDL, which is also referred to as "oxidized LDL", in blood. Since the vascular flow normally contains a sufficient amount of antioxidants, oxidized LDL is hardly generated therein. Even when oxidized LDL is generated, most of it is metabolized in the liver.

On the other hand, oxidized LDL is produced in the vascular endothelium and vascular wall through chemical modifications due to cell-independent actions, such as the action of $Fe^{3+}$, as well as chemical modifications by cells, such as vascular endothelial cells and macrophages. However, unlike that generated in the vascular flow, oxidized LDL generated in the vascular endothelium and vascular wall accumulates within macrophages.

The accumulation of oxidized LDL in macrophages results due to the incorporation of oxidized LDL, generated as described above, into cells via the cell surface scavenger receptor on macrophages, which serves as a receptor for various modified LDLs (oxidized LDL, acetyl LDL, succinyl LDL, and malondialdehyde LDL) (Nature, Vol. 343, p. 531-535, 1990; Nature, Vol. 343, p. 570-572, 1990; Proc. Natl. Acad. Sci. USA, Vol. 87, p. 9133-9137, 1990; Proc. Natl. Acad. Sci. USA, Vol. 87, p. 8810-8814, 1990; Curr. Opin. Lipodol., Vol. 2, p. 295-300, 1991; and J. Clin. Invest., Vol. 90, p. 1450-1457, 1992).

Unlike the LDL receptor, the macrophage scavenger receptor is not down regulated in an intracellular cholesterol-dependent manner. Thus, macrophages migrating into the vascular endothelium or vascular wall take in a large quantity of modified LDL and accumulate a large quantity of cholesterol to become "foamy cells" (See section 4 "Inflammatory Cells: 1. Scavenger Receptor" in "The molecular atherosclerology", pp. 249-258, 1995, Medical Review Co.).

The above-mentioned macrophages, that creep into the vascular endothelium or vascular wall, originally derive from macrophages that migrate from the vascular flow in response to oxidized LDL generation signals generated at various sites, such as in the vascular flow, vascular endothelium, and vascular wall. Specifically, such macrophage accumulation is based on the following characteristics of oxidized LDL; its chemotactic effect on macrophages and monocytes in the vascular flow; the accumulation of monocytes and macrophages on vascular endothelial cells; the induction of the migration of the accumulated monocytes and macrophages into the vascular endothelium and vascular wall; the induction of the differentiation of migrated monocytes into macrophages; and the suppression of the migration of completely differentiated macrophages.

A recently identified oxidized LDL receptor (also referred to as the Ox-LDL Receptor and LOX-1; Nature, Vol. 386, p. 73-77, 1997; Biochemical Study on Lipids, Vol. 39, p. 83-84, 1997; Genomics, Vol. 54, No. 2, p. 191-199, 1998; Biochem. J., Vol. 339, Part 1, p. 177-184, 1999; Biochem. J., Vol. 330, Part 3, p. 1417-1422, 1998) expressed on the surface of vascular endothelial cells has been demonstrated to be deeply involved in such accumulations of monocytes and macrophages on vascular endothelial cells.

Earlier studies demonstrated that the intracellular production of nitrogen monoxide (NO) is inhibited by the oxidized LDL receptor-mediated incorporation of oxidized LDL into vascular endothelial cells from the vascular flow, which results in the expression of cell adhesion molecules on the surface of vascular endothelial cells. This suggests that the expression of cell adhesion molecules results in the entrapment of macrophages and monocytes on vascular endothelial cells, and then the entrapped macrophages and monocytes migrate into the vascular endothelium and vascular wall. Then, the macrophages in the vascular endothelium and vascular wall presumably become "foamy cells", due to the macrophage scavenger receptor-mediated incorporation of oxidized LDL, as described above.

The conversion of macrophages to foamy cells in the vascular wall is a major cause of arteriosclerosis. Thus, the above-mentioned accumulation of monocytes and macrophages in the vascular endothelial cells is believed to trigger the onset of arteriosclerosis.

Intensive research has been made into the biological function of oxidized LDL receptor (LOX-1), which is deeply involved in the accumulation of monocytes and macrophages on vascular endothelial cells, and its involvement in various diseases. Recent studies have reported the following:

(1) The expression level of LOX-1 is markedly higher in arteriosclerotic lesions (Circulation, Vol. 99, No. 24, p. 3110-3117, 1999);

(2) The expression level of LOX-1 is higher in the high blood-pressure rat model (Biochem. Biophys. Res. Commun., Vol. 237, No. 3, p. 496-498, 1997);

(3) Shear stress increases the expression level of LOX-1 (Circ. Res., Vol. 83, No. 3, p. 328-333, 1998);

(4) LOX-1 is expressed in macrophages as well as in vascular endothelial cells and the expression levels are elevated following TNFα stimulation (FEBS Lett., Vol. 440, No. 1-2, p. 29-32, 1998);

(5) The expression level of LOX-1 is elevated by angiotensin II (Circ. Res., Vol 84, No 9, p. 1043-1049, 1999; Circulation, Vol. 100, No. 9, p. 899-902, 1999); and (6) Not only oxidized LDL, but also in-vivo spodogenous cells, such as apoptotic cells (cells programmed to die through apoptosis), senescent erythrocytes, and activated blood platelets, are incorporated into cells via the oxidized LDL receptor (LOX-1) (Proc. Natl. Acad. Sci. USA., Vol. 95, p. 9535-9540, 1998; Proc. Natl. Acad. Sci. USA., Vol. 97, No. 1, p. 360-364, 2000).

Previously reported antibodies against human oxidized LDL receptor (LOX-1) were all derived from non-human mammals only. No report has been published on the preparation of human monoclonal antibodies or on therapeutic approaches for various diseases using such human monoclonal antibodies.

SUMMARY

One embodiment of the invention is a method of inhibiting binding of human oxidized low density lipoprotein to a human oxidized low density lipoprotein receptor (LOX-1). The methods includes contacting the receptor with an isolated human monoclonal antibody, or a binding portion thereof, which binds to LOX-1.

Another embodiment is a method of treating a disease or condition associated with binding of a human oxidized low density lipoprotein receptor (LOX-1) to an in vivo ligand of the receptor. This method includes identifying a patient in need of treatment for said disease or condition; and administering to the patient a pharmaceutical composition comprising a human monoclonal antibody, or a binding portion thereof, which binds to LOX-1.

The vertical axis indicates fluorescence intensity, and the horizontal axis indicates the type of human anti-human LOX-1 monoclonal antibody tested.

Figure 2:
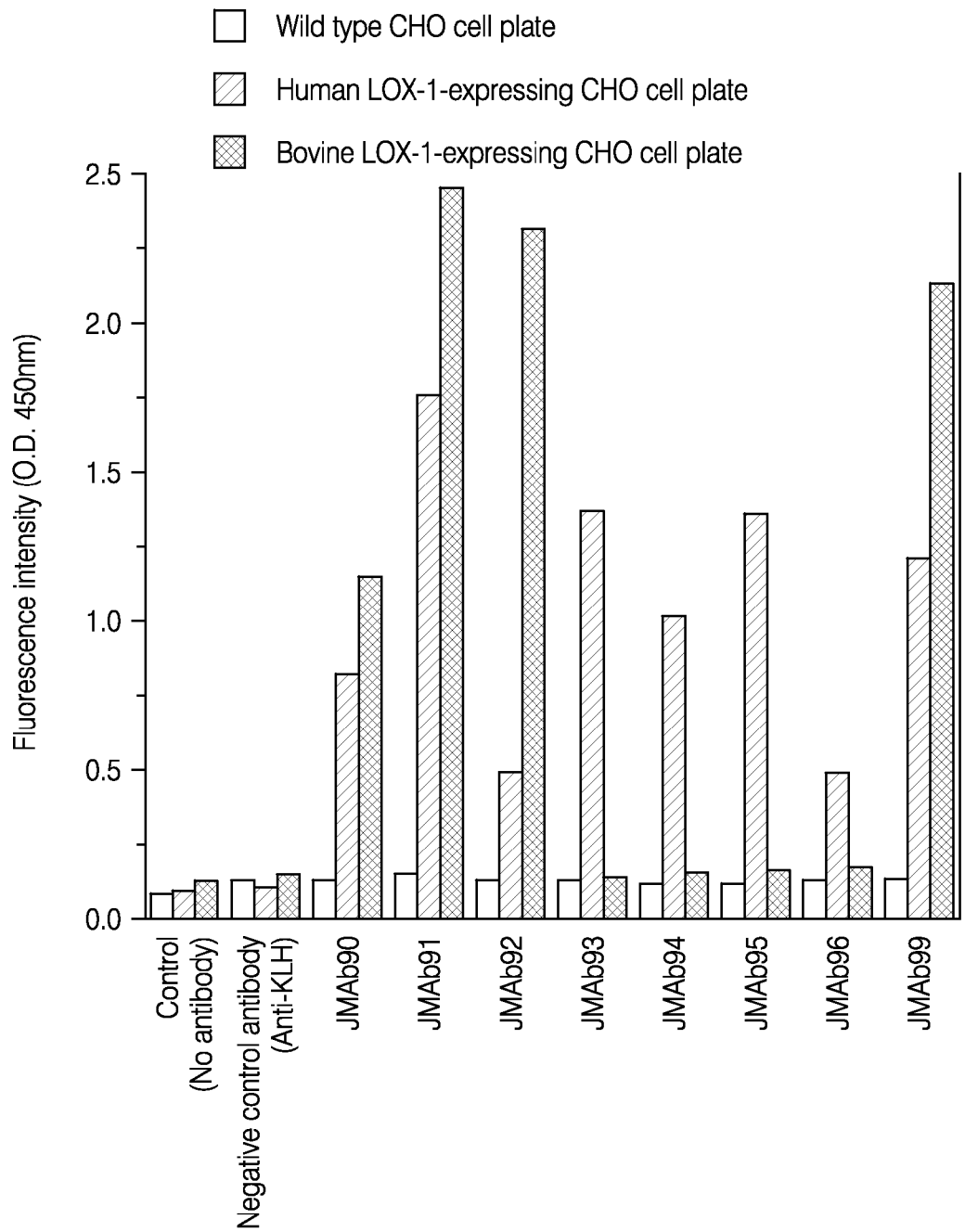

FIG. 2 is a diagram showing the reactivity (binding activity) of human anti-human LOX-1 monoclonal antibodies to human LOX-1, which was analyzed by cell ELISA using human LOX-1-expressing recombinant CHO cells. The vertical axis indicates fluorescence intensity, and the horizontal axis indicates the type of human anti-human LOX-1 monoclonal antibody tested.

Figure 3:
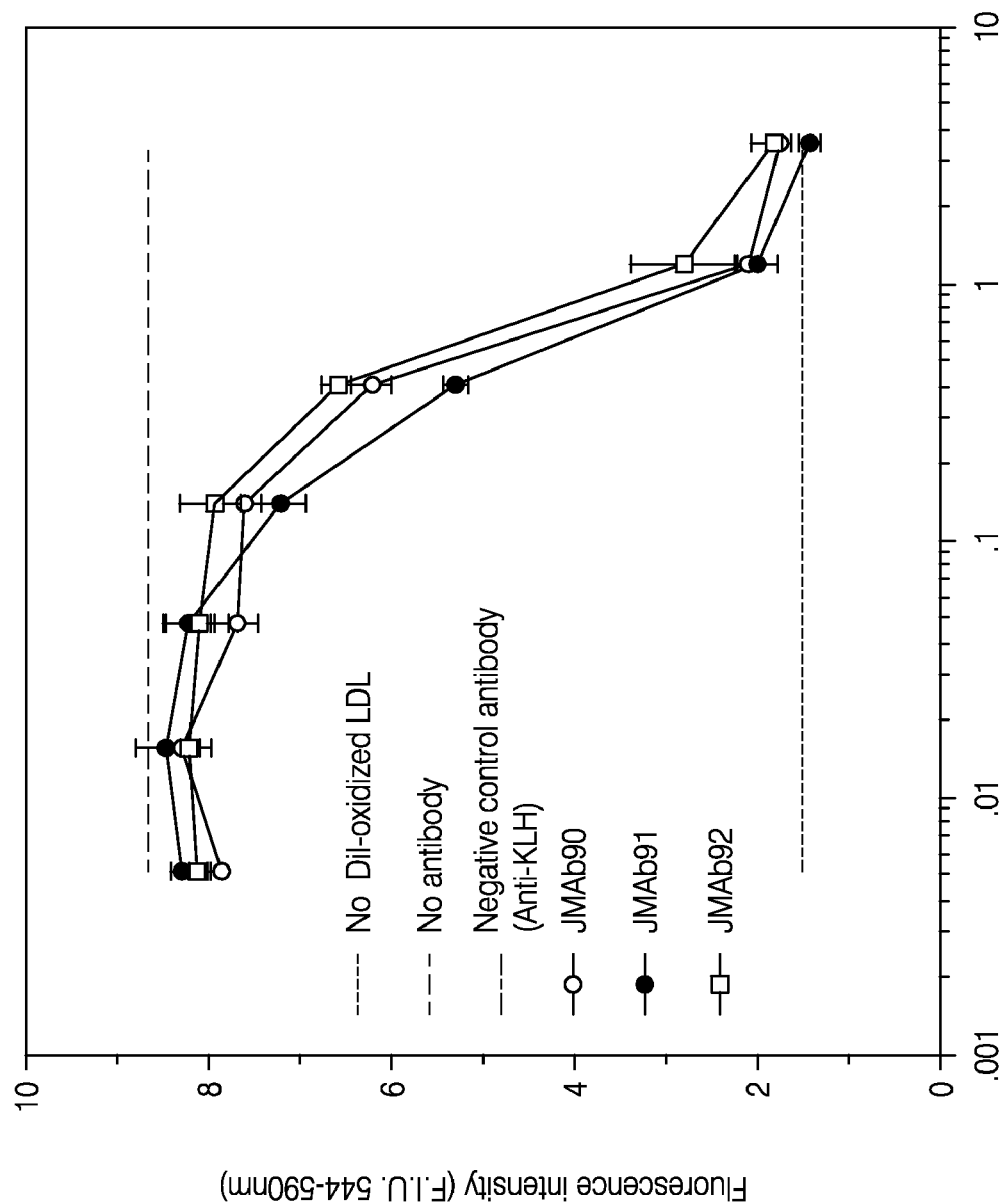

FIG. 3 is a diagram showing the inhibitory activity of the human anti-human LOX-1 monoclonal antibodies on the incorporation of oxidized LDL in the test of oxidized LDL incorporation into recombinant CHO cells expressing human LOX-1. The vertical axis indicates fluorescence intensity as an index of the quantity of oxidized LDL incorporated into cells, and the horizontal axis indicates the concentration of human anti-human LOX-1 monoclonal antibody added.

FIG. 4 is table showing characteristics of various human monoclonal antibodies against anti-human oxidized LDL receptor (LOX-1). The symbols in this table indicate the following:

<ELISA>

Circle: significant antigen-binding activity (reactivity);
Triangle: weak but significant antigen-binding activity (reactivity);
Cross: no significant antigen-binding activity (reactivity);

<Inhibition Test of Oxidized LDL Incorporation>

Circle: significant inhibitory activity on oxidized LDL incorporation;
Triangle: weak but significant inhibitory activity on oxidized LDL incorporation; and
Cross: no significant inhibitory activity on oxidized LDL incorporation.

Figure 5:
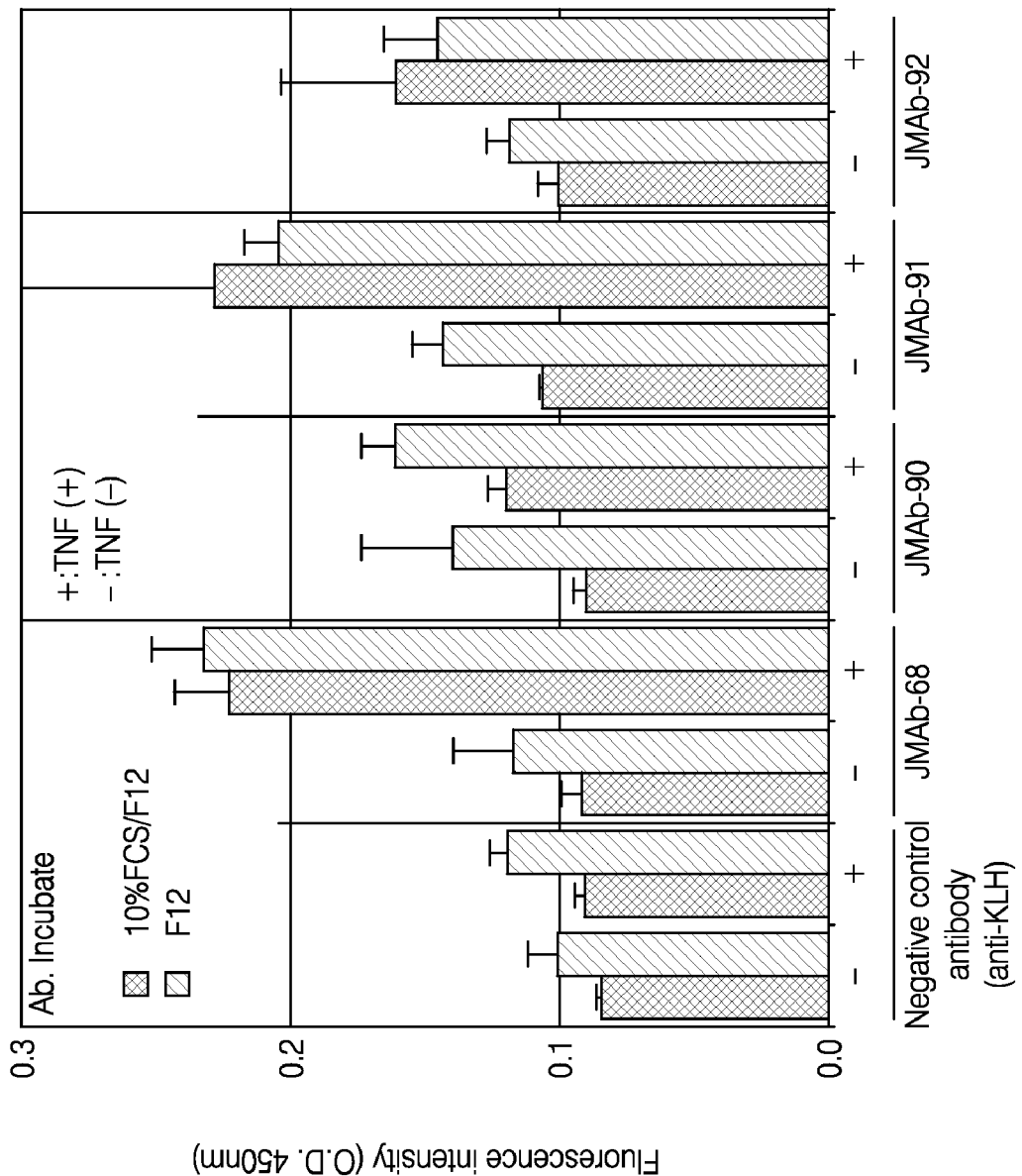

FIG. 5 is a diagram showing reactivity (binding activity) of human anti-human LOX-1 monoclonal antibodies to human LOX-1 on the surface of cells of natural human cell line HeLa S-3, which was analyzed by cell ELISA. The vertical axis indicates fluorescence intensity, and the horizontal axis indicates the type of human anti-human LOX-1 monoclonal antibody tested.

Figure 6:
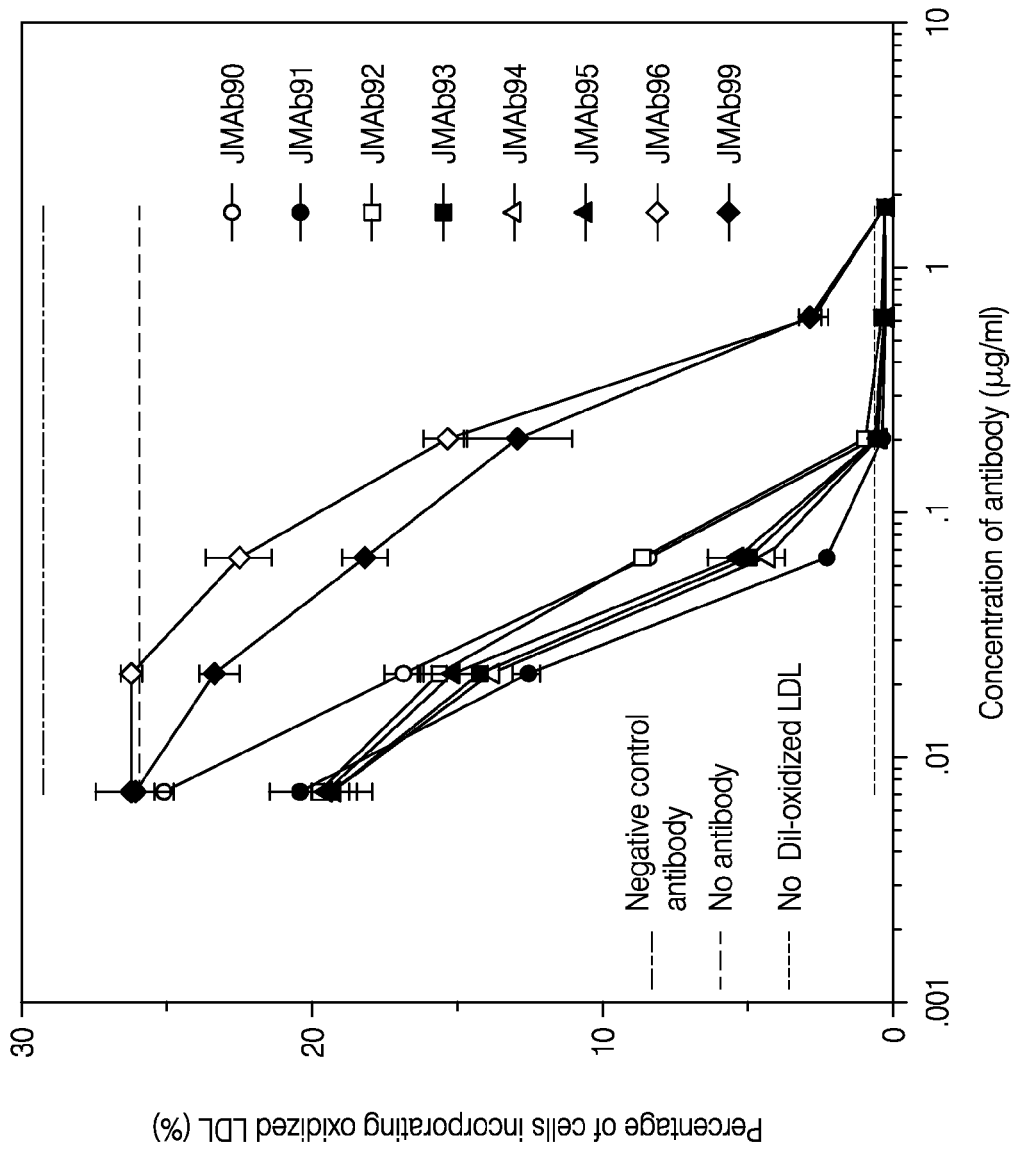

FIG. 6 is a diagram showing the inhibitory activity of the human anti-human LOX-1 monoclonal antibodies on the incorporation of oxidized LDL into cells of human-derived natural cell line HeLa S-3. The vertical axis indicates the percentage (%) of oxidized LDL incorporated into cells, and the horizontal axis indicates the concentration of the human anti-human LOX-1 monoclonal antibody added.

Figure 7:
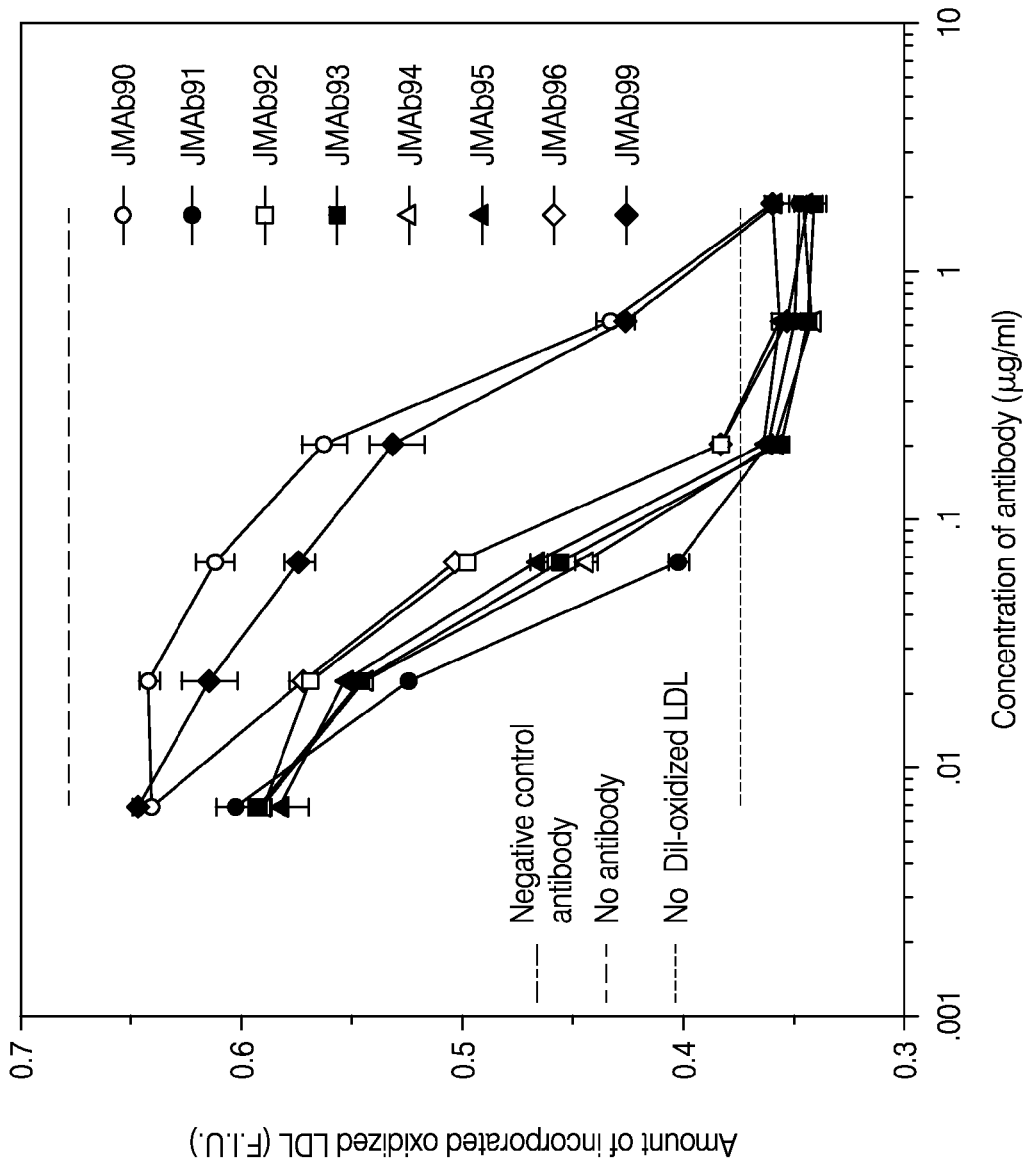

FIG. 7 is a diagram showing the inhibitory activity of the human anti-human LOX-1 monoclonal antibodies on the incorporation of oxidized LDL into cells of human-derived natural cell line HeLa S-3. The vertical axis indicates the fluorescence intensity as an index of the quantity of oxidized LDL incorporated into cells, and the horizontal axis indicates the concentration of human anti-human LOX-1 monoclonal antibody added.

Figure 8:
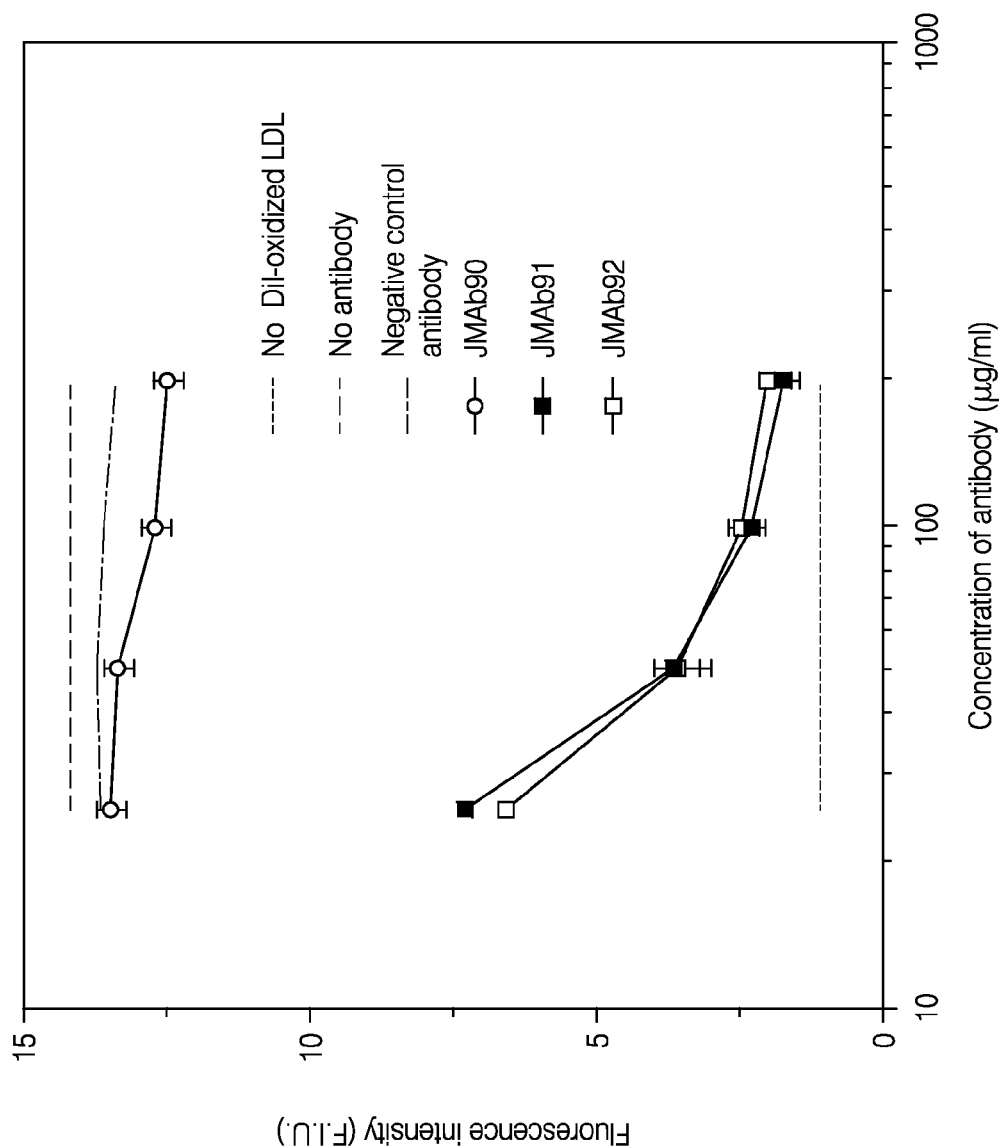

FIG. 8 is a diagram showing the inhibitory activity of the human anti-human LOX-1 monoclonal antibodies on the incorporation of oxidized LDL into recombinant CHO cells expressing bovine LOX-1. The vertical axis indicates the fluorescence intensity as an index of the quantity of oxidized LDL incorporated into cells, and the horizontal axis indicates the concentration of human anti-human LOX-1 monoclonal antibody added.

Figure 9:
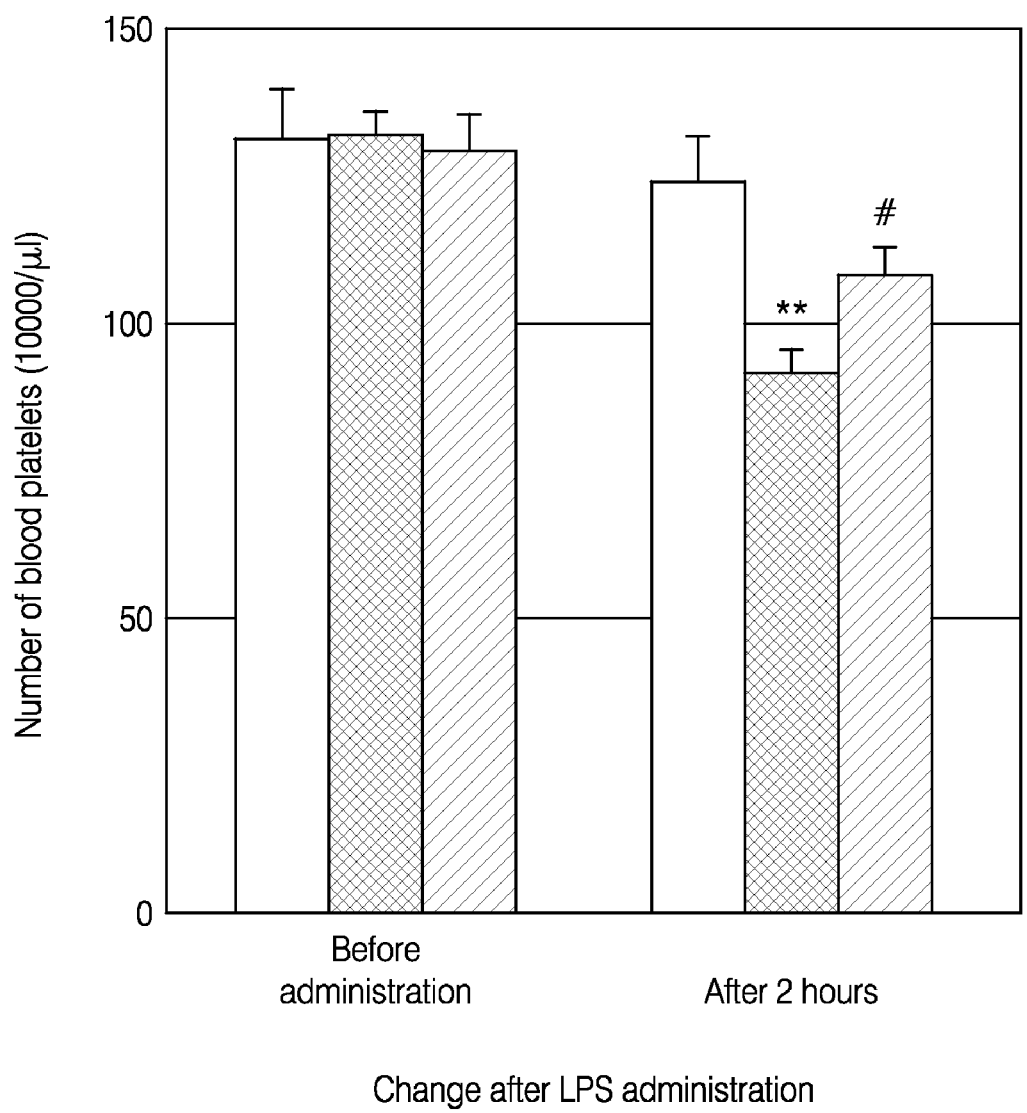

FIG. 9 is a diagram showing the therapeutic effects of anti-LOX-1 antibodies on thrombocytopenia.

Figure 10:
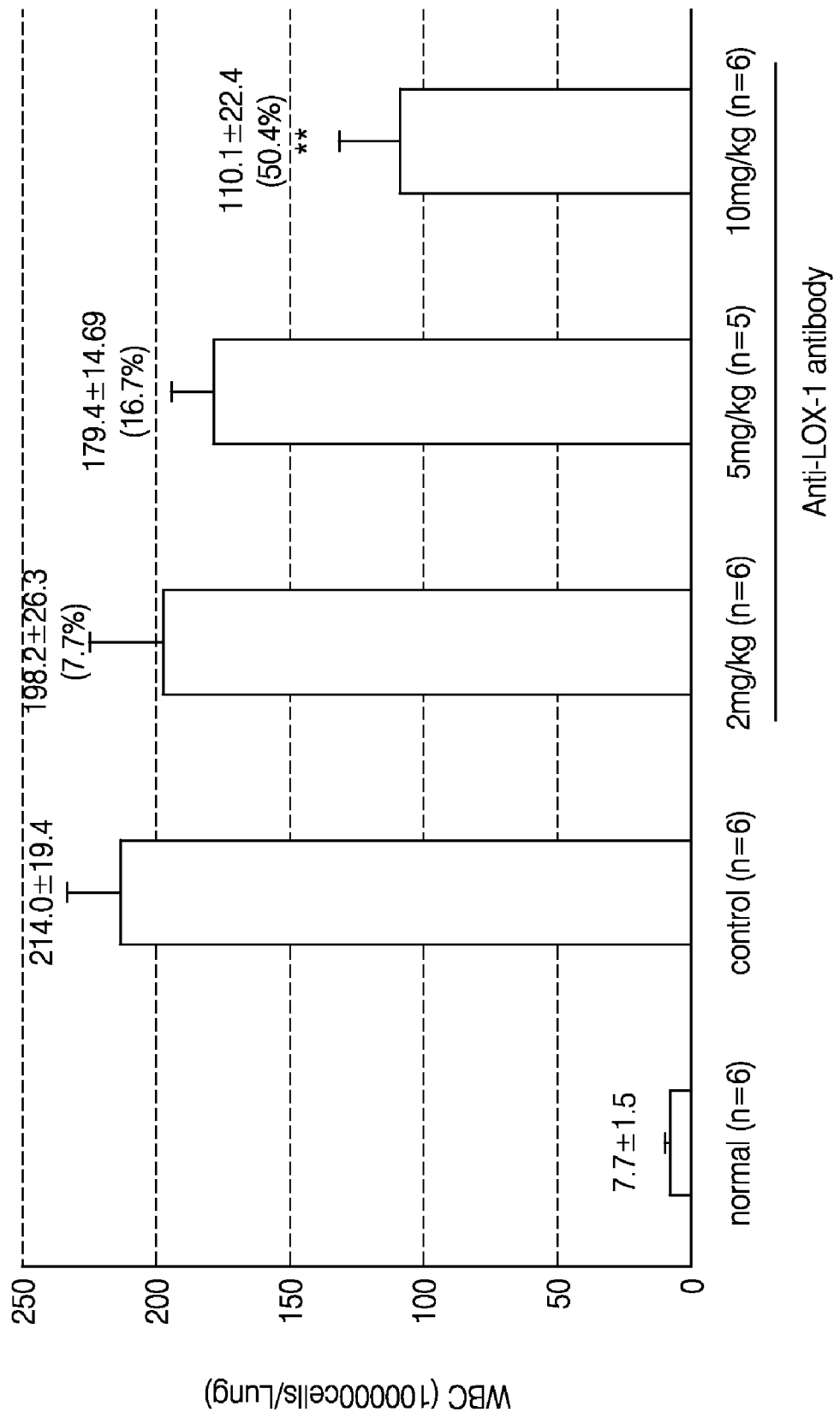

FIG. 10 is a diagram showing the inhibitory activity of the anti-LOX-1 antibodies on leukocyte infiltration into tissues.

Figure 11:
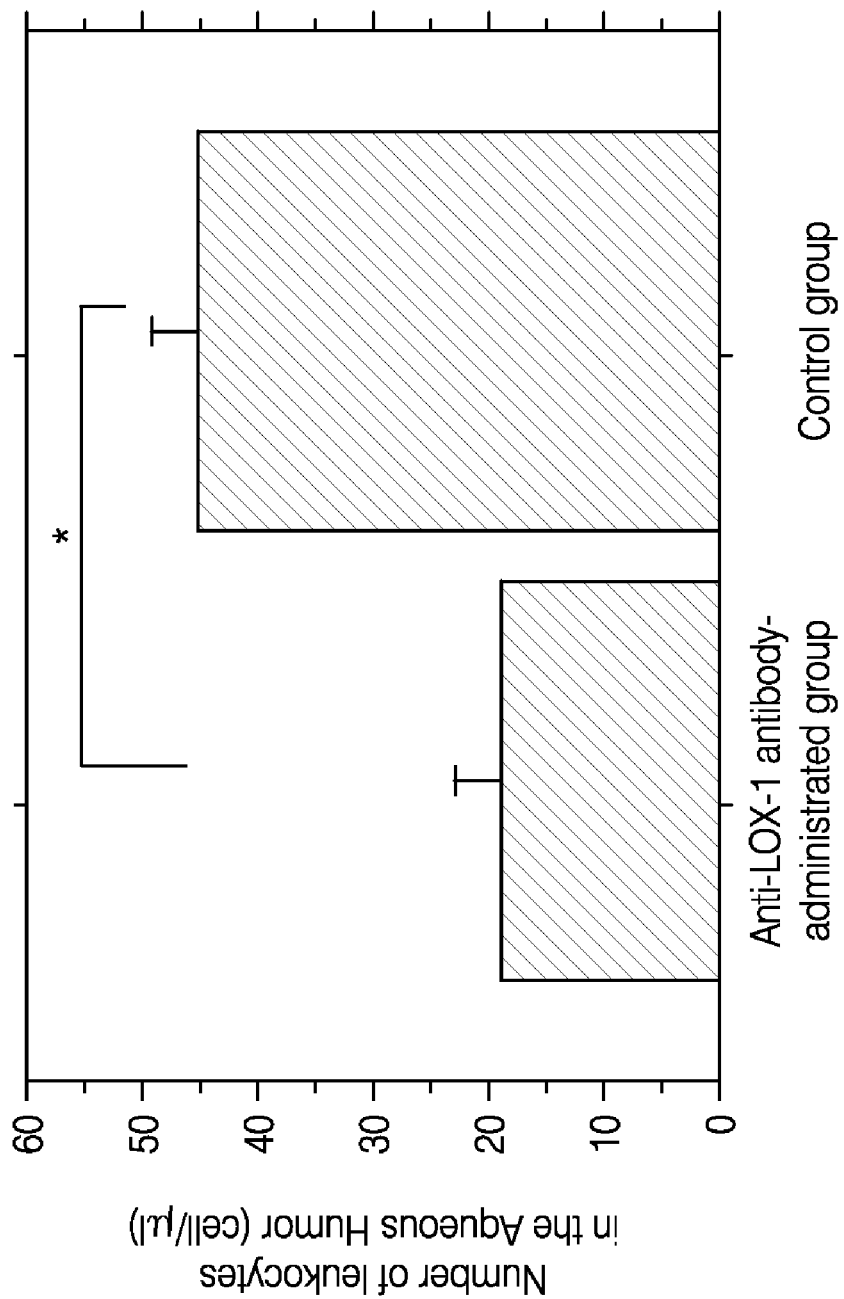

FIG. 11 is a diagram showing the inhibitory activity of the anti-LOX-1 antibodies on leukocyte infiltration into tissues.

Figure 12:
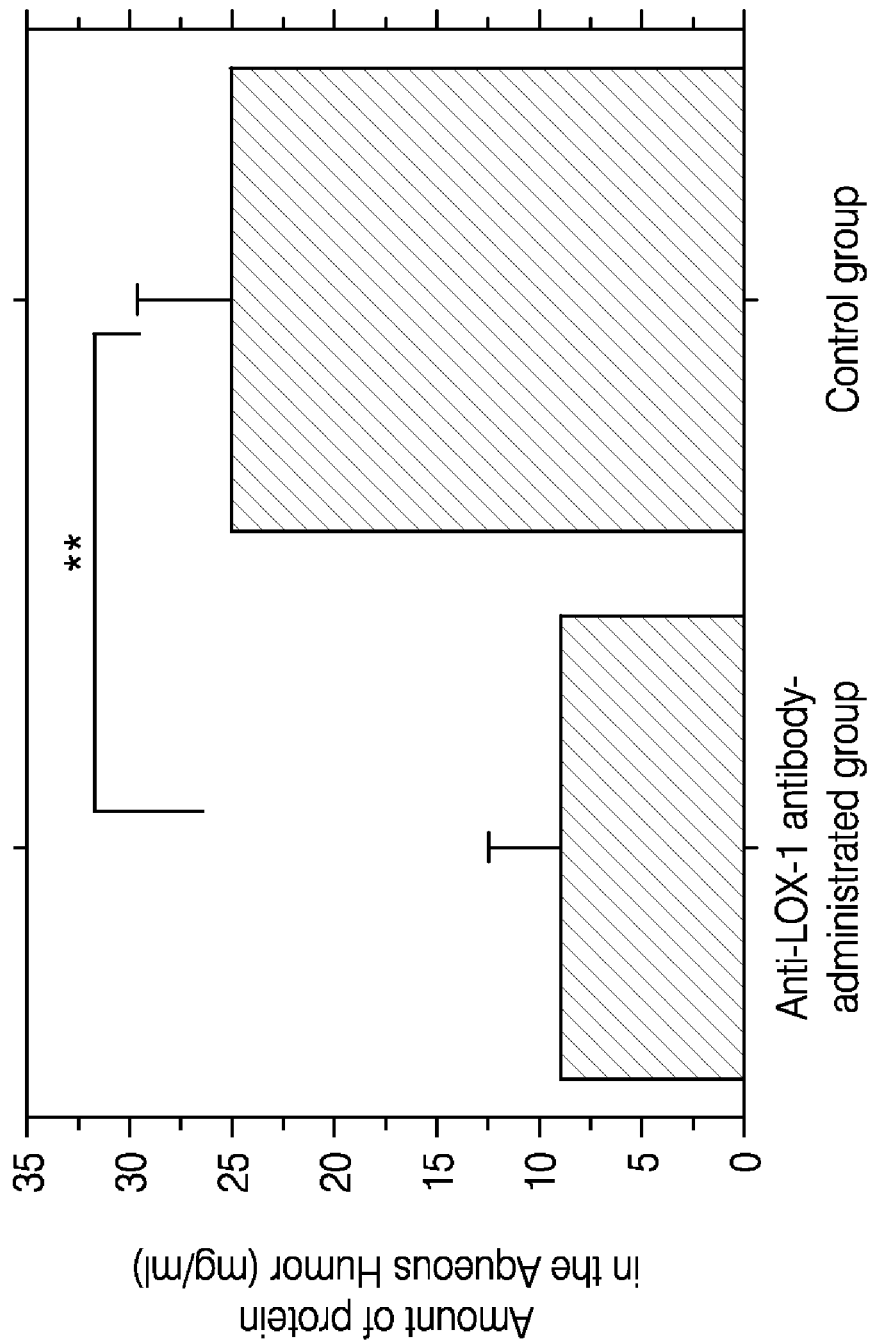

FIG. 12 is a diagram showing the inhibitory activity of the anti-LOX-1 antibodies on protein leakage as a parameter representing the progress of inflammatory reaction associated with leukocyte infiltration into tissues.

Figure 13:
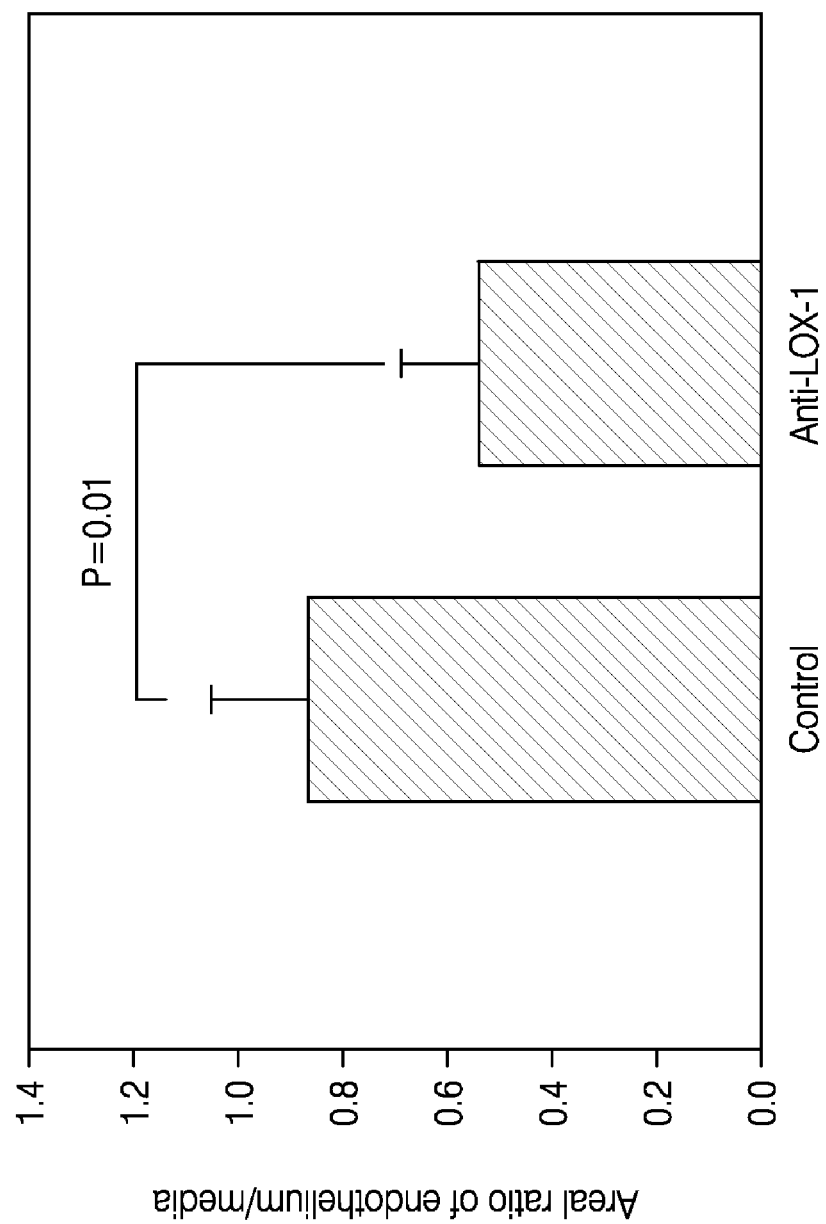

FIG. 13 is a diagram showing the inhibitory activity of the anti-LOX-1 antibodies on vascular restenosis after PTCA.

Figure 14:
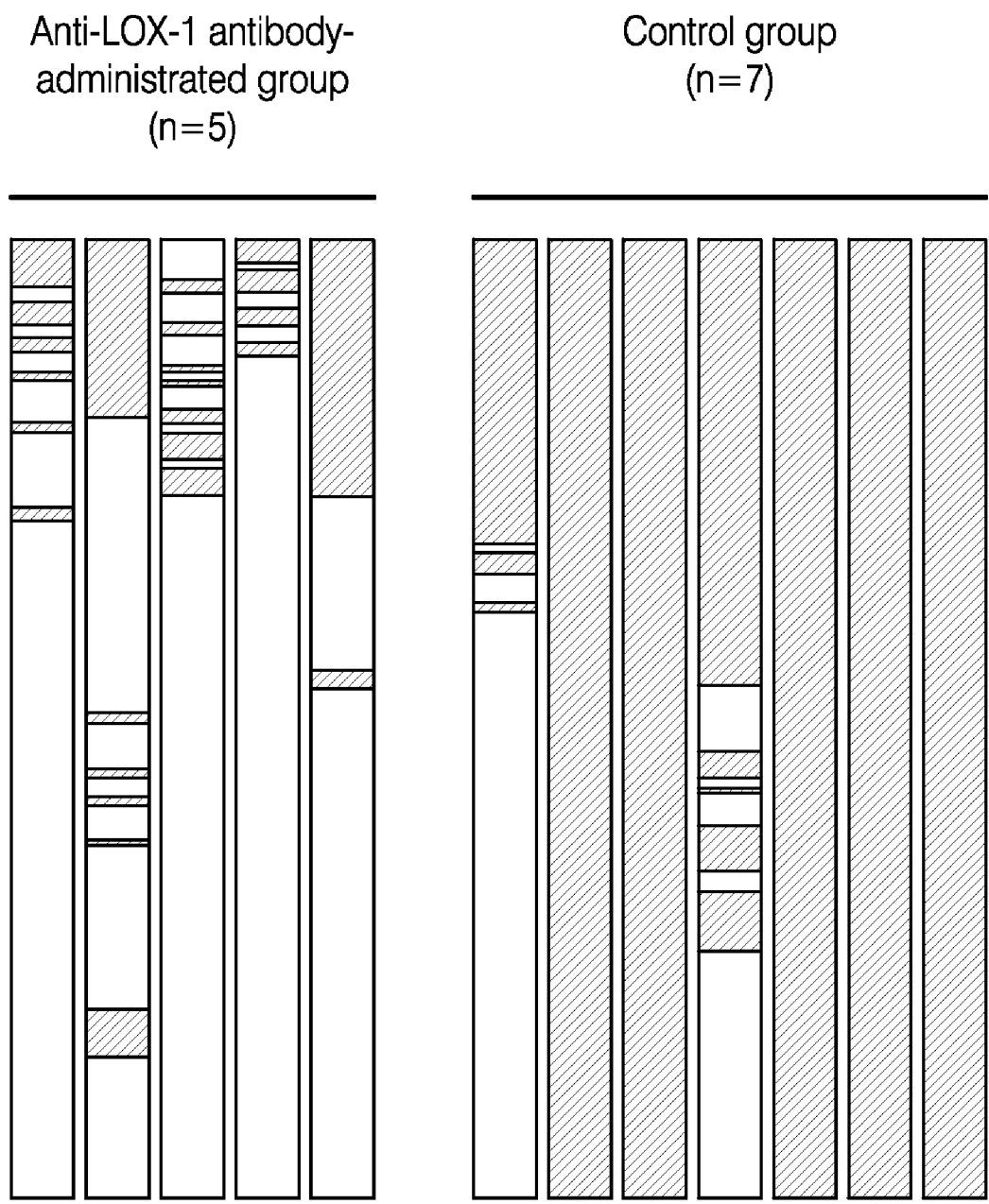

FIG. 14 is a diagram showing the inhibitory activity of the anti-LOX-1 antibodies on arterial thrombus formation. The dark regions schematically indicate the duration of vascular occlusion (thrombus formation) and the white regions schematically indicate the duration of blood flow.

Figure 15:
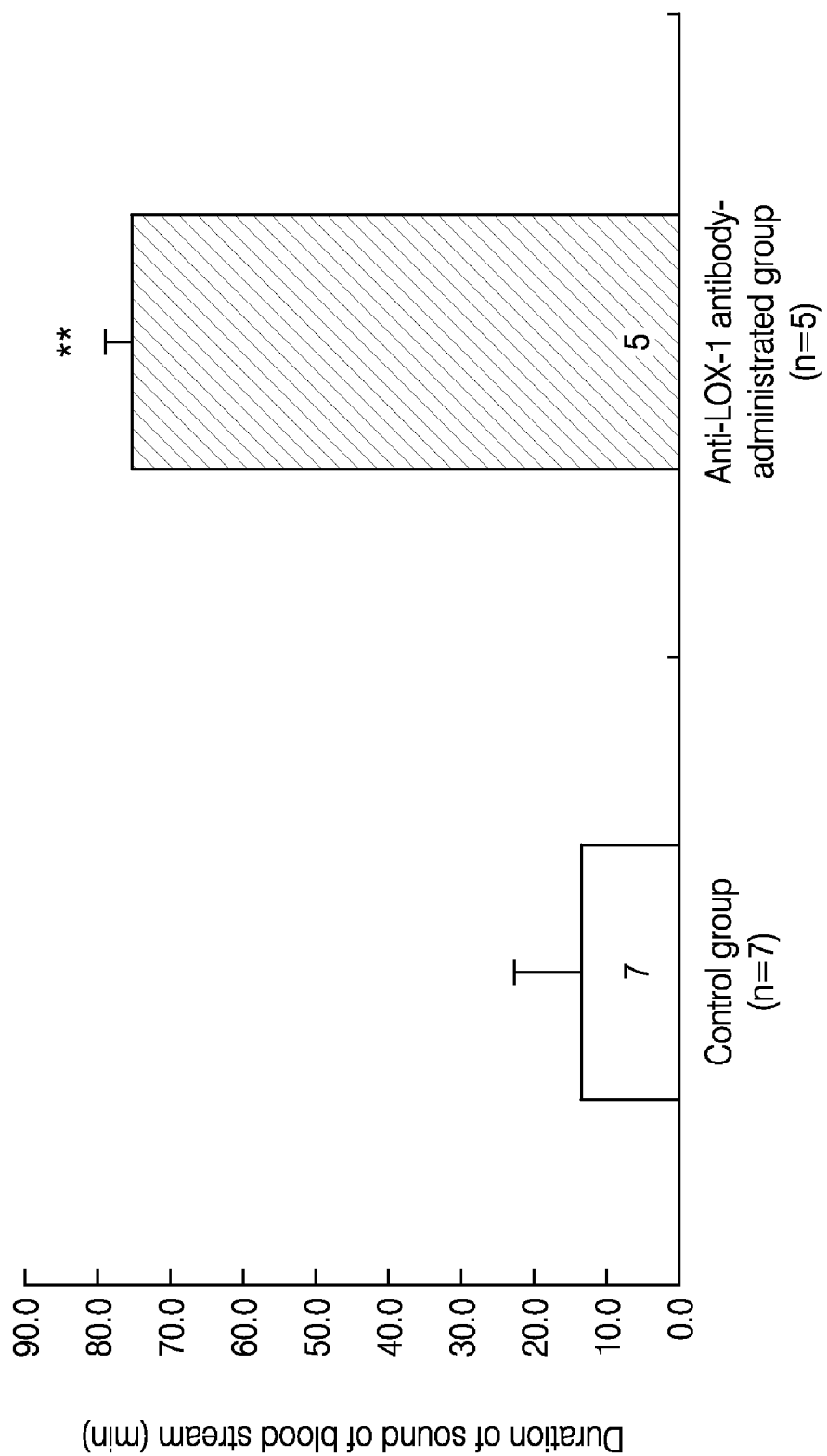

FIG. 15 is a diagram showing the inhibitory activity of anti-LOX-1 antibody on arterial thrombus formation. The vertical axis indicates the duration of blood flow (sound of blood stream).

DETAILED DESCRIPTION

The interaction (the binding of ligands of LOX-1, and LOX-1-mediated incorporation of the ligands into cells) between oxidized LDL receptor (LOX-1) and various in-vivo ligands (modified LDLs such as oxidized LDLs, apoptotic cells, senescent erythrocytes, activated blood platelets, and such) is potentially deeply involved in a variety of disease symptoms, for example, the onset of arteriosclerosis, thrombocytopenia, kidney diseases, various types of inflammation (for example, myocardial ischemic reperfusion injury, inflammatory reactions after percutaneous transluminal coronary recanalization (PTCR) or percutaneous transluminal coronary angioplasty (PTCA)), vascular restenosis after PTCA and PTCR, and thrombogenesis in blood vessels.

Thus, it is conceivable that such clinical conditions could be treated or prevented by suppressing the interaction between oxidized LDL receptor and a ligand, for example, by using a substance that binds to the oxidized LDL receptor or a substance (for example, a synthetic low-molecular-weight chemical substance, or an antibody or a portion thereof) that inhibits the oxidized LDL receptor-mediated incorporation of the ligand of oxidized LDL receptor into cells.

Accordingly, an objective of the present invention is to provide a human monoclonal antibody against human oxidized LDL receptor (LOX-1), such antibody being extremely useful in the treatment of the various diseases described above; a pharmaceutical composition to treat the above-mentioned diseases, which comprises a substance (for example, any monoclonal antibody against oxidized LDL receptor, or a synthetic low-molecular-weight chemical substance) that inhibits the interaction between the oxidized LDL receptor and a ligand thereof, or with a human monoclonal antibody; and methods for treating or preventing the above diseases.

The present inventors conducted exhaustive studies related to human monoclonal antibodies against human oxidized LDL receptor (LOX-1) to achieve the above-mentioned objective. As a result, the present inventors succeeded, for the first time in the world, in preparing a variety of human monoclonal antibodies that bind to human oxidized LDL receptor, in particular, various human monoclonal antibodies that bind to human oxidized LDL receptor and inhibit the incorporation of in-vivo oxidized LDL receptor ligands (such as oxidized LDL) into cells. This was achieved by immunizing transgenic mice created to produce human antibodies using recombinant technology, with soluble recombinant oxidized LDL receptors.

Further, the present inventors found that the human monoclonal antibodies of the present invention, which bind to human oxidized LDL receptor (LOX-1), not only significantly inhibit the human oxidized LDL receptor-mediated incorporation of various in-vivo ligands (oxidized LDL, and such) into cells, but also have therapeutic, suppressive, and/or preventive effects on various diseases (for example, arteriosclerosis, thrombocytopenia, kidney disease, various types of inflammation (for example, myocardial ischemic reperfusion injury, inflammatory reactions after percutaneous transluminal coronary recanalization (PTCR) or percutaneous transluminal coronary angioplasty (PTCA)), vascular restenosis after PTCA and PTCR, and such) and thrombogenesis in blood vessels, and thus completed the present invention.

As the monoclonal antibodies of the present invention are derived from humans, they do not induce severe host immunorejections due to antigenicity, e.g., HAMA (human anti-mouse antigenicity), which is a major therapeutic problem (side effect) in medical treatments that use antibody pharmaceuticals comprised of antibodies derived from non-human mammals, such as mice. Therefore, the present invention dramatically elevates the value of antibodies as pharmaceuticals.

Thus, the human anti-human oxidized LDL receptor (LOX-1) monoclonal antibodies of the present invention, or pharmaceutical compositions comprising these human monoclonal antibodies, do not induce host immunorejection as caused by HAMA, and therefore, can be used as antibody pharmaceuticals for treating and preventing the above-mentioned diseases, by suppressing and inhibiting the onset and/or progress of the diseases.

Furthermore, like the monoclonal antibodies, pharmaceutical compositions comprising a substance having the activity to inhibit the interaction between human oxidized LDL receptor and a ligand thereof (the binding of the ligand of oxidized LDL receptor or oxidized LDL receptor-mediated incorporation of the ligand into cells) are extremely useful in the treatment and/or prevention of various disease symptoms such as described above.

Specifically, the present invention provides:
(1) a human monoclonal antibody, or a portion thereof, which binds to the human oxidized LDL receptor;
(2) the human monoclonal antibody according to (1), or a portion thereof, which has the activity to inhibit the binding of oxidized LDL to a human oxidized LDL receptor or to inhibit the human oxidized LDL receptor-mediated incorporation of oxidized LDL into cells;
(3) the human monoclonal antibody according to (1) or (2) or a portion thereof, which belongs to the immunoglobulin class of IgG1 or IgG4;
(4) the human monoclonal antibody according to any one of (1) to (3), or a portion thereof, wherein the association rate constant (ka) in the binding between the human monoclonal antibody and human oxidized LDL receptor is $10 \times 10^4$ (1/M·Sec) or higher;
(5) the human monoclonal antibody according to any one of (1) to (3), or a portion thereof wherein the dissociation rate constant (kd) between the human monoclonal antibody and human oxidized LDL receptor is $1.0 \times 10^{-2}$ (1/Sec) or lower;
(6) the human monoclonal antibody according to any one of (1) to (3), or a portion thereof wherein the dissociation constant (Kd) between the human monoclonal antibody and human oxidized LDL receptor is $1.0 \times 10^{-6}$ (M) or lower;
(7) the human monoclonal antibody according to (4) or a portion thereof, wherein the association rate constant (ka) is $1.0 \times 10^5$ (1/M·Sec) or higher;
(8) the human monoclonal antibody according to (5), or a portion thereof, wherein the dissociation rate constant (kd) is $1.0 \times 10^{-4}$ (1/Sec) or lower;
(9) the human monoclonal antibody according to (6), or a portion thereof, wherein the dissociation constant (Kd) is $1.0 \times 10^{-7}$ (M) or lower;
(10) the human monoclonal antibody according to (9), or a portion thereof wherein the dissociation constant (Kd) is $1.0 \times 10^{-8}$ (M) or lower;
(11) the human monoclonal antibody according to any one of (1) to (10), or a portion thereof, which is derived from a transgenic non-human mammal having the ability to produce human antibodies;
(12) the human monoclonal antibody according to (11), or a portion thereof, which is obtained by immunizing a transgenic non-human mammal having the ability to produce human antibodies with cells expressing human oxidized LDL receptor, a soluble membrane fraction from the cells, the entire human oxidized LDL receptor or a portion thereof;
(13) the human monoclonal antibody according to (11) or (12) or a portion thereof, wherein the transgenic non-human mammal is a transgenic mouse;
(14) a cell producing the human monoclonal antibody according to any one of (1) to (13);
(15) the cell according to (14), which is a fused cell that has obtained the ability to produce the human monoclonal antibody as a result of cell fusion between a mammalian B cell and mammalian myeloma cell;

(16) the cell according to (14), which is a transgenic cell transformed by introducing into the cell either or both DNAs encoding a heavy chain and a light chain of the human monoclonal antibody;

(17) a pharmaceutical composition comprising the human monoclonal antibody according to any one of (1) to (13), or a portion thereof, and a pharmaceutically acceptable carrier;

(18) the pharmaceutical composition according to (17), which is used to inhibit the binding between an in-vivo ligand of human oxidized LDL receptor and human oxidized LDL receptor or the incorporation of the ligand into cells expressing the oxidized LDL receptor;

(19) the pharmaceutical composition according to (17), which is used to treat arteriosclerosis;

(20) the pharmaceutical composition according to (18), which is used to treat a disease caused by the binding of blood platelets or activated blood platelets to the oxidized LDL receptor, or the incorporation of blood platelets or activated blood platelets into cells expressing the oxidized LDL receptor;

(21) the pharmaceutical composition according to (20), wherein the disease involves the symptoms of thrombocytopenia;

(22) the pharmaceutical composition according to (20), wherein the disease is a kidney disease;

(23) the pharmaceutical composition according to (17), which is used to inhibit leukocyte infiltration into tissues;

(24) the pharmaceutical composition according to (23), wherein leukocyte infiltration into tissues is observed in inflammatory reactions during arteriosclerosis, during myocardial ischemic reperfusion injury, after percutaneous transluminal coronary recanalization (PTCR), or after percutaneous transluminal coronary angioplasty (PTCA);

(25) the pharmaceutical composition according to (17), which is used to treat inflammation;

(26) the pharmaceutical composition according to (25), wherein the inflammation is due to arteriosclerosis, myocardial ischemic reperfusion injury, after percutaneous transluminal coronary recanalization (PTCR), or after percutaneous transluminal coronary angioplasty (PTCA);

(27) the pharmaceutical composition according to (17), which is used to treat vascular restenosis after percutaneous transluminal coronary recanalization (PTCR) or percutaneous transluminal coronary recanalization (PTCR);

(28) a pharmaceutical composition for suppressing or preventing thrombus formation, wherein the pharmaceutical composition comprises a substance that has the activity of inhibiting the binding of an in-vivo ligand of human oxidized LDL receptor, or the incorporation of the ligand into cells expressing the oxidized LDL receptor;

(29) the pharmaceutical composition according to (28), wherein the substance is a monoclonal antibody, or a portion thereof, which binds to the human oxidized LDL receptor; and

(30) the pharmaceutical composition according to (29), wherein the monoclonal antibody, or a portion thereof, is the human monoclonal antibody according to any one of (1) to (13), or a portion thereof.

The present invention is described in detail herein below by defining terms used herein.

Herein, the term "mammal" refers to a human, cow, goat, rabbit, mouse, rat, hamster, or guinea pig; preferably a human, rabbit, rat, hamster, or mouse; and more preferably a human, rabbit, rat, hamster, or mouse.

The term "mammal other than a human" and "non-human mammal" refers to any mammal, such as those mentioned above except humans.

The term "amino acid" as used herein refers to any amino acid existing in nature, and preferably, the following amino acids represented by the three letter or single letter codes used to represent amino acids:

(Gly/G) glycine, (Ala/A) alanine, (Val/V) valine, (leu/L) leucine, (Ile/I) isoleucine, (Ser/S) serine, (Thr/T) threonine, (Asp/D) aspartic acid, (Glu/E) glutamic acid, (Asn/N) asparagine, (Gln/Q) glutamine, (Lys/K) lysine, (Arg/R) arginine, (Cys/C) cysteine, (Met/M) methionine, (Phe/F) phenylalanine, (Tyr/Y) tyrosine, (Trp/W) tryptophan, (His/H) histidine, and (Pro/F) proline.

The term "human oxidized-LDL receptor" (often called "human LOX-1") as used in the present invention refers to a human oxidized-LDL receptor (ox-LDL receptor) having the structure and functions described in previous reports, sequence listings, and such (SEQ ID NO: 2; Nature, Vol. 386, p. 73-77, 1997; Genomics, Vol. 54, No. 2, p. 191-199, 1998; Biochem. J., Vol. 339, Part 1, P. 177-184, 1999; Genbank Accession No. NP 002534).

In addition, in the context of this invention, the term "human oxidized-LDL receptor" (often called "human LOX-1") includes mutants of the natural human oxidized-LDL receptor, which have substantially the same amino acid sequence as that of the native primary structure (amino acid sequence) described in the above-mentioned reports.

Herein, the term "mutants of the natural human oxidized-LDL receptor having substantially the same amino acid sequence" refers to the following mutant proteins;

Specifically, such proteins include a mutant protein having an amino acid sequence wherein one or more amino acids, preferably 1 to 10 amino acids, particularly preferably 1 to 5 amino acids, in the amino acid sequence of the natural human oxidized-LDL receptor have been substituted, deleted and/or modified, and a mutant protein having an amino acid sequence wherein one or more amino acids, preferably 1 to 10 amino acids, particularly preferably 1 to 5 amino acids, have been added to the amino acid sequence, so long as the protein has substantially the same biological properties as the natural human oxidized-LDL receptor.

Furthermore, a mutant having a combination of two or more of the above alterations, including a substitution, deletion, modification, and addition, is also included.

The human oxidized-LDL receptor of the present invention can be produced by methods known in the technical field of the instant invention, such as recombinant technology, chemical synthesis, and cell culture, or by modified methods thereof.

The human oxidized-LDL receptor (also referred to as "human LOX-1") of the present invention, also includes "a portion" of the human oxidized-LDL receptor. The term "a portion" as used herein refers to a polypeptide comprising any arbitrary partial amino acid sequence derived from the above-defined human oxidized-LDL receptor.

Preferably, the term "portion" refers to the extracellular domain of the human oxidized-LDL receptor defined above, or an arbitrary portion thereof.

"A portion" of the human oxidized-LDL receptor (preferably, the extracellular domain of the human oxidized-LDL receptor, or any portion thereof) can be produced according to methods known in the technical field of the present invention, or modified methods thereof, including recombinant technology and chemical synthesis. It can also be produced by appropriately digesting the human oxidized-LDL receptor isolated by the cell culture method with proteases and such.

The "substance" of the present invention, specifically the "substance that has the activity to inhibit the binding between an in-vivo ligand of human oxidized-LDL receptor and the oxidized-LDL receptor or to inhibit the incorporation of the ligand by the oxidized-LDL receptor expressing cell", encompasses naturally occurring substances and artificially prepared arbitrary substances.

The substances can be categorized into "proteinaceous substances" and "non-proteinaceous substances".

As used herein, the term "in-vivo ligand of oxidized LDL receptor" refers to any in-vivo ligand to which an oxidized LDL receptor binds, for example, oxidized LDL, modified LDL (acetylated LDL, succinylated LDL, and such), an apoptotic cell, a senescent erythrocyte, or an activated blood platelet.

The term "proteinaceous substance" includes polypeptides, polyclonal antibodies, monoclonal antibodies, and portions of the monoclonal antibodies.

When the substance is an antibody, a monoclonal antibody is preferable. When the substance is a monoclonal antibody, it includes not only monoclonal antibodies derived from a non-human mammal, but also recombinant chimeric monoclonal antibodies, recombinant humanized monoclonal antibodies, and the above-mentioned "human monoclonal antibodies".

When the substance is a polypeptide, it includes the following polypeptides, fragments of the polypeptides (oligopeptides), fused polypeptides, and chemically modified peptides thereof. Oligopeptides include peptides consisting of 5 to 30 amino acids, preferably 5 to 20 amino acids. The chemically modified peptides can be designed depending on various purposes, so as to increase the half-life in blood when it is injected to a living body, or to enhance resistance to degradation or absorption in the digestive tract when it is administered orally The term "non-proteinaceous substance" includes DNA, RNA, and chemically synthesized compounds.

As used herein, the term "DNA" refers to DNA comprising a partial nucleotide sequence, or a chemically modified sequence, of a DNA that is useful as an antisense DNA pharmaceutical, designed based on the nucleotide sequence of the DNA (including cDNA and genomic DNA) encoding the above-mentioned oxidized LDL receptor (LOX-1). Specifically, the antisense DNA can inhibit the transcription of DNA encoding LOX-1 to mRNA or the translation of the mRNA to the protein by hybridizing to the DNA or RNA encoding LOX-1.

As used herein, the term "partial nucleotide sequence" refers to a partial nucleotide sequence comprising an arbitrary number of nucleotide residues in an arbitrary region. The partial nucleotide sequence includes a partial nucleotide sequence comprising 5 to 100 consecutive nucleotides, preferably a partial nucleotide sequence comprising 5 to 70 consecutive nucleotides, more preferably a partial nucleotide sequence comprising 5 to 50 consecutive nucleotides, still more preferably a partial nucleotide sequence comprising 5 to 30 consecutive nucleotides.

When the DNA is used as an antisense pharmaceutical, residues in a partial nucleotide sequence of the DNA can be modified chemically to increase the half-life (stability) in blood and intercellular membrane permeability of the DNA when injected to a patient, or to increase its resistance to decomposition in digestive organs or to enhance the absorption of the DNA when given orally. Such chemical modifications include, for example, chemical modification of a phosphate bond, ribose, nucleotide, sugar moiety in oligonucleotides, and 3' and 5' ends of oligonucleotides.

In the context of the present invention, the modification of a phosphate bond includes modification of one or more bonds to any one of a phosphodiester bond (D-oligo), phosphorothioate bond, phosphorodithioate bond (S-oligo), methyl phosphonate (MP-oligo), phosphoroamidate bond, non-phosphate bond or methyl phosphonothioate bond, or combinations thereof. Modification of ribose includes modification to 2'-fluororibose or 2'-O-methylribose. Modification of a nucleotide includes modification to a 5-propynyluracil or 2-aminoadenine.

As used herein, the term "RNA" refers to "RNA comprising a partial nucleotide sequence, or a chemically modified sequence, of a RNA that is useful as an antisense RNA pharmaceutical, designed based on the nucleotide sequence of the RNA encoding the above-mentioned oxidized LDL receptor (LOX-1). The antisense RNA can inhibit the transcription of DNA encoding LOX-1 to mRNA or the translation of the mRNA to the protein by hybridizing to the DNA or RNA encoding LOX-1.

As used herein, the term "partial nucleotide sequence" refers to a partial nucleotide sequence comprising an arbitrary number of nucleotide residues in an arbitrary region. The partial nucleotide sequence includes a partial nucleotide sequence comprising 5 to 100 consecutive nucleotides, preferably a partial nucleotide sequence comprising 5 to 70 consecutive nucleotides, more preferably a partial nucleotide sequence comprising 5 to 50 consecutive nucleotides, still more preferably a partial nucleotide sequence comprising 5 to 30 consecutive nucleotides.

The antisense RNA may be modified chemically. Residues in a partial nucleotide sequence of the RNA can be chemically modified to increase the half-life in blood and intracellular membrane permeability of the RNA when injected to a patient, or to increase its resistance to decomposition in digestive organs or to enhance the absorption of the RNA when given orally. Such chemical modifications include for example, the same chemical modifications used to modify the above-mentioned antisense DNA.

A "chemically-synthesized compound" is an arbitrary compound, other than DNA, RNA or a proteinaceous substance, and has a molecular weight of about 100 to 1000 Da or smaller, preferably a molecular weight of about 100 to 800 Da, more preferably a molecular weight of 100 to 600 Da.

The "human monoclonal antibody" of this invention is a human monoclonal antibody that binds to the human oxidized-LDL receptor defined above.

More specifically, the human monoclonal antibody includes a human immunoglobulin in which all the regions, including the variable region and constant region of the heavy chain (H chain), and the variable region and constant region of the light chain (L chain) constituting the immunoglobulin, are from genes encoding a human immunoglobulin. The L chain includes the human κ chain and the human λ chain.

A human monoclonal antibody that binds to the human oxidized-LDL receptor of the present invention is a monoclonal antibody having any one of the features selected from the group consisting of (1) to (13) described above.

More specifically, the term "monoclonal antibody" refers to a variety of monoclonal antibodies with various properties and industrial utilities described below in the examples and as indicated in the drawings.

In a preferred embodiment, the human monoclonal antibody of the present invention is a human monoclonal antibody that binds to the human oxidized-LDL receptor, described in any one of (2) to (13) above.

In a particularly preferred embodiment, the human monoclonal antibody of the invention is the human monoclonal antibody binding to the human TGF-β type II receptor of either (10) or (11) of the present invention.

A "human monoclonal antibody" of the present invention can be prepared by immunizing a human antibody-producing transgenic non-human mammal with any one of the immunogens (antigens) below:

(i) naturally occurring cells or artificially established cell lines expressing on the cell surface the above-defined human oxidized-LDL receptor;

(ii) recombinant cells, which have been prepared by DNA recombinant technology to express on the cell surface the above-defined human oxidized-LDL receptor;

(iii) cell lysate prepared by solubilizing the cells of (i) or (ii), or polypeptide fragments of human oxidized-LDL receptor purified from the cell lysate;

(iv) recombinant cells, which have been prepared by DNA recombinant technology to express a portion of the above-defined human oxidized-LDL receptor (particularly, the extracellular domain or an arbitrary peptide thereof are preferred) as a soluble polypeptide;

(v) culture supernatant obtained by culturing the recombinant cells of (iv), or the extracellular domain polypeptide of the human oxidized-LDL receptor purified from the culture supernatant (soluble human oxidized-LDL receptor); and (vi) chemically synthesized partial human oxidized-LDL receptor (particularly, the extracellular domain or an arbitrary peptide thereof are preferred).

Further, a human monoclonal antibody of the present invention can also be obtained from the culture supernatant of the "recombinant cells" of the present invention, which produce recombinant human monoclonal antibodies. The recombinant cells are prepared using DNA recombinant technology, by transforming host cells with cDNAs encoding the heavy chain or light chain of the human monoclonal antibody of the present invention.

Further, a human monoclonal antibody of the present invention may be any one of the isotypes including IgG (IgG1, IgG2, IgG3, and IgG4), IgM, IgA (IgA1 and IgA2), IgD, or IgE; preferably IgG (IgG1, IgG2, IgG3, and IgG4); and more preferably IgG1, IgG2, or IgG4. IgG1 and IgG4 are particularly preferred.

A human monoclonal antibody of the present invention can be produced by immunizing human antibody-producing transgenic non-human mammals, such as the human antibody-producing transgenic mice described below, with any one of the immunogens (antigens) described above as (i) to (vi). Such human monoclonal antibodies can be prepared according to conventional methods for preparing monoclonal antibodies.

Specifically, human antibody producing transgenic non-human mammals are immunized, for example, with an antigen mentioned above together with Freund's adjuvant, if necessary. Polyclonal antibodies can be obtained from the serum obtained from the immunized animal. Monoclonal antibodies are produced as follows: Hybridomas (fused cells) are produced by fusing the antibody-producing cells, obtained from the immunized animal, and myeloma cells, incapable of producing autoantibodies. Then, the hybridomas are cloned, and clones producing the monoclonal antibodies showing specific affinity to the antigen used for immunizing the mammal are screened.

More specifically, a monoclonal antibody can be produced as follows: Immunizations are performed by injecting or implanting, once or several times, an immunogen of any one of (i) to (iii) above, if necessary, with Freund's adjuvant, subcutaneously, intramuscularly, intravenously, through the footpad, or intraperitoneally into the human antibody-producing transgenic non-human mammal (particularly preferred are the "human antibody-producing transgenic mouse" described below). Usually, immunizations are performed once to four times every one to fourteen days after the first immunization Antibody-producing cells are obtained from the immunized mammal in about one to five days after the last immunization. The number of times and interval of the immunizations can be appropriately altered according to the properties of the used immunogen.

Hybridomas (fused cells) that secrete human monoclonal antibodies can be prepared according to the method by Kohler and Milstein (Nature, Vol. 256, pp. 495-497 (1975)) or a modified method thereof. Namely, hybridomas are prepared by fusing antibody-producing cells from the spleen, lymph node, bone marrow, or tonsil (preferably spleen) of a human antibody-producing transgenic non-human mammal immunized as mentioned above, with myclomas that lack the autoantibody-producing ability and which are derived from, preferably, mammal, such as mouse, rat, guinea pig, hamster, rabbit, or human, or more preferably, mouse, rat, or human.

For example, mouse-derived myeloma P3/X63-AG8.653 (653, ATCC No. CRL1580), P3/NSI/1-Ag4-1 (NS-1), P3/X63-Ag8.U1 (P3U1), SP2/0-Ag14 (Sp2/0, Sp2), PAI, F0, or BW5147; rat-derived myeloma 210RCY3-Ag.2.3; or human-derived myeloma U-266AR1, GM1500-6TG-A1-2, UC729-6, CEM-AGR, D1R11, or CEM-T15 can be used as a myeloma for the cell fusion.

Monoclonal antibody producing cells (e.g., hybridoma) can be screened by culturing the cells, for example, in microtiter plates and by measuring the reactivity of the culture supernatant in wells wherein the growth of hybridoma is observed, towards the immunogen used for the immunization mentioned above, for example, by an enzyme immunoassay, such as radio immunoassay (RIA) and enzyme-linked immuno-solvent assay ELISA).

A monoclonal antibody can be produced from hybridoma by cultivating the hybridoma in vitro or in vivo, such as in the ascites of a mouse, rat, guinea pig, hamster, or rabbit, preferably a mouse or rat, more preferably a mouse, and isolating the antibody from the resulting culture supernatant or ascites fluid of the mammal.

Furthermore, a monoclonal antibody can be obtained in a large quantity by cloning genes encoding a monoclonal antibody from a hybridoma or "recombinant cell" producing a recombinant human monoclonal antibody of the present invention described below, generating a transgenic animal, such as a cow, goat, sheep, or pig wherein the genes encoding the monoclonal antibody are integrated into the endogenous genome using a transgenic animal generating technique, and recovering the monoclonal antibody derived from the human monoclonal antibody gene from milk of the transgenic animals (Nikkei Science, April, pp. 78-84 (1997)).

Monoclonal antibody-producing cells can be cultured in vitro depending on numerous conditions, such as the properties of cells that are cultured, the objective of the test/study, and the culture method, using known nutrient media or any nutrient media derived from known basal media for growing, maintaining, and storing hybridomas to produce monoclonal antibodies in the culture supernatant.

Examples of basal media include low calcium concentration media, such as Ham'F12 medium, MCDB153 medium, and low calcium concentration MEM medium; and high calcium concentration media, such as MCDB104 medium, MEM medium, D-MEM medium, RPM1640 medium, ASF104 medium, and RD medium. The basal media can contain, for example, sera, hormones, cytokines, and/or various inorganic or organic substances depending on the objective.

Monoclonal antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), affinity chromatography using an anti-immunoglobulin column or protein A column.

The human monoclonal antibodies of the present invention also include monoclonal antibodies comprising the heavy chains and/or the light chains, wherein either or both of the chains have deletions, substitutions or additions of one or more amino acids to the sequences thereof.

The term "one or more amino acids" as used herein refers to one or more amino acid residues, and specifically indicates one to ten amino acid residues, preferably one to five amino acid residues.

A partial modification (deletion, substitution, insertion, and addition) of the amino acid sequence described above can be introduced into the human monoclonal antibodies of the present invention by partially modifying the nucleotide sequence encoding the amino acid sequence. The partial modification of a nucleotide sequence can be performed by conventional methods, such as site-specific mutagenesis (Proc. Natl. Acad. Sci. USA, Vol. 81, p. 5662-5666, 1984).

The "human antibody-producing transgenic non-human mammal" of the present invention, in the particular preferable embodiment, the human antibody-producing transgenic mouse, can be prepared according to conventional methods in literature (Nature Genetics, Vol. 7, p. 13-21, 1994; Nature Genetics, Vol. 15, p. 146-156, 1997; Published Japanese Translation of International Publication No. Hei 4-504365; Published Japanese Translation of International Publication No. Hei 7-509137; Nikkei Science, June, p. 40-50, 1995; International Publication WO94/25585; Nature, Vol. 368, p. 856-859, 1994; Published Japanese Translation of International Publication No. Hei 6-500233; and such).

The human antibody-producing transgenic mice can be produced, specifically, for example, via the following processes. Other human antibody-producing non-human transgenic mammals can be produced in the same manner.

(1) Preparing knockout mice whose endogenous immunoglobulin heavy chain gene locus has been functionally inactivated. The inactivation can be accomplished by substituting at least a portion of the endogenous mouse immunoglobulin heavy chain gene locus with a drug-resistance gene (e.g., the neomycin resistance gene, and such) through homologous recombination.

(2) Preparing knockout mice whose endogenous immunoglobulin light chain gene locus (a κ chain gene locus in particular) has been functionally inactivated. The inactivation is accomplished by substituting at least a portion of the endogenous mouse immunoglobulin light chain gene locus with a drug-resistance gene (e.g., the neomycin resistance gene, and such) through homologous recombination.

(3) Preparing transgenic mice wherein a desired portion of the human immunoglobulin heavy chain gene locus has been integrated into a mouse chromosome using a vector, such as yeast artificial chromosome (YAC) vector, capable of transporting mega base genes.

(4) Preparing transgenic mice wherein a desired portion of the human immunoglobulin light chain (a K gene in particular) gene locus has been integrated into a mouse chromosome using a vector, such as YAC vector, capable of transporting mega base genes.

(5) Preparing transgenic mice wherein both the mouse endogenous heavy chain and light chain gene loci have been functionally inactivated and both desired portions of the human immunoglobulin heavy chain and light chain genes loci have been integrated in a chromosome, wherein the preparation is achieved by crossbreeding, in an arbitrary order, the knockout mice and the transgenic mice described above in (1) to (4).

The knockout mice mentioned above can be prepared by substituting any suitable region of the mouse endogenous immunoglobulin gene locus with a foreign marker gene (e.g., neomycin resistance gene, and such) through homologous recombination so that the immunoglobulin gene locus can be inactivated, so as not to cause a rearrangement of the gene locus. For example, the method designated as positive-negative selection (PNS) can be used for the inactivation by homologous recombination (Nikkei Science, May edition, p. 52-62, 1994).

The functional inactivation of the immunoglobulin heavy chain locus can be achieved, for example, by introducing a lesion into a portion of the J region or a portion of the C region (e.g., the Cμ region, for example). The functional inactivation of the immunoglobulin light chain (κ chain, for example) can also be achieved, for example, by introducing a lesion into a portion of the J region, a portion of the C region, or a region extending from the J region to the C region.

The transgenic mouse can be prepared according to conventional methods used for producing transgenic animals (for example, see "Newest Manual of Animal Cell Experiment", LIC press, Chapter 7, pp. 361-408, (1990)). Specifically, for example, a transgenic mouse can be produced as follows: Hypoxanthine-guanine phosphoribosyl transferase (HPRT)-negative embryonic stem cells (ES cells), obtained from a normal mouse blastocyst, are fused by spheroplast fusion method with a yeast cell containing a YAC vector, wherein the gene encoding human immunoglobulin heavy chain locus or light chain locus, or its fragment and a HPRT gene have been inserted. ES cells wherein the foreign gene has been integrated into the mouse endogenous genome are screened by the HAT selection method. Then, the screened ES cells screened are microinjected into a fertilized egg (blastocyst) obtained from another normal mouse (Proc. Natl. Acad. Sci. USA, Vol. 77, No. 12, pp. 7380-7384 (1980); U.S. Pat. No. 4,873,191). The blastocyst is transplanted into the uterus of another normal mouse that serves as the foster mother. Then, chimeric transgenic mice are born from the foster mother mouse. By mating the chimeric transgenic mice with normal mice, heterozygous transgenic mice are obtained. By mating the heterozygous transgenic mice with each other, homozygous transgenic mice can be obtained according to Mendel's laws.

The term "portion of a monoclonal antibody" as used herein refers to a partial region of the human monoclonal antibody of the present invention as mentioned above, and specifically, includes F(ab')$_2$, Fab', Fab, Fv (variable fragment of antibody), sFv, dsFv (disulfide stabilized Fv), or dAb (single domain antibody) (Exp. Opin. Ther. Patents, Vol. 6, No. 5, pp. 441-456 (1996)).

"F(ab')$_2$" and "Fab" can be produced by treating immunoglobulin (monoclonal antibody) with a protease, such as pepsin and papain, and refer to antibody fragments generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments, in which an L chain composed of $V_L$ (L chain variable region) and $C_L$ (L chain constant region), and an H chain fragment composed of $V_H$(H chain variable region) and $C_H\gamma1$ ($\gamma1$ region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment wherein the two above-mentioned Fab' are connected at the hinge region. This antibody fragment is called F(ab')$_2$.

As used herein, the term "association rate constant (ka)" refers to a value representing the intensity (degree) of association of the monoclonal antibody with the target antigen thereof, which is determined based on the kinetics of the antigen-antibody reaction. The term "dissociation rate constant (kd)" refers to a value representing the intensity (degree) of dissociation of the monoclonal antibody from the target antigen thereof, which is determined based on the kinetics of the antigen-antibody reaction. The term "dissociation constant (Kd)" is calculated by dividing the "dissociation rate constant (kd)" by the "association rate constant (ka)". These constants are used as indexes representing the affinity of a monoclonal antibody for its antigen and its activity neutralizing the antigen.

The constants can be determined according to various methods. Such methods can be practiced conveniently with a commercially available assay kit, such as Biacore X (Amersham-Pharmacia), or a similar kit, according to the instructions and the experiment manual attached to the kit. The ka, kd, and Kd values determined with such a kit are given in 1/M·Sec, 1/Sec, and M (mole), respectively. The larger the ka value for a monoclonal antibody tested, the higher the binding activity of the antibody towards the antigen. The lower the Kd value, the higher the neutralizing activity the antibody has.

The human monoclonal antibodies of the present invention include human monoclonal antibodies having a ka, kd, or Kd value such as that described below:

(1) a human monoclonal antibody reactive to human oxidized LDL receptor, or a portion thereof, wherein the association rate constant (ka) between the human monoclonal antibody and the human oxidized LDL receptor is $1.0\times10^4$ (1/M·Sec) or higher, preferably $1.0\times10^5$ (1/M·Sec) or higher.

(2) a human monoclonal antibody reactive to human oxidized LDL receptor, or a portion thereof, wherein the dissociation rate constant (kd) between the human monoclonal antibody and the human oxidized LDL receptor is $1.0\times10^{-2}$ (1/Sec) or lower, preferably $1.0\times10^{-4}$ (1/Sec) or lower.

(3) a human monoclonal antibody reactive to human oxidized LDL receptor, or a portion thereof, wherein the dissociation constant (Kd) between the human monoclonal antibody and the human oxidized LDL receptor is $1.0\times10^{-2}$ (1/Sec) or lower, preferably $1.0\times10^{-7}$ (M) or lower, more preferably $1.0\times10^{-9}$ (M) or lower.

Each of the above-mentioned ka, kd, and Kd values can vary to some extent within the experimental error ranges, depending on experiment conditions, but normally, the order of values is almost unchanged.

The term "monoclonal antibody-producing cell" or "recombinant cell" producing the recombinant human monoclonal antibody of this invention refers to any cell producing the above-described human monoclonal antibody of this invention.

Specific examples include:

(1) Human monoclonal antibody-producing B cell obtainable from the above-described human antibody-producing transgenic non-human mammal produced by immunizing the animal with the above-defined immunogen (antigen).

(2) The above-described hybridoma (fused cell) prepared by fusing the human monoclonal antibody producing B cells described above with myelomas derived from a mammal.

(3) A recombinant cell that produces a recombinant human monoclonal antibody obtained by transforming a cell other than a B cell and hybridoma (e.g. Chinese hamster ovarian (CHO) cell, Baby hamster kidney (BHK) cell, and such) with genes (either the heavy chain-encoding gene or the light chain-encoding gene, or both) encoding the human monoclonal antibody isolated from the human monoclonal antibody producing B cell or hybridoma.

The recombinant human monoclonal antibody-producing recombinant cell of (3) refers to a recombinant cell producing a recombinant product of the human monoclonal antibody produced by the B cell of (1) or hybridoma of (2).

The term "pharmaceutical composition" as referred to in the present invention means (1) a composition useful as a pharmaceutical, comprising a human monoclonal antibody that binds to the human oxidized-LDL receptor, or a portion thereof, and a "pharmaceutically acceptable carrier", and (2) a composition useful as a pharmaceutical comprising a substance that inhibits the binding between an in-vivo ligand of human oxidized-LDL receptor and the oxidized-LDL receptor or the incorporation of the ligand by the oxidized-LDL receptor expressing cell as an active ingredient and a "pharmaceutically acceptable carrier".

The "pharmaceutically acceptable carrier" includes excipients, diluents, expanders, disintegrating agents, stabilizers, preservatives, buffers, emulsifiers, aromatics, colorants, sweeteners, viscosity increasing agents, flavors, dissolving agents, or other additives.

Using one or more of such carriers, a pharmaceutical composition can be formulated into tablets, pills, powders, granules, injections, solutions, capsules, troches, elixirs, suspensions, emulsions, or syrups.

The pharmaceutical composition can be administered orally or parenterally. Other forms for parenteral administration include solutions for external application, suppositories for rectal administration, and pessaries, prescribed by usual methods and comprising one or more active ingredients.

The dosage can vary depending on the age, sex, weight, and symptoms of a patient, effects of treatment, administration route, period of treatment, and the kind of active ingredient (protein or antibody mentioned above) contained in the pharmaceutical composition. Usually, the pharmaceutical composition can be administered to an adult in a dose of 10 µg to 1000 mg (or 10 µg to 500 mg) per one administration. Depending on various conditions, a lower dosage may be sufficient in some cases, and a higher dosage may be necessary in other cases.

In particular, an injection can be produced by dissolving or suspending the antibody in a non-toxic, pharmaceutically acceptable carrier, such as physiological saline or commercially available distilled water for injections, by adjusting the concentration to 0.1 µg antibody/ml carrier to 10 mg antibody/ml carrier.

The injection thus produced can be administered to a human patient in need of treatment in a dose of 1 µg to 100 mg/kg body weight, preferably 50 µg to 50 mg/kg body weight, once or more times a day. Examples of suitable, medically appropriate administration routes include intravenous injection, subcutaneous injection, intradermal injection, intramuscular injection, or intraperitoneal injection, preferably intravenous injection.

The injection can be also prepared as a non-aqueous diluent (for example, propylene glycol; polyethylene glycol; vegetable oil, such as olive oil; and alcohols, such as ethanol), suspension, or emulsion.

The injection can be sterilized by filtration with a bacteria-non-penetrable filter, by mixing a bactericide, or by irradiation. The injection can be prepared at the time of use. Namely, it is freeze-dried to make a sterile solid composition, and can be dissolved in sterile distilled water for injections, or another solvent, before use.

The pharmaceutical compositions of the present invention are useful for inhibiting the binding between oxidized LDL receptor and its in-vivo ligands (various modified LDL such as oxidized LDL, apoptotic cells, senescent erythrocytes, activated blood platelets, and such), which are involved in various clinical conditions and disease onset, and for inhibiting the oxidized LDL receptor-mediated incorporation of the ligands into cells.

In particular, since the pharmaceutical composition comprising the above-mentioned human monoclonal antibody, which is one of pharmaceutical compositions of the present invention, is derived from humans, the composition does not induce host immunorejections caused by HAMA, and thus can be used to treat or prevent the various diseases described below.

The pharmaceutical composition of the present invention is useful as an pharmaceutical to treat or prevent various diseases—for example, arteriosclerosis, thrombocytopenia, kidney disease, various types of inflammation (for example, myocardial ischemic reperfusion injury, inflammatory reactions after percutaneous transluminal coronary recanalization (PTCR) or percutaneous transluminal coronary angioplasty (PTCA)), and vessel restenosis after PTCA and PTCR caused by the interaction (binding or incorporation) of oxidized LDL receptor with its in-vivo ligands, and various diseases, such as thrombus formation in blood vessels such as arteries, and symptoms thereof, by suppressing or inhibiting the onset and/or progress of the diseases.

As used herein, the term "inflammation" refers to a fundamental local pathological reaction accompanied by infiltration of leukocytes, via rolling on and adhesion to the vascular endothelia, from the vascular flow to extravascular tissues, which is associated with damage or dysfunction of biological tissues. Inflammation is caused by various factors including, but not limited to, internal factors, or external factors, such as bacterial infection, injury, physical stimulation (for example, heat, cold, irradiation, electric stimulation, and such), or chemical substances.

Typically, inflammation can be categorized roughly into two classes—acute inflammation and chronic inflammation—based on the rates of development and progress of the symptoms. Generally, acute inflammation is characterized by relatively rapid development and rapid progress of an inflammatory reaction, followed by an explicit termination of the inflammatory reaction. On the other hand, chronic inflammation is characterized by relatively slow or gradual development, or unrecognizable development, of an inflammatory reaction that is persistent and lasts for several weeks to several years, followed by an inexplicit termination of the inflammatory reaction. As used herein, the term "inflammation" refers to both acute and chronic inflammation.

As used herein, the term "inflammation" refers to inflammation in tissues such as brain, eyes, trachea, blood vessels, lungs, liver, heart, pancreas, stomach, intestine, mesentery, kidneys, skin, nasal mucosa, and joints. Specifically, such inflammation includes, for example, encephalitis, bronchitis, vasculitis, pulmonitis, hepatitis, myocarditis, pancreatitis, enteritis, gastritis, peritonitis, nephritis (e.g., glomerular nephritis), arthritis (e.g., rheumatic arthritis), inflammation associated with postischemic reperfusion injury (e.g., myocardial ischemic reperfusion injury), inflammation caused by post-transplantation immunorejection, burns, inflammation associated with multi-organ failure, inflammation after PTCA or PTCR, and inflammation associated with arteriosclerosis.

Further, the therapeutic effects of the pharmaceutical compositions of the present invention on various disease symptoms can be tested and assessed by giving the pharmaceutical compositions (human antibodies, synthetic low-molecular-weight compounds, and such) of the present invention to known disease animal models according to conventional methods.

For example, the effect on arteriosclerosis and vascular restenosis can be evaluated using a restenosis rat model, in which pseudo-restenosis is caused by PTCA with a balloon catheter inserted into the aorta.

Further, the therapeutic effects on inflammation and tissue injury can be assessed using rat disease models in which inflammation and tissue injury (for example, lung injury) are induced by giving LPS to rats.

Further, the therapeutic effects of the human antibodies of the present invention on various kidney diseases and arteriosclerosis can be tested by giving the antibodies of the present invention to a rat model of glycerol-induced acute renal disorder, rat GBM nephritis model, rat model of angiotensin II-induced arteriosclerosis (high-blood pressure-induced arteriosclerosis model), or ApoE-knockout mouse (hyperlipidemic arteriosclerosis model).

A DNA encoding the human oxidized-LDL receptor used in the present invention can be prepared by conventional methods, such as cloning cDNA from mRNA encoding the human oxidized-LDL receptor, isolating genomic DNA and splicing it, conducting PCR using the cDNA or mRNA sequence as a template, chemical synthesis, and so on.

A DNA encoding the human oxidized-LDL receptor of this invention can be prepared by cleaving (digesting) each DNA encoding the human oxidized-LDL receptor as prepared above with an appropriate restriction enzyme, and ligating the obtained DNA fragments, in combination with a linker DNA or Tag if necessary, using an appropriate DNA polymerase and such.

cDNA encoding the human oxidized-LDL receptor (hereinafter referred to as the desired protein) can be cloned from mRNA by, for example, the method described below.

First, the mRNA encoding the desired protein is prepared from tissues or cells expressing and producing the desired protein. mRNA can be prepared by isolating total RNA by a known method, such as the guanidine-thiocyanate method (Biochemistry, Vol. 18, p 5294, 1979), the hot phenol method, or the AGPC method, and subjecting it to affinity chromatography using oligo-dT cellulose or poly-U Sepharose.

Then, using the mRNA obtained as a template, cDNAs are synthesized, for example, by well-known methods using reverse transcriptase, such as the method by Okayama et al. (Mol. Cell. Biol. Vol. 2, p. 161 (1982); ibid. Vol. 3, p. 280 (1983)) or the method by Hoffman et al. (Gene Vol. 25, p. 263 (1983)), and converted into double-stranded cDNAs. A cDNA library is prepared by transforming *E. coli* with plasmid vectors, phage vectors, or cosmid vectors having those cDNAs or by transfecting *E. coli* after in vitro packaging.

The plasmid vectors used in this invention are not limited so long as they may be replicated and maintained in hosts. Any phage vector that can be replicated in hosts can also be used. Examples of the cloning vectors typically used include pUC19, λgt10, λgt11, and so on. When the vector is applied to immunological screening, as mentioned below, a vector having a promoter that enables the expression of a gene encoding the desired protein in a host is preferably used.

cDNA can be inserted into a plasmid according to, for example, the method by Maniatis et al. (Molecular Cloning, A Laboratory Manual, second edition, Cold Spring Harbor Laboratory, p. 1.53, 1989). cDNA can be inserted into a phage vector according to, for example, the method by Hyunh et al. (DNA cloning, a practical approach, Vol. 1, p. 49 (1985)). These methods can be easily performed using a commercially available cloning kit (for example, a product from TAKARA). The recombinant plasmid or phage vector thus obtained is introduced into an appropriate host cell, such as a prokaryote (for example, *E. coli*: HB101, DH5α, Y1090, DH10B, MC1061/P3, etc).

Examples of methods for introducing a plasmid into a host are, the calcium chloride method, the calcium chloride/rubidium chloride method, and the electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from STRATAGENE or AMERSHAM).

The cDNA encoding the desired protein can be isolated from the cDNA library prepared according to the method mentioned above by combining general cDNA screening methods.

For example, a clone comprising the desired cDNA can be screened by a known colony hybridization method (Cranstein et al. Proc. Natl. Acad. Sci. USA, Vol. 72, p. 3961 (1975)) or plaque hybridization method (Molecular Cloning, A Laboratory Manual, second edition, Cold Spring Harbor Laboratory, p. 2.108 (1989)), using $^{32}$P-labeled chemically synthesized oligonucleotides as probes, which correspond to the amino acid sequence of the desired protein. Alternatively, a clone having a DNA fragment encoding a specific region within the desired protein can be screened by amplifying the region by PCR with synthetic PCR primers.

When utilizing a cDNA library prepared using a cDNA expression vector (for example, λgt11 phage vector), the desired clone can be screened by an antigen-antibody reaction using an antibody against the desired protein. A screening method using the PCR method is preferably used when many clones are subjected to screening.

The nucleotide sequence of the obtained DNA can be determined by the Maxam-Gilbert method (Maxam et al. Proc. Natl. Acad. Sci. USA, Vol. 74, p. 560 (1977)) or the dideoxynucleotide synthetic chain termination method using phage M13 (Sanger et al. Proc. Natl. Acad. Sci. USA, Vol. 74, pp. 5463-5467 (1977)). The whole or a part of the gene encoding the desired protein can be obtained by excising the clone obtained as mentioned above with restriction enzymes and so on.

Additionally, the DNA encoding the desired protein can be isolated from the genomic DNA derived from cells mentioned above expressing the desired protein using the following methods.

Such cells are solubilized preferably by SDS or proteinase K, and the DNAs are deproteinized by repeating phenol extraction. RNAs are digested preferably with ribonuclease. The DNAs obtained are partially digested with appropriate restriction enzymes, and the obtained DNA fragments are amplified with an appropriate phage or cosmid to generate a library. Then, clones having the desired sequence are detected, for example, by radioactively labeled DNA probes, and the whole or a portion of the gene encoding the desired protein is obtained from the clones by excision with restriction enzymes, etc.

A DNA encoding a desired protein can be prepared by conventional FCR methods, using known mRNA or cDNA of the desired protein as a template (Gene Amplification PCR method, Basics and Novel Development, Kyoritsu Publishers, 1992, etc).

A DNA encoding a desired protein can also be produced by chemical synthesis, according to usual methods, based on the nucleotide sequence encoding the protein.

The human oxidized-LDL receptor of the present invention or a portion thereof (preferably, extracellular domain) can be prepared as a recombinant protein according to conventional recombinant technology, using DNA obtained by digesting the human oxidized-LDL receptor-encoding DNA (the cDNA or the genomic DNA comprising introns) prepared by the method indicated above with appropriate restriction enzymes and ligating the resulting DNA fragment(s) encoding the human oxidized-LDL receptor, according to need, with a linker DNA or Tag using an appropriate DNA polymerase or other enzymes.

Specifically, the preparation of the protein is described as follows: the DNA construct as prepared above is inserted into a vector, described below in detail, to obtain an expression vector; a host cell, which will be described hereinafter, is transformed with the expression vector to obtain a transformant; the resulting transformant cells are cultured for the production and accumulation of the desired protein in the culture supernatant; the protein accumulated in the culture supernatant can be purified easily by using column chromatography, etc.

The expression vector used for producing the recombinant human oxidized-LDL receptor (or extracellular domain thereof) is not particularly limited so long as it can be retained by replication or self-multiplication in various prokaryotic and/or eukaryotic host cells, including plasmid vectors and phage vectors (Cloning Vectors: A laboratory Manual, Elsevier, N.Y., 1985).

The expression vector can be easily prepared by ligating, according to conventional methods, a DNA encoding the human oxidized-LDL receptor (or extracellular domain) with a recombination vector available in the art (plasmid DNA and bacteriophage DNA). Specific examples of the vectors for recombination include *E. coli*-derived plasmids such as pBR322, pBR325, pUC12, pUC13, and pUC19; yeast-derived plasmids, such as pSH19 and pSH15; and *Bacillus subtilis*-derived plasmids, such as pUB110, pTP5, and pC194. Examples of phages are bacteriophages, such as λ phage; and an animal or insect virus (pVL1393, Invitrogen), such as a retrovirus, vaccinia virus, and nuclear polyhedrosis virus.

A plasmid vector is useful for expressing the DNA encoding the human oxidized-LDL receptor of this invention or its soluble extracellular domain, for expressing the human oxidized-LDL receptor on host cell surface, and for producing the soluble extracellular domain of the human oxidized-LDL receptor. The plasmid vector is not limited so long as it expresses a gene encoding the human oxidized-LDL receptor or its soluble extracellular domain in various prokaryotic and/or eukaryotic host cells and produces the polypeptide. Examples thereof include pMAL C2, pcDNA3.1(–), pEF-BOS (Nucleic Acids Res. Vol. 18, p. 5322 (1990) and so on), pME18S (Experimental Medicine: SUPPLEMENT, "Handbook of Genetic Engineering" (1992) and so on), etc.

When bacteria, particularly *E. coli* are used as host cells, an expression vector generally comprises, at least, a promoter/operator region, an initiation codon, a DNA encoding the protein of the present invention, a termination codon, a terminator region, and a replicon.

When yeast, animal cells, or insect cells are used as hosts, an expression vector preferably comprises, at least, a promoter, an initiation codon, a DNA encoding the human oxidized-LDL receptor (or its extracellular domain) of the present invention, and a termination codon. It may also comprise a DNA encoding a signal peptide, enhancer sequence, 5'- and 3'-untranslated regions of the gene encoding the human oxidized-LDL receptor of the present invention, splicing junctions, polyadenylation site, selectable marker region, and replicon. The expression vector may also contain, if necessary, a gene for gene amplification (marker) that is usually used according to purposes.

A promoter/operator region to express the human oxidized-LDL receptor (or its extracellular domain) of the present invention in bacteria comprises a promoter, an operator, and a Shine-Dalgarno (SD) sequence (for example, AAGG). For example, when the host belongs to the genus *Escherichia*, it preferably comprises the Trp promoter, the lac promoter, the recA promoter, the λPL promoter, the lpp promoter, the tac promoter, or the like.

Examples of suitable promoters for expressing the human oxidized-LDL receptor (or its extracellular domain) of the present invention in yeast include the PH05 promoter, the PGK promoter, the GAP promoter, the ADH promoter, and so on. When the host belongs to the genus *Bacillus*, examples thereof are the SL01 promoter, the SP02 promoter, the penP promoter, and so on.

When the host is a eukaryotic cell, such as mammalian cell, examples of suitable promoters therefore include SV40-derived promoters, retrovirus promoters, heat shock promoters, and so on. As a matter of course, the promoter is not limited to the above examples. In addition, the use of an enhancer is also effective for the expression.

A preferable initiation codon is, for example, a methionine codon (ATG).

A commonly used termination codon (for example, TAG, TAA, TGA) is exemplified as a termination codon.

Usually, conventional natural or synthetic terminators are used as a terminator region.

A replicon is a DNA that is capable of replicating the whole DNA sequence in host cells, and includes natural plasmids, artificially modified plasmids (DNA fragments prepared from natural plasmids), synthetic plasmids, and so on. Examples of preferable plasmids are pBR322 or its artificial derivatives (DNA fragments prepared by treating pBR322 with appropriate restriction enzymes) for *E. coli*; yeast 2μ plasmid or yeast chromosomal DNA for yeast; and pRSVneo ATCC 37198, pSV2dhfr ATCC 37145, pdBPV-MMTneo ATCC 37224, pSV2neo ATCC 37149, pSV2bsr, and such for mammalian cells.

As the enhancer sequence, polyadenylation site, and splicing junction, those that are routinely used in the art, such as those derived from SV40, can be used.

Usually available selectable markers can be used according to conventional methods. Examples thereof include resistance genes for antibiotics, such as tetracycline, ampicillin, or kanamycin.

Examples of genes suitable for gene amplification include the dihydrofolate reductase DHFR) gene, the thymidine kinase gene, the neomycin resistance gene, the glutamate synthase gene, the adenosine deaminase gene, the ornithine decarboxylase gene, the hygromycin-B-phosphotransferase gene, the aspartate transcarbamylase gene, etc.

The expression vector of the present invention can be prepared by contiguously and circularly ligating at least the above-mentioned promoter, initiation codon, DNA encoding the protein of the present invention, termination codon, and terminator region, to an appropriate replicon. If desired, appropriate DNA fragments (for example, linkers and other restriction sites) can be used by conventional methods, such as digestion with a restriction enzyme or ligation using T4 DNA ligase.

Transformants of the present invention can be prepared by introducing the expression vector mentioned above into host cells.

Host cells used in the present invention are not limited so long as they are compatible with the expression vector mentioned above and can be transformed. Examples thereof include various cells, such as wild-type cells or artificially established recombinant cells available in the technical field of the present invention (for example, bacteria (*Escherichia* and *Bacillus*), yeast (Saccharomyces, *Pichia*, and such), animal cells, or insect cells).

*E. coli* or animal cells are preferably used. Specific examples are *E. coli* (DH5α, DH10B, TB1, HB101, XL-2Blue, and such); mouse-derived cells (COP, L, C127, Sp2/0, NS-1, NIH 3T3, and such); rat-derived cells, hamster-derived cells (BHK, CHO, and such); monkey-derived cells (COS1, COS3, COS7, CV1, Velo, and such); and human-derived cells (Hela, diploid fibroblast-derived cells, myeloma, Namalwa, and such).

An expression vector can be introduced (transformed (transduced)) into host cells by known methods.

Transformation can be performed, for example, according to the method by Cohen et al. (Proc. Natl. Acad. Sci. USA, Vol. 69, p. 2110 (1972)), the protoplast method (Mol. Gen. Genet., Vol. 168, p. 111 (1979)), or the competent method (J. Mol. Biol., Vol. 56, p. 209 (1971)) when the hosts are bacteria (*E. coli, Bacillus subtilis*, and such); the method by Hinnen et al. (Proc. Natl. Acad. Sci. USA, Vol. 75, p. 1927 (1978)), or the lithium method (J. Bacteriol, Vol. 153, p. 163 (1983)) when the host is *Saccharomyces cerevisiae*; the method by Graham (Virology, Vol. 52, p. 456 (1973)) when the hosts are animal cells; and the method by Summers et al. (Mol. Cell. Biol., Vol. 3, pp. 2156-2165 (1983)) when the hosts are insect cells.

An extracellular domain of the human oxidized-LDL receptors (soluble human oxidized-LDL receptors) of the present invention can be produced by cultivating transformants (hereinafter, the term includes "transductants") comprising an expression vector prepared as mentioned above in nutrient media.

The nutrient media preferably comprises a carbon source, an inorganic nitrogen source, or an organic nitrogen source necessary for the growth of host cells (transformants). Examples of suitable carbon sources include glucose, dextran, soluble starch, and sucrose; and examples of suitable inorganic or organic nitrogen sources include ammonium salts, nitrates, amino acids, corn steep liquor, peptone, casein, meet extract, soybean cake, and potato extract. If desired, the media may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on)).

Cultivation is performed by methods known in the art. Cultivation conditions, such as temperature, pH of the media, and cultivation time, may be appropriately selected so that the protein of the present invention is produced in large quantities.

Specific media and cultivation conditions depend on the particular host cells. Examples are illustrated below, but the invention is not restricted thereto.

When the hosts are bacteria, actinomycetes, yeasts, or filamentous fungi, a liquid media comprising an above-mentioned nutrient source is appropriate. A medium with pH 5 to 8 is preferably used.

When the host is *E. coli*, examples of preferable media include LB media, M9 media (Miller et al. Exp Mol. Genet. Cold Spring Harbor Laboratory, p. 431 (1972)), YT medium, and so on. Using these media, cultivation can usually be performed at 14 to 43° C for about 3 to 24 hours with aeration and stirring, if necessary.

When the host is *Bacillus*, cultivation can be performed usually at 30 to 40° C. for about 16 to 96 hours with aeration and stirring, if necessary.

When the host is yeast, an example of a suitable media is Burkholder minimal media (Bostian, Proc. Natl. Acad. Sci. USA, Vol. 77, p. 4505 (1980)). The pH of the media is preferably 5 to 8, Cultivation can usually be performed at 20 to 35° C for about 14 to 144 hours with aeration and stirring, if necessary.

When the host is an animal cell, examples of media include MEM media containing about 5 to 20% fetal bovine serum (Science, Vol. 122, p. 501 (1952)), DMEM media (Virology, Vol. 8, p. 396 (1959)), RPMI1640 media (J. Am. Med. Assoc., Vol. 199, p. 519 (1967)), 199 media (Proc. Soc. Exp. Biol. Med., Vol. 73, p. 1 (1950)), HamF12 media, and so on. The pH of the media is preferably about 6 to 8. Cultivation can usually be performed at about 30 to 40° C for about 15 to 72 hours with aeration and stirring, if necessary.

When the host is an insect cell, an example of a suitable media is Grace's media containing fetal bovine serum (Proc. Natl. Acad. Sci. USA, Vol. 82, p. 8404 (1985)). The pH thereof is preferably about 5 to 8. Cultivation can usually be performed at about 20 to 40° C. for 15 to 100 hours with aeration and stirring, if necessary.

An extracellular domain of the human oxidized-LDL receptor (soluble human oxidized-LDL receptor) of the present invention can be produced by cultivating transformants as mentioned above (in particular animal cells or *E. coli*) and allowing them to secrete the protein into the culture supernatant. Namely, a culture filtrate (supernatant) is obtained by methods, such as filtration or centrifugation of the obtained culture, and the desired protein is purified and isolated from the culture filtrate by methods commonly used in order to purify and isolate natural or synthetic proteins.

Examples of suitable isolation and purification methods include methods utilizing affinity, such as affinity column chromatography; methods utilizing solubility, such as salting out and solvent precipitation method; methods utilizing the difference in molecular weight, such as dialysis, ultrafiltration, gel filtration, and sodium dodecyl sulfate-polyacrylamide gel electrophoresis; methods utilizing charges, such as ion exchange chromatography and hydroxylapatite chromatography; methods utilizing the difference in hydrophobicity, such as reverse phase high performance liquid chromatography; and methods utilizing the difference in isoelectric points, such as isoelectric focusing.

When the desired protein exists in the periplasm or cytoplasm of cultured transformants, the cells are first harvested by usual methods, such as filtration or centrifugation, and are suspended in an appropriate buffer. After the cell wall and/or cell membrane and such are disrupted by methods such as lysis with sonication, lysozymes, or freeze thawing, the membrane fraction comprising the desired protein is obtained by methods such as centrifugation and filtration The membrane fraction is solubilized with a detergent, such as Triton-X100, to obtain the crude extract. Finally, the protein is isolated and purified from the crude extract by usual methods such as those illustrated above.

The present invention is specifically illustrated below with reference to Examples, but it is not to be construed as being limited thereto.

In the Examples described below, the term "oxidized LDL receptor" is also referred to as "LOX-1".

EXAMPLE 1

Preparation of Various Recombinant LOX-1

<1-1> Preparation of Soluble Bovine LOX-1 (Bovine LOX-Fc)

A cDNA (SEQ ID NO: 3) encoding bovine oxidized LDL receptor LOX-1 (bLOX-1) was prepared according to the same method as described in previous reports (Nature, Vol. 386, p. 73-77, 1997; Unexamined Published Japanese Patent Application (JP-A) Hei 9-98787).

The obtained cDNA was amplified by PCR using a pair of primers (5'-GGGGATCCTGATCTCATGCAG-3' (SEQ ID NO: 5) and 5'-GCGGATCCTGTGCTCTCAATAGAT-TCGC-3' (SEQ ID NO: 6) The prepared cDNA fragment comprises cDNA encoding the extracellular region of bovine LOX-1 (nucleotide No. 215 to 844 in SEQ ID NO: 3) in which both ends comprise a BamHI site.

The plasmid pCd51neg1 (see DNA and Cell Biol., Vol. 9, p. 347-353, 1990; a generous gift from Dr. B. Seed at the Massachusetts General Hospital) (SEQ ID NO: 7) comprising genomic DNA containing exons encoding the hinge region of human IgG1, Cγ12 and Cγ13, was linearized by BamHI digestion.

The cDNA encoding the extracellular region of bovine LOX-1 obtained by the procedure as described above was ligated to the linearized plasmid at the BamHI site (169th nucleotide in SEQ ID NO: 7) with T4 DNA ligase to construct the plasmid pBLOX-Fc.

CHO-K1 cells cultured to become a sub-confluent monolayer in HamF12 medium containing 10% FBS (fetal bovine serum) were co-transfected with pBLOX-Fc (1 μg) and expression plasmid vector pSVbsr (10 ng; Funakoshi; containing bsr (blasticidin S-resistance) gene and viral promoter derived from SV40) using lipofectamine (GIBCO).

After the cells were cultured for 48 hours, the medium was changed with HamF12 medium containing blasticidin-S (10

μg/ml, Funakoshi). The cells were further cultured to select and obtain transformants containing both pBLOX-Fc and pSVbsr.

The resulting transformants were maintained in Ham F 12 medium containing 10% FCS (fetal calf serum) and blasticidin-S (10 μg/ml, Funakoshi).

In order to purify bLOX-1-Fc, the transformed CHO-K1 cells were cultured to be confluent in a HamF12 medium containing blasticidin-S (10 μg/ml, Funakoshi), and after the medium was changed to CHO-SFM-II (GIBCO/BRL), the cells were further cultured for 3 days. This step was repeated several times, and then, 800 ml of culture supernatant was collected. bLOX-Fc was purified from the culture supernatant using the Affi-Gel Protein A MAPS-II kit (Bio-Rad) by the following procedure.

The culture supernatant was loaded onto a Protein A-agarose gel column pre-equilibrated with a binding buffer. Then, the column was washed with the binding buffer (15 bed volume), and eluted with an elution buffer (5 bed volume) The elute was recovered and dialyzed against a phosphate buffer. The outer dialysate was changed twice or more. The resulting purified bLOX-Fc was concentrated by ultrafiltration with Centriprep (Amicon). The concentration of purified bLOX-Fc was determined to be 866 μg/ml using BCA protein assay kit (PIERCE).

In addition, the above-described purified bLOX-Fc was confirmed by Western blotting as follows.

The purified bLOX-Fc was electrophoresed on a 12.5% SDS agarose gel (Daiichi Pure Chemicals). After electrophoresis, the sample was transferred onto an Immobilon membrane (Millipore). The membrane was incubated in Block Ace (Snow Bland) overnight for blocking, and then incubated with biotin-labeled goat anti-human IgG antibody as a primary antibody. The membrane was then treated with an ABC kit (Vector), and the band was visualized using the Konica Immunostain kit.

Further, in the same way as described above, bLOX-Fc was also prepared from recombinant cells derived from host cells, the monkey kidney cell line COS7.

<1-2> Preparation of Bovine LOX-1 Using CHO Cells

Recombinant CHO cells (Chinese Hamster Ovarian cell) expressing bovine LOX-1 (amino acid sequence: SEQ ID NO: 4, GenBank Accession No. BAA19005; nucleotide sequence: SEQ ID NO: 3, GenBank Accession No. D89049) were prepared by the same method as described in the report by Sawamura (Nature, Vol. 386, p. 73-77, 1997).

<1-3> Preparation of Mouse Anti-Bovine LOX-1 Monoclonal Antibody

A cell membrane fraction was prepared as an antigen from CHO cells expressing bovine LOX-1, which had been prepared as described above. The fraction was prepared by the same procedure used to prepare the antigen (a cell membrane fraction of recombinant CHO cell expressing human LOX-1) in the preparation of human anti-human oxidized LDL receptor monoclonal antibody described hereinafter.

Normal mice were immunized with the obtained cell membrane fraction according to the same method as used to prepare human anti-human LOX-1 monoclonal antibody as described hereinafter. Thus, mouse anti-bovine LOX-1 monoclonal antibodies (also having cross-reactivity to human LOX-1) were prepared.

<1-4> Preparation of Soluble Human LOX-1 (Human LOX-FC; hLOX-Fc)

A cDNA (SEQ ID NO: 1) encoding the entire human LOX-1 was prepared by PCR according to a conventional method.

Specifically, the cDNA was synthesized by PCR according to the conventional method using, as a template, single-stranded DNA prepared from commercially available human placental mRNA (Clontech; Cat. No. #6501) with reverse transcriptase and using primers designed based on the full-length human LOX-1 cDNA (Nature, Vol. 386, p. 73-77, 1997; JP-A Hei 9-98787).

Primers, 5'-ATGACTTTTGATGACCTGATCCAG-3' (SEQ ID NO: 8) and 5'-CACTGTGCTCTTAGGTTTGC-CTTC-3' (SEQ ID NO: 9), were used.

PCR was carried out as follows: 1 cycle (at 94° C for 2 minutes); 30 cycles (at 94° C for 30 seconds, at 65° C for 30 seconds, and at 72° C for 90 seconds); and 1 cycle (at 72° C for 7 minutes).

DNA polymerase used was commercially available KOD DNA polymerase (TOYOBO).

The resulting PCR products were subjected to agarose gel electrophoresis (Qiaquick PCR Purification Kit; Quiagen). The cDNA fragment was excised from the gel, and inserted into a plasmid according to the conventional method. The cDNA fragment was used as a probe in the hybridization assay described hereinafter. cDNA was prepared based on the above-mentioned human mRNA using a commercially available cDNA preparation kit (SuperScript Lambda System; Gibco BRL). The resulting cDNA was ligated to commercially available lambda arms (λ ZipLox; Gibco BRL) and then in-vitro packaged using commercially available Giga-Pack Gold (Amersham). Using the resulting lambda phage particles, a cDNA library comprising phage plaques containing recombinant phages was prepared using Y1090 as host cells.

The cDNA library was plated on a agar plate ($4 \times 10^4$ plaques/plate) and then a replica was prepared by transferring the plaques onto a nylon membrane (Hybond N+, Amersham). The human LOX-1 cDNA fragment obtained as described above was labeled with p.32P]dCTP (Quickprime; Pharmacia) to prepare a probe solution for plaque hybridization. First and second screening of the replica was carried out using the probe solution, and thus a number of positive clones were obtained. After isolation of the respective clones as a single plaque, the phage DNAs were treated by in-vivo excision according to the instruction manual provided by GIBCO-BRL, and then the DNAs were recovered as plasmid DNAs (plasmid: M13K07; Gibco BRL).

Then, the nucleotide sequence of human LOX-1 cDNA inserted in each clone was determined using a commercially available kit (Dye Primer Cycle Sequencing FS Core Kit; Perkin Elmer Applied Biosystems) and a sequencer (ABI Prism 373A; Perkin Elmer Applied Biosystems). According to the sequencing results, the obtained cDNAs were confirmed to encode the entire human LOX-1.

A chimeric protein (hLOX-Fc) comprising the soluble region of human LOX-1 ($65^{th}$ to $273^{rd}$ amino acid region) and human IgG-Fc was prepared from recombinant cells derived from monkey kidney cell line COS7 as a host with the isolated human cDNA in the same way as in Example <1-1>.

<1-5> Preparation of Recombinant Human LOX-1 Using CHO Cells

After the full-length human LOX-1-encoding cDNA, which had been obtained in Example <1-2>, was inserted into the vector pEF-NEO, the recombinant expression vector was introduced into Chinese hamster ovarian cells (CHO cell) by electroporation (960° F., 320 V) according to the conventional method. The cells were cultured in RPMI1640 medium containing geneticin (0.8 mg/ml; Gibco BRL) and 10% FCS to select drug-resistant transformants. Further, cells were selected when they exhibited significant values in ELISA and DiI-labeled oxidized LDL incorporation assay carried out using anti-bovine LOX-1 monoclonal antibodies exhibiting cross-reactivity to human LOX-1 prepared as described above by the same procedure as described in the following Examples. The selected cells were cloned by the limiting dilution method. Total RNA was extracted from the obtained CHO cells expressing human LOX-1 using ISOGEN (Nippon Gene). Then, the cells were confirmed to contain the introduced full-length human LOX-1 cDNA by RT-PCR and restriction enzyme mapping according to the conventional method.

<1-6> Preparation of Recombinant LOX-1 Derived from Various Non-Human Mammals Using CHO Cells Recombinant CHO cells expressing each of pig, rabbit, or rat LOX-1 were prepared by the same procedure as described in the above Example according to the report of Sawamura et al. (Nature, Vol. 386, p. 73-77, 1997)

Rabbit LOX-1
  Amino acid sequence: SEQ ID NO: 10, GenBank Accession No. BAA81912
  Nucleotide sequence: SEQ ID NO: 11, GenBank Accession No. AB016237
Pig LOX-1
  Amino acid sequence; SEQ ID NO: 12, GenBank Accession No. BAA88894
  Nucleotide sequence: SEQ ID NO: 13, GenBank Accession No. AB018668
Rat LOX-1:
  Amino acid sequence: SEQ ID NO: 14, GenBank Accession No. BAA25785
  Nucleotide sequence: SEQ ID NO: 15, GenBank Accession No. AB005900

<1-7> Preparation of FLAG-Attached Soluble Human LOX-1

A cDNA encoding the extracellular region of human LOX-1 ($65^{th}$ to $273^{rd}$ amino acid region) was prepared by PCR using the full-length cDNA as a template and using a pair of primers designed based on the cDNA sequence encoding the full-length human LOX-1. The resulting CDNA was inserted into a commercially available expression vector, pFLAGCMV-1 (Kodak).

As used herein, the term "FLAG" refers to a peptide sequence tag that is attached to the N terminus of a protein encoded by a gene of interest to be inserted into a vector. Specifically, FLAG is attached to the N terminus of a recombinant protein of interest, which is obtained by culturing transformants prepared through transformation with a recombinant protein expression vector constructed by inserting the gene of interest into a plasmid. Thus, the recombinant protein prepared in this Example is a soluble human LOX-1 recombinant protein containing a FLAG peptide at the N terminus.

pFLAGCMV, in which the cDNA encoding the extracellular region of human LOX-1 obtained as described above had been inserted, was introduced into cells of monkey kidney cell line COS7 by electroporation (960 µF, 300 V) according to the conventional method. The cells were cultured in FCS-coated culture dishes containing serum-free ASF104 medium (Ajinomoto), and then the culture supernatant was recovered.

The recovered culture supernatant was loaded onto a column filled with anti-FLAG antibody affinity gel (Kodak). After the column was washed with TBS, elution was carried out with 0.1 M glycine-HCl (pH 3.0; 0.9 ml/fraction). Immediately after elution, the eluate was neutralized with 1 M Tris-HCl (pH 9.0). The recovered elution fractions were subjected to SDS-gel electrophoresis to identify fractions containing FLAG-attached soluble human LOX-1 protein (FLAG-hLOX-1).

After the fractions containing FLAG-hLOX-1 were dialyzed against phosphate buffer (0.22-µm filtration), absorbance (O.D. 280) of the resulting purified FLAG-hLOX-1 was measured to estimate the amount of protein.

<1-8> Preparation of FLAG-Attached Soluble Bovine LOX-1

FLAG-bLOX-1 containing a FLAG peptide at the N terminus of the extracellular region of bovine oxidized LDL receptor (amino acid No: 61-270) was prepared by the same procedure as described above.

EXAMPLE 2

Preparation of Antigens

The human LOX-1-expressing CHO cells prepared as described above were treated with 5 mM EDTA-PBS (at room temperature for 5 minutes), and then were suspended in a buffer containing protease inhibitors (25 mM HEPES (pH 7.4), 10 mM $MgCl_2$, 0.25 M sucrose, and protease inhibitor (containing 10 U/ml aprotinine, 2 µg/ml pepstatin, 50 µg/ml leupeptin, and 0.35 mg/ml PMSF)). The cells were homogenized with a Potter homogenizer, and centrifuged at a low speed (at 1,500 rpm for 10 minutes at 4° C). Then, the Supernatant was recovered and ultracentrifuged at 100,000 g for 1 hour at 4° C. The precipitated membrane fraction was collected, and then suspended in phosphate buffer. The resulting suspension was stored at −20° C. The suspension was used as an antigen (immunogen) in preparing human antibodies of the present invention described hereinafter.

EXAMPLE 3

Preparation of Human Anti-Human Oxidized LDL Receptor Monoclonal Antibodies

The monoclonal antibodies prepared in this Example were prepared according to a typical method as described in "JIKKEN IGAKU (supplement); Handbook for Cell Engineering, (T. Kuroki et al. eds., Yodosha Co., pp 66-74, 1992)", "Introductory Manual for Monoclonal Antibody Experiments (T. Ando et al., Kodansha, 1991)", etc.

Human oxidized LDL receptor used as the immunogen was the membrane fraction prepared from human LOX-1-expressing CHO cells prepared as described above.

The human antibody-producing transgenic mouse, which had been created by the above-mentioned method, was used as the animal to be immunized (Nature Genetics, Vol. 7, p. 13-21, 1994; Nature Genetics, Vol. 15, p. 146-156, 1997; Published Japanese Translation of International Publication No. Hei 4-504365; Published Japanese Translation of International Publication No. Hei 7-509137; Nikkei Science, June issue, pp. 40-50, 1995, and such).

Cell culture was carried out using multi-well microplates.

<3-1> Preparation of Hybridomas Producing Human Anti-Human Oxidized LDL Receptor Monoclonal Antibodies An equal volume of Freund's complete adjuvant (ICN/CAPPEL) was combined with the membrane fraction of human LOX-1-expressing CHO cells prepared as described above. For primary immunization (day 0), the mixture was injected into the footpads of the above-mentioned human antibody-producing transgenic mice. The membrane fraction alone, which was derived from human LOX-1-expressing CHO cells, was injected to the mouse footpads every week after the primary immunization as a booster, five times or more in total. Further, the final immunization was carried out with the same cell membrane fraction alone by the same procedure two days before the collection of lymph node cells described hereinafter.

Two days after the final immunization, lymph nodes were collected from the below-knee region, inguinal region, and iliac bone of each mouse. The obtained lymph node cells were fused with mouse myeloma P3/X63-AG8.653 cells (ATCC No: CRL-1580) by mixing them at a ratio of 5:1 and using polyethylene glycol 1500 (Boehringer-Manheim) as a fusing agent. Many hybridomas were obtained by drug selection in an Excel301 medium containing HAT (Sigma) and 10% FCS.

<3-2> Screening of Hybridomas Producing Monoclonal Antibodies by ELISA

Hybridomas producing human monoclonal antibodies against human oxidized LDL receptor were obtained by screening the hybridomas prepared as described above by ELISA as described below.

<3-2-1> ELISA (Part 1)

COS7 cells expressing soluble recombinant human LOX-Fc chimera protein prepared as described above were cultured, and then the soluble recombinant human LOX-FC chimera protein (hLOX-Fc) was purified from the collected culture supernatant using a Protein A column (Pharmacia).

hLOX-Fc (50 µl/well; 4 Ag/ml in PBS) was added to each well of 96-well ELISA microtiter plates (Coaster), and the plates were incubated at 37° C for one hour to allow the microtiter plate to adsorb hLOX-Fc.

Then, the supernatant was discarded, and a blocking reagent (200 µl; commercially available Block-Ace (commercial name)) was added to each well. The plates were incubated at room temperature for two hours to block hLOX-Fc-uncoated spaces of the well surface. Each well was washed twice with a phosphate buffer containing 0.1% Tween 20. Thus, microtiter plates where each well had been coated with hLOX-Fc was prepared.

The supernatant of each hybridoma culture (50 µl) was added to each well, and the plates were incubated for one hour. Then, each well was washed three times with the phosphate buffer containing 0.1% Tween20.

Then, to detect the heavy chain of human immunoglobulin (human monoclonal antibody) in the supernatant of the hybridoma, peroxidase-labeled goat anti-human immunoglobulin (Fc) antibody (50 µl of 7,000-fold dilute; American Corex) was added to each well and the plate was incubated at room temperature for 30 minutes.

On the other hand, to detect the light chain of human immunoglobulin (human monoclonal antibody) in the supernatant of the hybridoma, peroxidase-conjugated goat anti-human immunoglobulin κ chain antibody (50 µl of 3,000-fold dilute) was added to each well and the plate was incubated at room temperature for 30 minutes.

After the microtiter plates were washed three times with phosphate buffer containing 0.1% Tween20, 100 µl of tetramethylbenzidine (3,3',5,5'-tetramethylbenzidine (TMB); BIO-RAD) was added to each well and the plates were incubated at room temperature for 30 minutes.

Then, 25 µl of 0.5 M $H_2SO_4$ was added to each well to stop the reaction. The absorbance at a wavelength of 450 nm was measured with Model 3550 Microplate Reader (Bio-Rad).

Thus, a number of hybridomas producing human anti-human oxidized LDL receptor monoclonal antibodies were selected.

A negative control experiment was carried out by the same procedure as described above, except without adding the hybridoma supernatant.

Figure 1:
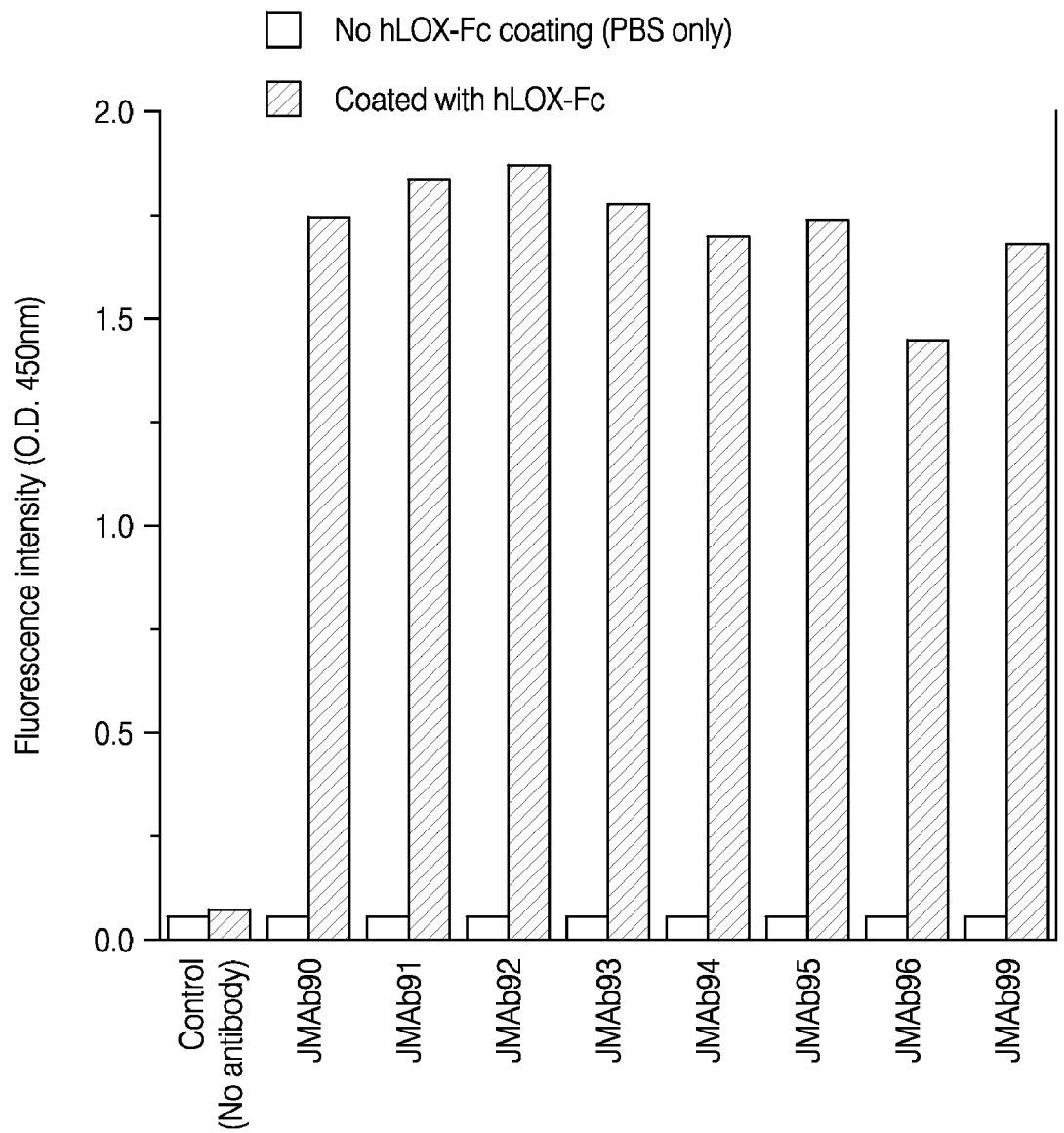
FIG. 1 is a diagram showing the reactivity (binding activity) of human anti-human LOX-1 monoclonal antibodies to human LOX-1, which was analyzed by ELISA using human LOX-Fc chimeric protein.

The results are shown in FIG. 1.

All of the human anti-human LOX-1 monoclonal antibodies produced by the hybridomas significantly bound to (had affinity for) soluble recombinant human LOX-1.

<3-2-2> ELISA (Part 2; Cell ELISA)

The human oxidized LDL receptor-expressing CHO cells ($1 \times 10^4$ cells/well) prepared as described above were plated in each well of a 96-well ELISA microtiter plate, and then were incubated at 37° C for 2 days.

Next, the supernatant was discarded, and the culture supernatant (50 µl/well) of each hybridoma was added to each well. After the plate was incubated for one hour, each well was washed twice with ASF104 medium (Ajinomoto) without FCS.

Then, to detect the heavy chain of human immunoglobulin (human monoclonal antibody) in the supernatant of the hybridoma, peroxidase-conjugated goat anti-human immunoglobulin (Fc) antibody (50 µl of 7,000-fold dilute in ASF104 medium containing 0.5% BSA; American Corex) was added to each well. The plate was incubated at room temperature for 30 minutes.

After the microtiter plate was washed twice with ASF104 medium without FCS, 100 µl of tetramethylbenzidine (3,3', 5,5'-tetramethylbenz-idine (TMB); BIO-RAD) was added to each well and the plate was incubated at room temperature for 30 minutes.

Then, 25 µl of 0.5 M $H_2SO_4$ was added to each well to stop the reaction. The absorbance at a wavelength of 450 nm was measured with Model 3550 Microplate Reader (Bio-Rad).

As a result, a number of hybridomas producing human anti-human oxidized LDL receptor monoclonal antibody were selected.

In the same way as described above, a control experiment was carried out using a microplate, except for adding bovine oxidized LDL receptor-expressing CHO cells, prepared as described above, instead of human oxidized LDL receptor-expressing CHO cells to each well.

As a negative control experiment, a microtiter plate containing no recombinant CHO cells was treated by the same procedure as described above.

In addition, a test was carried out in the same way as described above, using as a negative control antibody a human anti-KLH monoclonal antibody prepared by immunizing the above-mentioned transgenic mouse producing human antibody with KLH (keyhole limpet hemocyanin; PIERCE) by the same procedure as described above.

The results are shown in FIG. 2.

All of the human anti-human LOX-1 monoclonal antibodies produced by the hybridomas significantly bound to (had affinity towards) human LOX-1 expressed by the recombinant CHO cells. In addition, some of the human anti-human LOX-1 monoclonal antibodies were also demonstrated to have cross-reactivity to bovine LOX-1.

EXAMPLE 4

Inhibitory Activity of Human Anti-Human LOX-1 Monoclonal Antibody on the Incorporation of Oxidized LDL The oxidized LDL receptor-neutralizing activity of the human anti-oxidized LDL receptor monoclonal antibody in the culture supernatant of each hybridoma obtained by the above-mentioned screening was analyzed by determining the presence or absence of the activity to inhibit the incorporation of oxidized LDL into cells according to the procedure described below.

<4-1> Preparation of DiI-Labeled Human Oxidized LDL

After the specific gravity of a normal healthy subject's plasma was adjusted to 1.019 by adding potassium bromide (KBr), the mixture was centrifuged in a BeckmanL-80 ultracentrifuge (at 58,000 rpm for 20 hours). The bottom layer was collected into another tube. The collected liquid amount was determined, and then potassium bromide was added to the liquid to adjust its specific gravity to 1.063. Then, the mixture was centrifuged in a BeckmanL-80 ultracentrifuge (at 58,000 rpm for 20 hours). The top layer was collected into another tube. The collected fraction was dialyzed against phosphate buffer (the outer dialysate was changed more than once) to prepare purified human LDL. The concentration of protein estimated with a BCA protein assay kit (PIERCE) was 10.3 mg/ml.

To prepare oxidized LDL from the resulting purified LDL, a solution in which the concentrations of purified LDL and copper sulfate ($CuSO_4$) had been adjusted to 3 mg/ml and 75 M, respectively, was incubated in a $CO_2$ incubator for 20 hours. Then, the solution was dialyzed against a 0.15 M sodium chloride solution containing EDTA (the outer dialysate was changed more than once) to obtain human oxidized LDL. The concentration of protein estimated with a BCA protein assay kit (PIERCE) was 2.32 mg/ml.

Both purified LDL and oxidized LDL prepared as described above were subjected to agarose electrophoresis on an agarose gel (Titan Gel Lipoproteins; Helena Institute) (constant voltage: 90 V; for 25 minutes). The gel was dried in a gel drier at 55° C and fat red 7B staining solution was added to visualize lipids. Then, the gel was destained with 70% methanol, and dried again in the gel drier at 55° C. The degree of lipid oxidation estimated using a TBARS (lipid peroxide LPO) assay kit (LPO-test WAKO (Wako Pure Chemical Industries, Ltd)) was 24.74 mol/mg protein. The human oxidized LDL obtained as described above was used as the standard substance.

The obtained human oxidized LDL was labeled with a commercially available labeling substance (abbreviated as "DiI"; 1'-Dioctadecyl-3,3,3',3'-tetramethylindocarbocyanine-perclorate Funakoshi) according to the manual for the experiment procedure to prepare DiI-human oxidized LDL.

<4-2> Assay for the Inhibitory Activity on the Incorporation of Oxidized LDL into Cells The CHO cells expressing human LOX-1 ($5 \times 10^4$ cells/well) or bovine LOX-1 ($5 \times 10^4$ cells/well), prepared as described above, were plated on 24-well microtiter plates and cultured to be confluent. The culture supernatant was discarded, and the culture supernatant of hybridoma (150 µl/well) prepared as described above, 40% NBCS (new born calf serum; 40 µl/well), and DiI-human oxidized LDL (80 µg/ml×10 µl/well) prepared as described above were added to each well in this order. The plates were incubated at 37° C for 2 hours. After the plates were washed with phosphate buffer, 1% NP-40 in PBS (200 µl/well; Nonidet P-40; Nacalai Tesque) was added to each well. The plates were then incubated at room temperature for 30 minutes.

The culture supernatant (180 µl/well) was transferred from each well to another 96-well microplate and subjected to fluorescence analysis using a Fluoroscan II (Labsystems) (emission wavelength: 590 nm; excitation wavelength: 544 nm).

Control experiments were carried out by the same procedure as described above in the absence of either the hybridoma supernatant or DiI-human oxidized LDL.

In addition, a test was carried out in the same way as described above, using as a negative control antibody a human anti-KLH monoclonal antibody prepared by immunizing the above-mentioned transgenic mouse producing human antibody with KLH (keyhole limpet hemocyanin; PIERCE) by the same procedure as described above. The results are shown in FIG. 3.

All of the human anti-human LOX-1 monoclonal antibodies produced by the hybridomas were found to have the activity of significantly inhibiting LOX-1-mediated incorporation of oxidized LDL into cells.

EXAMPLE 5

Isotyping of Human Anti-Human LOX-1 Monoclonal Antibodies

Isotyping of the human anti-human oxidized LDL receptor monoclonal antibodies produced by the hybridomas, which had been obtained by the above-mentioned screening, was carried out in the same way as in ELISA (Part 1) describe above.

However, in the ELISA assay in this Example, soluble human oxidized LDL receptor coated on the plates were not hLOX-Fc chimeric protein but purified FLAG-hLOX-1 prepared as described above.

To determine whether the heavy chain (H chain) of a human monoclonal antibody is IgG or IgM, commercially available peroxidase-conjugated anti-human IgG-Fc antibody or anti-human IgM antibody was used as the secondary antibody.

To determine whether the light chain (L chain) of a human monoclonal antibody is Igκ or Igλ, commercially available peroxidase-conjugated anti-human Igκ antibody or anti-human Igλ antibody was used as the secondary antibody.

As a result, all of the human anti-human LOX-1 monoclonal antibodies produced by the hybridomas were IgG/κ.

EXAMPLE 6

Cloning of Hybridoma

The respective hybridomas producing human monoclonal antibodies neutralizing human oxidized LDL, which were identified by a multiple set of ELISA assay, test for the activity of inhibiting the oxidized LDL incorporation, and isotyping as described above, were subcloned by repeating the above-mentioned tests. Thus, various monoclonal hybridomas producing human anti-human LOX-1 monoclonal antibodies were prepared.

EXAMPLE 7

Preparation of Human Anti-Human LOX-1 Monoclonal Antibody on a Large Scale

Each of the above-mentioned hybridoma clones, (1 to $2 \times 10^6$ cell/ml each) conditioned in ASF104 medium (Ajinomoto) containing 10% Ultra Low Bovine IgG FBS (GIBCO-BRL), was plated and cultured in Integra Cell Line 1000 (INTEGRA CL1000, Integra Bioscience). After a 7 to 10-day culture, when the density of culture cells reached about $10 \times 10^8$ cells/ml, the supernatant of each hybridoma culture was recovered.

Then, hybridoma cultures were centrifuged (at 3,000 rpm for ten minutes) and each of the obtained supernatants was loaded onto a HiTrapProteinG Column (HiTrap affinity column Protein G; Amersham Pharmacia). Then, the column was washed with phosphate buffer, and a solution (pH 2.0) consisting of 100 mM citric acid and 150 mM NaCl was loaded onto the Protein G column to elute the antibody. The elution was neutralized by adding a solution (pH 9.0) containing 750 mM Tris-HCl, and then filtered with a filter (Millipore) to remove the white precipitation. The obtained filtrate was dialyzed against phosphate buffer (overnight), and filtered with a filter (Millipore). Thus, the human anti-human LOX-1 monoclonal antibodies were purified.

EXAMPLE 8

Determination of the Subclass of the Human Anti-Human LOX-1 Monoclonal Antibodies Determination of the subclass of the respective human anti-human LOX-1IgG monoclonal antibodies prepared as above was carried out with human monoclonal antibody isotyping kit (American Qualex). The experiment was carried out according to the protocol attached to the kit.

It was demonstrated that the human anti-human TβRII monoclonal antibodies are IgG2/κ or IgG4/κ (FIG. 4).

EXAMPLE 9

Test for Reactivity to Natural Human Cells Expressing Human LOX-1

The reactivity (binding activity) of each human anti-human LOX-1 monoclonal antibody, prepared as described above, to natural human cells was analyzed as follows.

<9-1> Expression of Human LOX-1 in HeLa S-3 (Part 1: Cell ELISA)

The expression of LOX-1 molecule in HeLa S-3, which is a natural human cell, was confirmed by the same procedure as the above-mentioned ELISA (Part 2; cell ELISA).

HeLa S-3 cells ($1\times10^4$ cells/well; ATCC CLL-2.2; DAINIPPON PHARMACEUTICAL) were plated on a collagen Type I-coated 96-well microtiter plate containing Ham's F12 medium with 10% FCS, and then incubated at 37° C for 2 days. The culture supernatant was discarded, and the wells were washed with Ham's F12 culture medium containing 0.1% BSA. Recombinant human TNFα (10 ng/ml×200 μl/well) was added to each well, and then the plate was incubated at 37° C for 6 hours. After the culture supernatant was discarded, various human anti-human LOX-1 monoclonal antibodies (50 μl/well) prepared as described above were added to the wells. The plate was incubated at room temperature for one hour, and then each well was washed twice with the medium.

Then, peroxidase-conjugated goat anti-human immunoglobulin (Fc) antibody (50 μl of 7,000-fold dilute; American Corex) was added to each well, and the plate was incubated at room temperature for 30 minutes. After the microtiter plate was washed twice with the medium, 100 μl of tetramethylbenzidine (3,3',5,5'-tetramethylbenzidine (TMB); BIO-RAD) was added to each well and the plate was incubated at room temperature for 30 minutes.

Then, 25 μl of 0.5 M $H_2SO_4$ was added to each well to stop the reaction. The absorbance at the wavelength of 450 nm was measured with a Model 3550 Microplate Reader (Bio-Rad).

Control experiments were carried out by the same procedure using a microtiter plate except that HeLa S-3 cells had been cultured in Ham's F12 culture medium without 10% FCS.

A negative control test was carried out in the same way, using the human anti-KLH monoclonal antibody prepared as describe above.

The results are shown in FIG. 5.

HeLa S-3 cells were confirmed to express human LOX-1 at a significantly high level.

<9-2> Expression of Human LOX-1 in HeLa S-3 (Part 1: Northern Blotting)

The expression of LOX-1 molecule in HeLa S-3, which is a was confirmed by Northern blotting according to a conventional method.

HeLa S-3 cells ($1\times10^4$ cells/well; ATCC CLL-2.2; DAINIPPON PHARMACEUTICAL) were plated on a collagen Type I-coated 96-well microtiter plate containing Ham's F12 culture medium with 10% FCS, and incubated at 37° C for 2 days. After the culture supernatant was discarded, each well was washed with Ham's F12 medium containing 0.1% BSA. Recombinant human TNFα (10 ng/ml×200 μl/well) was added to each well, and the plate was incubated at 37° C for 6 hours. Then, according to the conventional method, poly (A) RNA was prepared from the total RNA obtained from the cells. The poly(A)$^+$ RNA was subjected to agarose gel electrophoresis, and then the RNA was transferred onto a nylon membrane according to the conventional method.

The expression plasmid for recombinant human LOX-Fc chimeric protein prepared as described above was labeled with [α-$^{32}$P]dCTP (Amersham) to prepare a hybridization probe.

The [α-32 P]dCTP-labeled hLOX-1 DNA was hybridized to the prepared poly(A)$^+$ RNA blotted onto the nylon membrane. Then, the membrane was washed with 1×SSC/0.1% SDS at room temperature for 20 minutes and three times with 0.1×SCS/0.1% SDS at 65° C for 20 minutes. The membrane was then subjected to autoradiography.

According to a conventional method, hybridization was carried out using the reagents and condition described below:
(1) hybridization solution (20×SSC (45 ml; 6-fold dilute; Nacalai Tesque), 50×Denhardt's solution (15 ml; 5-fold dilute; Wako Pure Chemical Industries), 10% SDS (7.5 ml; 0.5%), and distilled water (82.5 ml); total 150 ml);
(2) salmon sperm DNA (10 mg/ml; Gibco BRL);
(3) solution of hybridization probe ([α-$^{32}$P]dCTp-labeled hLOX-1 DNA (5 μl; 5 ng/μl) and distilled water (40 μl): total 45 μl);
(4) prehybridization 1 (10 ml of hybridization solution without salmon sperm DNA for 10 minutes);
(5) prehybridization 2 (18 ml of hybridization solution containing salmon sperm DNA for 3 hours (65° C.)); and
(6) hybridization (13.6 μl of probe solution at 65° C and then on ice).

As a result, an approximately 2.5-kb band (theoretical value: approximately 2.5 kb) was detected. Thus, HeLa S-3 cells were confirmed to express LOX-1.

<9-3> Oxidized LDL-Incorporating Activity of HeLa S-3 Cells and Inhibitory Activity of Human Anti-Human LOX-1 Monoclonal Antibody on the Incorporation The activity of oxidized LDL incorporation by the natural human cell HeLa S-3, which had been confirmed to express human LOX-1 in the above-mentioned test, and inhibitory activity of human anti-human LOX-1 monoclonal antibodies on the incorporation of oxidized LDL into cells were assayed as follows.

HeLa S-3 cells ($5\times10^4$ cells/well; ATCC CLL-2.2; DAINIPPON PHARMACEUTICAL) were plated on a collagen Type I-coated 24-well microtiter plate containing Ham's F12 culture medium with 10% FCS and incubated at 37° C for 2 days. After the culture supernatant was discarded, each well was washed with Ham's F12 medium containing 0.1% BSA. Recombinant human TNFα (10 ng/ml×200 μl/well) was added to each well, and the plate was incubated at 37° C for 6 hours. Then, the culture supernatant was discarded, and various human anti-human LOX-1 monoclonal antibodies (150 µl/well) prepared as describe above, 40% NBCS (New born calf serum; 40 µl/well), and the DiI-human oxidized LDL (80 µg/ml×10 µl/well) prepared as described above were added to each well in this order. The plate was incubated at 37° C for 1 hour. After the plate was washed with phosphate buffer, 5 mM EDTA in PBS (100 µl/well) was added to each well. The plate was incubated at room temperature for 5 minutes. Then, 100 µl of PBS containing 10% FCS was added to each well to harvest the cells.

The percentage (%) of cells incorporating DiI-oxidized LDL, and the amount of DiI-oxidized LDL incorporated into the cells (fluorescence intensity) were determined using a flow cytometer (excitation wavelength: 488 nm; emission wavelength: 575 nm).

A control experiment was carried out in the absence of either the human anti-LOX-1 monoclonal antibody or DiI-human oxidized LDL by the same procedure as described above.

In addition, a test was carried out in the same way as described above, using as a negative control antibody a human anti-KLH monoclonal antibody prepared by immunizing the above-mentioned transgenic mouse producing human antibody with KLH (keyhole limpet hemocyanin; PIERCE) by the same procedure as described above.

The results are shown in FIG. 6 and FIG. 7.

The results indicated that HeLa S-3 cells incorporate oxidized LDL and all of the human anti-human LOX-1 monoclonal antibodies have the activity of significantly inhibiting LOX-1-mediated incorporation of oxidized LDL into natural cells.

EXAMPLE 10

Determination of the Affinity and Neutralizing Activity of Human Anti-Human LOX-1 Monoclonal Antibodies to the Antigen The association rate constant (ka), dissociation rate constant (kd), and dissociation constant (Kd) of the binding between the various human monoclonal antibodies against anti-human oxidized-LDL receptor (LOX-1) prepared as described above and human LOX-1 were determined using the commercially available assay kit Biacore X (Amersham-Pharmacia).

The procedures other than the immobilization of the antigen on a sensor chip described below were carried out according to the instructions and experimental protocol attached to the corresponding kit.

The human LOX-FC chimeric protein prepared as described above was used as human LOX-1 to be immobilized on a sensor chip. 0.01 M HBS buffer (containing 0.15 M NaCl, 3 mM EDTA, and 0.005% Detergent P20, pH 7.0) was injected through a flow cell-1 attached to the kit at a flow rate of 5 µl/min. Then, 100 µl of 0.005 M NHS (N-hydroxysuccinimide)/0.2 M EDC(N-ethyl-N'-(dimethylaminopropyl) carbodiimide was injected to activate the carboxyl groups of the CM coated on the sensor chip. Then, 5 µl of human LOX-Fc (10 µg/ml; dissolved in 10 mM sodium acetate buffer (pH 5.0)) was poured over the chip to immobilize it on the sensor chip. The amount of immobilized human LOX-FC was 231 RU (resonance unit). Then, non-reacted activated carboxyl groups were blocked by adding 35 µl of 1 M ethanol amine hydrochloride.

Capping of flow cell-2 (used as a reference) was carried out by the same treatment as described above in the absence of the human LOX-Fc.

Phosphate buffer was injected to the flow cell at a flow rate of 20 µl/minute, and each of the purified human anti-human LOX-1 monoclonal antibody prepared in the above Example (10 to 50 µg/ml, 60 µl) was added thereto.

The standard assay condition comprised the association phase for three minutes and dissociation phase for 10 minutes. A sensorgram was obtained by measuring the amounts of the bound antibody over time. Based on the sensorgram data so obtained, the association rate constant (ka), dissociation rate constant (kd), and dissociation constant (Kd; Kd=kd/ka) were computed using analysis software (BIAevaluation 3.0) attached to the kit. The result is shown in FIG. 4.

All of the human anti-human LOX-1 monoclonal antibodies exhibited extremely high binding affinity and neutralizing activity towards human LOX-1.

EXAMPLE 11

Cross-Reactivity to LOX-1 Derived from Various Non-Human Mammals

Whether the human anti-human LOX-1 monoclonal antibodies prepared as described above exhibit cross-reactivity to bovine, pig, and rabbit LOX-1 was tested using the recombinant CHO cells expressing the respective LOX-1 prepared in Example 1. The test was carried out by the same procedure as used in the inhibition test for of oxidized LDL incorporation in Example 4.

The results are shown in FIG. 8 (cross-reactivity to bovine LOX-1) and FIG. 4 (cross-reactivity to LOX-1 derived from various non-human mammals).

Another test was carried out to confirm whether the antibodies exhibited cross-reactivity to bovine, pig, and rabbit LOX-1 using the recombinant CHO cells expressing the respective LOX-1 prepared in Example 1. The test was carried out by the same procedure as used in cell ELISA (Part 2) in Example 3.

The results are shown in FIG. 4.

The human anti-human LOX-1 monoclonal antibodies of the present invention exhibited various types of cross-reactivity profiles.

EXAMPLE 12

Therapeutic Effect of Anti-LOX-1 Antibody on LPS-Induced Thrombocytopenia

LPS (lipopolysaccharide; Sigma), which had been dissolved in physiological saline to 1 mg/ml, was given to Sprague-Dawley rats (5-7 week-old male; JCL) by intraperitoneal injection at a dose of 3 mg/kg to prepare thrombocytopenia model rats.

Anti-bovine LOX-1 monoclonal antibodies having cross-reactivity to rat LOX-1 were prepared by the same methods as described above (Biochem. J., Vol. 330, Pt. 3, p. 1417-1422, 1998; GenBank Accession Nos. BAA25785 and AB005900 (SEQ ID NOs: 14 and 15)). The cross-reactivity to rat LOX-1 was tested using the rat LOX-1-expressing recombinant CHO cells prepared in Example 1 by the same procedure as used in cell ELISA (Part 2) of Example 3.

Immediately after LPS administration, anti-LOX-1 antibody or control antibody with no reactivity to LOX-1, which had been dissolved in physiological saline to 1 mg/ml, was given by intravenous injection to the rats at a dose of 5 mg/kg. Rats to which neither LPS nor antibody had been given, were used as normal controls. Before and 2 hours after LPS administration, blood was collected from the rats. The number of blood platelets were counted with an automatic hemocyte counter Sysmex F800 (Nihon Kohden Co.).

The results are shown in FIG. 9. In the group subjected to control antibody administration, the number of blood platelets decreased 2 hours after LPS administration. On the other hand, the reduction in the blood platelet count was suppressed significantly in the group subjected to administration of anti-LOX-1 antibody.

EXAMPLE 13

Therapeutic Effect of Anti-LOX-1 Antibody on LPS-Induced Lung Disorders

The anti-LOX-1 antibodies (2, 5, and 10 mg/kg) or physiological saline (5 mg/kg) were given by intravenous injection to Sprague-Dawley rats (6-7 week-old male; each group contained 6 individuals; SLC), and then the rats were anesthetized with pentobarbital (30 to 50 mg/kg, i.p.). One hour after intravenous injection of antibody (or physiological saline), LPS (lipopolysaccharide; Sigma) dissolved in physiological saline was given through the airway at a dose of 1 mg/kg. Physiological saline was given to the control group of normal rats through the airway.

24 hours after LPS administration, the rats were anesthetized with ether and underwent laparotomy. The rats were sacrificed by bloodletting from the abdominal aorta. Then, the rats were opened at the pharyngeal section. A cut down tube (JMS) was inserted into the airway. 5 ml of physiological saline containing 0.05 mM EDTA, namely bronchioalveolar lavage fluid (BALF recovering solution)), was injected into the rats through the tube using a 5-ml syringe. Moving the piston of the syringe back and forth 15 times, the BALF was recovered from the rats. The BALF was allowed to stand on ice, and then centrifuged at 1000 rpm for 10 minutes at 4° C. After centrifugation, the resulting supernatant was discarded by decantation, and 0.5 ml of the BALF recovering solution was added to the precipitate and gently suspended. The number of leukocytes in the suspension was counted with an automatic hemocyte counter Sysmex F800 (Nihon Kohden).

The results are shown in FIG. 10. In the group treated with anti-LOX-1 antibody, the number of leukocytes infiltrating into tissues was significantly reduced in an antibody-concentration dependent fashion. Surprisingly, the antibody inhibited the leukocyte infiltration into tissues by about 50% when the antibody dose was 10 mg/kg.

EXAMPLE 14

Therapeutic Effect of Anti-LOX-1 Antibody on LPS-Induced Inflammation

Either an anti-LOX-1 antibody (10 mg/kg) or physiological saline (10 mg/kg) was given by intravenous injection to Sprague-Dawley rats (200 g; SLC). One hour after intravenous injection of the antibody (or physiological saline), LPS (lipopolysaccharide; Sigma) dissolved in physiological saline was given to the footpad of the rats at a dose of 1 mg/kg. Physiological saline was given to the control group of normal rats to the footpad.

Twelve hours after LPS administration, blood was collected from the rats according to the conventional method. The number of leukocytes infiltrating into the anterior chamber of the eyes was counted with an automatic hemocyte counter Sysmex F800 (Nihon Kohden Co.). Further, the total amount of protein leakage into the anterior chamber of eyes was determined.

The results are shown in FIG. 11 and FIG. 12. In the group subjected to the administration of anti-LOX-1 antibody, the number of leukocytes infiltrating into tissue of anterior chamber of eyes and the amount of protein leakage were both significantly reduced.

EXAMPLE 15

Therapeutic Effect of Anti-Lox-1 Antibody on Restenosis after PTCA

Sprague-Dawley rats (male, approximately 300 g; SLC) were anesthetized with pentobarbital (30 to 50 mg/kg, i.p.). The carotid artery and external carotid artery were exposed by surgery, and then both arteries were ligated temporarily to stop the blood flow. Then, the external artery was punctured, and a 2F balloon catheter (Baxter) was inserted into the artery. Shear stress was given to the vascular endothelium of the artery by using the pressure of 0.4-ml air sent into the artery; the air bubble was allowed to move three times back and forth. Then, the external carotid artery was ligated, and the temporal ligation of carotid artery and internal carotid artery was released to resume the blood flow. The site opened by surgery was closed by stitching, and immediately anti-LOX-1 antibody (10 mg/kg) was given by intravenous injection to the rats.

Then, the antibody (10 mg/kg) was given by intravenous injection 4 times every 3 days. After 2 weeks, the rats were again anesthetized with pentobarbital (30 to 50 mg/kg, i.p.), and then rat tissues were fixed by refusing 4% formaldehyde/phosphate buffer. The carotid artery was excised from the rats. The carotid artery was embedded in paraffin, and 6 sections were prepared from a single sample. The sections were stained by Elastica-van Gieson staining. The thickening of vascular endothelium in each section was evaluated using the NIH analyzing system to estimate the real ratio between the endothelium and media. Two sections showing significant thickening were selected and the averaged value of the two was defined as the thickening level of the sample.

The results are shown in FIG. 13. Restenosis after PTCA was significantly suppressed by anti-LOX-1 antibody.

EXAMPLE 16

Suppressive and Preventive Effects of Anti-LOX-1 Antibody on Thrombus Formation in Arteria In this Example, a rat model where thrombus formation is artificially induced by a photochemical method (PIT model; photochemically-induced thrombosis model) (J. Pharmacol. Method., Vol. 25, p. 303, 1991; Thrombo. Res., Vol. 63, p. 405, 1991, and such) was used.

Normal rats were anesthetized with thiobutabarbital (100 mg/kg, i.p.). Each rat was fixed dorsally, and a blood-pressure measuring cannula was inserted into the left femoral artery to measure the blood pressure continuously. In the left femoral vein, a cannula was also inserted to give rose bengal (20 mg/kg), which is a radical inducer. Further, right peripheral femoral artery was dissected and exposed to arrange a pulse Doppler blood stream probe.

Using a xenon lamp, green light at the wavelength of 540 nm was irradiated to a more medial site approximately 2 mm apart from the site where the pulse Doppler blood stream probe had been placed. After 5 minutes, rose bengal (20 mg/kg) was given by intravenous injection to induce thrombus formation. The light irradiation was continued for 10 minutes and then stopped. The progress of thrombus formation was monitored based on detectable sound of blood stream as an index for 90 minutes.

To test the suppressive effect of anti-LOX-1 antibody on thrombus formation, the anti-LOX-1 monoclonal antibody (10 mg/kg) prepared in the Example described above was given by intravenous injection, one hour before the irradiation with the xenon lamp.

The results are shown in FIG. 14 and FIG. 15.

The anti-LOX-1 antibody significantly suppressed the thrombus formation.

INDUSTRIAL APPLICABILITY

As the human monoclonal antibodies of the present invention binding to human oxidized LDL receptor (hLOX-1) are derived from humans, they have no antigenicity towards humans, which is a major therapeutic problem (side effect) in medical treatment using antibody pharmaceuticals comprised of antibodies derived from non-human mammals, such as mice. This means that the antibodies of the present invention do not induce severe host immunorejections caused by HAMA (human anti-mouse antigenicity) (i.e., do not induce any host immunorejection caused by HAMA), and therefore, the present invention dramatically elevates the value of antibodies as pharmaceuticals.

Thus, human anti-human oxidized LDL receptor monoclonal antibodies of the present invention and pharmaceutical compositions comprising the human monoclonal antibodies, and substances (for example, various monoclonal antibodies including the human monoclonal antibodies, chemically synthesized low-molecular-weight compounds, and such) having the activity of inhibiting the binding of in-vivo ligands of the oxidized LDL receptor to the oxidized LDL receptor, or the incorporation of the ligands into cells expressing the oxidized LDL receptor, can inhibit the binding of in-vivo ligands of human LOX-1 (for example, modified LDLs such as oxidized LDLs, senescent erythrocytes, apoptotic cells, activated blood platelets, and such) to LOX-1 and/or the LOX-1-mediated incorporation of the ligands into cells. Therefore, they are useful as pharmaceuticals for the treatment and prevention of various diseases caused by interaction (binding and incorporation) between LOX-1 ligands and LOX-1 (for example, arteriosclerosis, thrombocytopenia, kidney disease, various types of inflammation (for example, myocardial ischemic reperfusion injury, inflammatory reactions after percutaneous transluminal coronary recanalization (PTCR) or percutaneous transluminal coronary angioplasty (PTCA)), vessel restenosis after PTCA and PTCR, and thrombus formation in the blood vessels (e.g., artery) by suppressing and inhibiting the onset and/or progress of the diseases.

We claim:

1. A method of inhibiting binding between an in-vivo ligand of human oxidized low density lipoprotein receptor (LOX-1) and human LOX-1 or the incorporation of the ligand into cells expressing LOX-1, wherein the LOX-1 comprises amino acids 65-273 as set forth in SEQ ID NO:2, the method comprising administering to an individual suffering from a disease or condition associated with human LOX-1 an effective amount of an isolated neutralizing monoclonal antibody, or a binding portion thereof, specific for LOX-1.

2. The method according to claim 1, wherein the disease or condition is arteriosclerosis.

3. The method according to claim 1, wherein the disease or condition is caused by the binding of blood platelets or activated blood platelets to the oxidized LDL receptor, or the incorporation of blood platelets or activated blood platelets into cells expressing the oxidized LDL receptor.

4. The method according to claim 3, wherein the disease or condition involves the symptoms of thrombocytopenia.

5. The method according to claim 3, wherein the disease or condition is a kidney disease.

6. The method according to claim 1, wherein the disease or condition is treated by inhibiting leukocyte infiltration into tissues.

7. The method according to claim 6, wherein the disease or condition is treated by reducing inflammatory reactions during arteriosclerosis, during myocardial ischemic reperfusion injury, after percutaneous transluminal coronary recanalization (PTCR), or after percutaneous transluminal coronary angioplasty (PTCA).

8. The method according to claim 1, wherein the disease or condition is inflammation.

9. The method according to claim 8, wherein the inflammation is due to arteriosclerosis, myocardial ischemic reperfusion injury, after percutaneous transluminal coronary recanalization (PTCR), or after percutaneous transluminal coronary angioplasty (PTCA).

10. The method according to claim 1, wherein the disease or condition is vascular restenosis after percutaneous trans luminal coronary recanalization (PTCR) or percutaneous transluminal coronary recanalization (PTCR).

11. The method according to claim 1, wherein the disease or condition is treated by reducing thrombus formation.

12. The method according to claim 1 wherein the isolated neutralizing monoclonal antibody, or a binding portion thereof, is human.

13. The method according to claim 1 wherein the isolated neutralizing monoclonal antibody, or a binding portion thereof, belongs to the immunoglobulin class of IgG1 or IgG4.

14. The method according to claim 1 wherein the isolated neutralizing monoclonal antibody, or a binding portion thereof, has an association rate constant (ka) of $1.0 \times 10^4$ (1/M.Sec) or higher in its binding to the LOX-1.

15. The method according to claim 1 wherein the isolated neutralizing monoclonal antibody, or a binding portion thereof, has a dissociation rate constant (kd) of $1.0 \times 10^{-2}$ (1/Sec) or lower in its binding to the LOX-1.

16. The method in claim 1 wherein the isolated neutralizing monoclonal antibody, or a binding portion thereof, has a dissociation constant (Kd) of $1.0 \times 10^{-6}$ (M) or lower in its binding to the LOX-1.

17. The method in claim 1 wherein the isolated neutralizing monoclonal antibody, or a binding portion thereof, has an association rate constant (ka) of $1.0 \times 10^5$ (1/M.Sec) or higher in its binding to the LOX-1.

18. The method in claim 1 wherein the isolated neutralizing monoclonal antibody, or a binding portion thereof, has a dissociation rate constant (kd) of $1.0 \times 10^{-4}$ (1/Sec) or lower in its binding to the LOX-1.

19. The method in claim 1 wherein the isolated neutralizing monoclonal antibody, or a binding portion thereof, has a dissociation constant (Kd) of $1.0 \times 10^{-7}$ (M) or lower in its binding to the LOX-1.

20. The method in claim 1 wherein the isolated neutralizing monoclonal antibody, or a binding portion thereof, is a human antibody derived from a transgenic non-human mammal having the ability to produce human antibodies.

21. The method in claim 1 wherein the neutralizing monoclonal antibody, or a binding portion thereof, is a human antibody obtained by immunizing a transgenic non-human mammal having the ability to produce human antibodies with cells expressing human LOX-1, a soluble membrane fraction from the cells, the entire human LOX-1 protein or an antigenic portion thereof.

22. The method according to claim 20 or 21 wherein the transgenic non-human mammal is a transgenic mouse.

23. The method according to claim 1, wherein the isolated neutralizing monoclonal antibody, or a binding portion thereof, is administered in a dose of 0.1 mg to 100 mg/kg body weight.

24. The method according to claim 23, wherein the isolated neutralizing monoclonal antibody, or a binding portion thereof, is administered in a dose of 2 mg to 50 mg/kg body weight.

25. The methods according to claim 23, wherein the isolated neutralizing monoclonal antibody, or a binding portion thereof, is administered in a dose of 2 mg to 20 mg/kg body weight.

26. A method of treating a patient suffering from arteriosclerosis, comprising administering to the patient an effective amount of an isolated neutralizing monoclonal antibody, or binding fragment thereof, specific for human oxidized low density lipoprotein receptor (LOX-1).

27. The method according to claim 26, wherein the antibody is a fully human monoclonal antibody.

28. The method according to claim 26, wherein the (LOX-1) comprises amino acids 65-273 as set forth in SEQ ID NO:2.

* * * * *

SEQUENCE LISTING

```
<160> NUMBER OF SEQ ID NOS: 15

<210> SEQ ID NO 1
<211> LENGTH: 2468
<212> TYPE: DNA
<213> ORGANISM: Homo sapiens
<220> FEATURE:
<221> NAME/KEY: 5'UTR
<222> LOCATION: (1)..(61)
<220> FEATURE:
<221> NAME/KEY: CDS
<222> LOCATION: (62)..(883)
<220> FEATURE:
<221> NAME/KEY: 3'UTR
<222> LOCATION: (884)..(2468)

<400> SEQUENCE: 1 attttagtt tgttgaagtt cgtgactgct tcactctctc attcttagct tgaatttgga      60 a atg act ttt gat gac cta aag atc cag act gtg aag gac cag cct gat     109
  Met Thr Phe Asp Asp Leu Lys Ile Gln Thr Val Lys Asp Gln Pro Asp
  1               5                   10                  15 gag aag tca aat gga aaa aaa gct aaa ggt ctt cag ttt ctt tac tct       157
Glu Lys Ser Asn Gly Lys Lys Ala Lys Gly Leu Gln Phe Leu Tyr Ser
                20                  25                  30 cca tgg tgg tgc ctg gct gct gcg act cta ggg gtc ctt tgc ctg gga       205
Pro Trp Trp Cys Leu Ala Ala Ala Thr Leu Gly Val Leu Cys Leu Gly
            35                  40                  45 tta gta gtg acc att atg gtg ctg ggc atg caa tta tcc cag gtg tct       253
Leu Val Val Thr Ile Met Val Leu Gly Met Gln Leu Ser Gln Val Ser
        50                  55                  60 gac ctc cta aca caa gag caa gca aac cta act cac cag aaa aag aaa       301
Asp Leu Leu Thr Gln Glu Gln Ala Asn Leu Thr His Gln Lys Lys Lys
    65                  70                  75                  80 ctg gag gga cag atc tca gcc cgg caa caa gca gaa gaa gct tca cag       349
Leu Glu Gly Gln Ile Ser Ala Arg Gln Gln Ala Glu Glu Ala Ser Gln
                85                  90                  95
```

| | |
|---|---|
| gag tca gaa aac gaa ctc aag gaa atg ata gaa acc ctt gct cgg aag<br>Glu Ser Glu Asn Glu Leu Lys Glu Met Ile Glu Thr Leu Ala Arg Lys<br>     100                   105                 110 | 397 |
| ctg aat gag aaa tcc aaa gag caa atg gaa ctt cac cac cag aat ctg<br>Leu Asn Glu Lys Ser Lys Glu Gln Met Glu Leu His His Gln Asn Leu<br>    115                  120               125 | 445 |
| aat ctc caa gaa aca ctg aag aga gta gca aat tgt tca gct cct tgt<br>Asn Leu Gln Glu Thr Leu Lys Arg Val Ala Asn Cys Ser Ala Pro Cys<br> 130                 135              140 | 493 |
| ccg caa gac tgg atc tgg cat gga gaa aac tgt tac cta ttt tcc tcg<br>Pro Gln Asp Trp Ile Trp His Gly Glu Asn Cys Tyr Leu Phe Ser Ser<br>145               150              155            160 | 541 |
| ggc tca ttt aac tgg gaa aag agc caa gag aag tgc ttg tct ttg gat<br>Gly Ser Phe Asn Trp Glu Lys Ser Gln Glu Lys Cys Leu Ser Leu Asp<br>         165                 170             175 | 589 |
| gcc aag ttg ctg aaa att aat agc aca gct gat ctg gac ttc atc cag<br>Ala Lys Leu Leu Lys Ile Asn Ser Thr Ala Asp Leu Asp Phe Ile Gln<br>    180                  185               190 | 637 |
| caa gca att tcc tat tcc agt ttt cca ttc tgg atg ggg ctg tct cgg<br>Gln Ala Ile Ser Tyr Ser Ser Phe Pro Phe Trp Met Gly Leu Ser Arg<br> 195                 200              205 | 685 |
| agg aac ccc agc tac cca tgg ctc tgg gag gac ggt tct cct ttg atg<br>Arg Asn Pro Ser Tyr Pro Trp Leu Trp Glu Asp Gly Ser Pro Leu Met<br>210               215              220 | 733 |
| ccc cac tta ttt aga gtc cga ggc gct gtc tcc cag aca tac cct tca<br>Pro His Leu Phe Arg Val Arg Gly Ala Val Ser Gln Thr Tyr Pro Ser<br>225               230              235            240 | 781 |
| ggt acc tgt gca tat ata caa cga gga gct gtt tat gcg gaa aac tgc<br>Gly Thr Cys Ala Tyr Ile Gln Arg Gly Ala Val Tyr Ala Glu Asn Cys<br>         245                 250             255 | 829 |
| att tta gct gcc ttc agt ata tgt cag aag aag gca aac cta aga gca<br>Ile Leu Ala Ala Phe Ser Ile Cys Gln Lys Lys Ala Asn Leu Arg Ala<br>    260                  265               270 | 877 |
| cag tga atttgaaggc tctggaagaa aaggaaaaag tctttgagtt ttattctgga<br>Gln | 933 |
| atttaagcta ttctttgtca cttgggtgcc aaacatgaga gcccagaaaa ctgtcattta | 993 |
| gctggctgca gaactccttt gcagaaactg gggttccagg tgcctggcac ctttatgtca | 1053 |
| acatttttga ttctagctat ctgtattatt tcacctagct tgtcccaagc ttccctgcca | 1113 |
| gcctgaagtc cattttcccc ttttattttt aaaatttgac tcctcttcaa gcttgaaaac | 1173 |
| cctctgaact cagtcttctt tacctcatta tcacctt ccc ctcacactcc taaaattgca | 1233 |
| tgaaagacag aacatggaga acttgctcaa gtgcaggcag agagcaaaaa ggggaaatat | 1293 |
| gtctgggaaa aagtgcacgt gaagaaacaa agaaggacag aggccattcc gaaatcaaga | 1353 |
| aactcatgtt cttaacttta aaaaggtat caatccttgg tttttaaact gtggtccatc | 1413 |
| tccagactct accacttacg gacagacaga cagacagaca cacacacaca cacacacaca | 1473 |
| cacacacaca ttttgggaca agtggggagc ccaagaaagt aattagtaag tgagtggtct | 1533 |
| tttctgtaag ctaatccaca acctgttacc acttcctgaa tcagttatta tttcttcatt | 1593 |
| ttttttttcta ccagaggaca gattaataga tttaacccctt cacaacagtt cttgttagaa | 1653 |
| tcatgggatg tgtggcccag aggtaagaat agaatttctt tccctaaaga acataccttt | 1713 |
| tgtagatgaa ctcttctcaa ctctgttttg ctatgctata attccgaaac atacaagaca | 1773 |
| aaaaaaatga agacactcaa tctagaacaa actaagccag gtatgcaaat atcgctgaat | 1833 |
| agaaacagat ggaattagaa atatatcttc tattttaggg cttctatttc ctttccaccc | 1893 |
| actcttcaca ggctattcta ctttaaagga agccttttta ttttgctgca cacaatctag | 1953 |

```
caggaatctt tttttttttt taagagctgt gtcatcctta tgtaggcaag agatgtttgc    2013
ttttgttaaa agctttattg agatataatt aacataaaat aaactgaaca tatttaaagt    2073
gtactatttg ataagttttc acaccttgtg gagaacatgc atactacaat taagagagtg    2133
aacatatcca tcatccctca aagtgtcaca atgctcctcc tgatgactcc tccccagaaa    2193
accaccaatc ggcttccatt ttgcatttt tagttttatg tgaatggaat catatagtat    2253 gtctttttt tttgtctggc ttctttcact ttgcataatt attttgagat tcatatgtct    2313
ccatcttgat gctcgtatga attcattctt ttaaatgttg aatattccct tgtatggata    2373
taccacaatt catttaccca tttacttgtt gatgacattt gggttgtttt agttttggga    2433
tattacaaat aaagctgctg tgaacatttg tgtac                              2468
```

<210> SEQ ID NO 2
<211> LENGTH: 273
<212> TYPE: PRT
<213> ORGANISM: Homo sapiens

<400> SEQUENCE: 2

```
Met Thr Phe Asp Asp Leu Lys Ile Gln Thr Val Lys Asp Gln Pro Asp
  1               5                  10                  15

Glu Lys Ser Asn Gly Lys Lys Ala Lys Gly Leu Gln Phe Leu Tyr Ser
             20                  25                  30

Pro Trp Trp Cys Leu Ala Ala Thr Leu Gly Val Leu Cys Leu Gly
         35                  40                  45

Leu Val Val Thr Ile Met Val Leu Gly Met Gln Leu Ser Gln Val Ser
     50                  55                  60

Asp Leu Leu Thr Gln Glu Gln Ala Asn Leu Thr His Gln Lys Lys Lys
 65                  70                  75                  80

Leu Glu Gly Gln Ile Ser Ala Arg Gln Gln Ala Glu Glu Ala Ser Gln
                 85                  90                  95

Glu Ser Glu Asn Glu Leu Lys Glu Met Ile Glu Thr Leu Ala Arg Lys
            100                 105                 110

Leu Asn Glu Lys Ser Lys Glu Gln Met Glu Leu His His Gln Asn Leu
        115                 120                 125

Asn Leu Gln Glu Thr Leu Lys Arg Val Ala Asn Cys Ser Ala Pro Cys
    130                 135                 140

Pro Gln Asp Trp Ile Trp His Gly Glu Asn Cys Tyr Leu Phe Ser Ser
145                 150                 155                 160

Gly Ser Phe Asn Trp Glu Lys Ser Gln Glu Lys Cys Leu Ser Leu Asp
                165                 170                 175

Ala Lys Leu Leu Lys Ile Asn Ser Thr Ala Asp Leu Asp Phe Ile Gln
            180                 185                 190

Gln Ala Ile Ser Tyr Ser Ser Phe Pro Phe Trp Met Gly Leu Ser Arg
        195                 200                 205

Arg Asn Pro Ser Tyr Pro Trp Leu Trp Glu Asp Gly Ser Pro Leu Met
    210                 215                 220

Pro His Leu Phe Arg Val Arg Gly Ala Val Ser Gln Thr Tyr Pro Ser
225                 230                 235                 240

Gly Thr Cys Ala Tyr Ile Gln Arg Gly Ala Val Tyr Ala Glu Asn Cys
                245                 250                 255

Ile Leu Ala Ala Phe Ser Ile Cys Gln Lys Lys Ala Asn Leu Arg Ala
            260                 265                 270

Gln
```

<210> SEQ ID NO 3
<211> LENGTH: 1879
<212> TYPE: DNA
<213> ORGANISM: Bos taurus
<220> FEATURE:
<221> NAME/KEY: 5'UTR
<222> LOCATION: (1)..(34)
<220> FEATURE:
<221> NAME/KEY: CDS
<222> LOCATION: (35)..(847)
<220> FEATURE:
<221> NAME/KEY: 3'UTR
<222> LOCATION: (848)..(1879)

<400> SEQUENCE: 3

| | | | | | | | | | | | | | | | | |
|---|---|---|---|---|---|---|---|---|---|---|---|---|---|---|---|---|
| gcttcactct | ctcattcttg | gaatacattt | gaaa | atg<br>Met<br>1 | act<br>Thr | gtt<br>Val | gat<br>Asp | gac<br>Asp | ccc<br>Pro | aag<br>Lys<br>5 | | | | | | 55 |

```
ggt atg aaa gat caa ctt gat cag aag cca aat ggc aag aca gca aaa       103
Gly Met Lys Asp Gln Leu Asp Gln Lys Pro Asn Gly Lys Thr Ala Lys
     10                  15                  20 ggt ttt gtt tcc tct tgg agg tgg tac cct gct gct gtg act cta ggg       151
Gly Phe Val Ser Ser Trp Arg Trp Tyr Pro Ala Ala Val Thr Leu Gly
 25                  30                  35 gtc ctt tgt ctg gga tta ctg gtg act gtt ata ttg ttg ata ctg caa       199
Val Leu Cys Leu Gly Leu Leu Val Thr Val Ile Leu Leu Ile Leu Gln
 40                  45                  50                  55 tta tcc cag gtc tct gat ctc ata aag aaa cag caa gca aat att act       247
Leu Ser Gln Val Ser Asp Leu Ile Lys Lys Gln Gln Ala Asn Ile Thr
         60                  65                  70 cac cag gaa gat atc ctg gag gga cag att tta gcc cag cgc cga tca       295
His Gln Glu Asp Ile Leu Glu Gly Gln Ile Leu Ala Gln Arg Arg Ser
     75                  80                  85 gaa aaa tct gcc cag gag tca cag aag gaa ctc aaa gaa atg ata gaa       343
Glu Lys Ser Ala Gln Glu Ser Gln Lys Glu Leu Lys Glu Met Ile Glu
 90                  95                  100 acc ctt gcc cac aag ctg gat gag aaa tcc aag aaa cta atg gaa ctt       391
Thr Leu Ala His Lys Leu Asp Glu Lys Ser Lys Lys Leu Met Glu Leu
 105                 110                 115 cac cgc cag aac ctg aat ctc caa gaa gtt ctg aaa gag gca gca aac       439
His Arg Gln Asn Leu Asn Leu Gln Glu Val Leu Lys Glu Ala Ala Asn
120                 125                 130                 135 tat tca ggt cct tgt ccc caa gac tgg ctc tgg cat gaa gaa aac tgt       487
Tyr Ser Gly Pro Cys Pro Gln Asp Trp Leu Trp His Glu Glu Asn Cys
         140                 145                 150 tac caa ttt tcc tct ggc tct ttt aat tgg gaa aaa agc cag gag aac       535
Tyr Gln Phe Ser Ser Gly Ser Phe Asn Trp Glu Lys Ser Gln Glu Asn
     155                 160                 165 tgc ttg tct ttg gat gcc cac ttg ctg aag att aat agc aca gat gaa       583
Cys Leu Ser Leu Asp Ala His Leu Leu Lys Ile Asn Ser Thr Asp Glu
 170                 175                 180 ctg gaa ttc atc cag caa atg att gcc cat tcc agt ttc ccc ttc tgg       631
Leu Glu Phe Ile Gln Gln Met Ile Ala His Ser Ser Phe Pro Phe Trp
185                 190                 195 atg ggg ttg tca atg agg aaa ccc aat tac tcg tgg ctt tgg gaa gat       679
Met Gly Leu Ser Met Arg Lys Pro Asn Tyr Ser Trp Leu Trp Glu Asp
200                 205                 210                 215 ggt act cct ttg acg ccc cac ttg ttt aga att cag gga gct gtt tcc       727
Gly Thr Pro Leu Thr Pro His Leu Phe Arg Ile Gln Gly Ala Val Ser
         220                 225                 230 cgt atg tat cct tca ggg acc tgt gca tat att caa agg gga act gtt       775
Arg Met Tyr Pro Ser Gly Thr Cys Ala Tyr Ile Gln Arg Gly Thr Val
     235                 240                 245
```

```
ttt gct gaa aac tgc att tta act gca ttc agt ata tgt caa aag aag      823
Phe Ala Glu Asn Cys Ile Leu Thr Ala Phe Ser Ile Cys Gln Lys Lys
        250                 255                 260 gcg aat cta ttg aga gca cag tga atttgaagga tctggaggaa agaaggaaa      877
Ala Asn Leu Leu Arg Ala Gln
        265                 270 cctttgaatt ctcttctgga atttaagcta tacttcatca cttagatgta aaccattaga    937
gcccagggaa atgcctgcta ctggttgagt gcagaactcc ttagcagaga ctggcccagc    997
tgcctggcac cttgatagca aaagttgcaa ttccctctgt atattttcc ctaacttgtt    1057
ccaagtcctc ccctgcagga cttcagagaa gtcaatttttt ctgtttccat tgtttctaag  1117
aacttgttgc ctaactcaag gtcacagcat ttttctcact tttgtcctat gctttcttct   1177
aggcattgta gagttttaga ttttacatgg aaatctagaa cttattttag attaatttct   1237
aagtgatata tggatgtatg gaagttttct gtttgttttt tgcttgtgag tattcaattg   1297
ttttttgcaac atttgctgaa aagactattc ttccttcact acattgcctt tgcactgttg  1357
tcaacaatta ccatacatg cctggctcta tttctggatt ttctattcct ttccatttat    1417
ttatttatta ttccttggctt acaacatcac catgatattt tgaattctat ggttctttaa  1477
tatatcttgg aatcacatgg tagtagttat tcattgttgt tctttttttag agttgtttgg  1537
ttaatctatg cttttgtatt tctgtcttaa attggcttgt ccattctaa aaaaacttga    1597
aattttgaat tgcactgaat ccatacataa atttagggaa aattgaattc ttaaaaatac   1657
tgatttgttc aactcatgaa aaaggtgtat tgctctattt aggtattcct tattttctttt 1717
aagcaatgct ttttaatgtt ctttgtgtag atattgttag attatcatca tgtatttcac   1777
attatttatg ctactgtaga tagtattgtt atcatttgtt gttcttattt tcaaagtctt   1837
ctgctagtat gtagaattat aataaagttt gatattaata tt                      1879

<210> SEQ ID NO 4
<211> LENGTH: 270
<212> TYPE: PRT
<213> ORGANISM: Bos taurus

<400> SEQUENCE: 4

Met Thr Val Asp Asp Pro Lys Gly Met Lys Asp Gln Leu Asp Gln Lys
1               5                   10                  15

Pro Asn Gly Lys Thr Ala Lys Gly Phe Val Ser Ser Trp Arg Trp Tyr
                20                  25                  30

Pro Ala Ala Val Thr Leu Gly Val Leu Cys Leu Gly Leu Leu Val Thr
            35                  40                  45

Val Ile Leu Leu Ile Leu Gln Leu Ser Gln Val Ser Asp Leu Ile Lys
        50                  55                  60

Lys Gln Gln Ala Asn Ile Thr His Gln Glu Asp Ile Leu Glu Gly Gln
65                  70                  75                  80

Ile Leu Ala Gln Arg Arg Ser Glu Lys Ser Ala Gln Glu Ser Gln Lys
                85                  90                  95

Glu Leu Lys Glu Met Ile Glu Thr Leu Ala His Lys Leu Asp Glu Lys
            100                 105                 110

Ser Lys Lys Leu Met Glu Leu His Arg Gln Asn Leu Asn Leu Gln Glu
        115                 120                 125

Val Leu Lys Glu Ala Ala Asn Tyr Ser Gly Pro Cys Pro Gln Asp Trp
    130                 135                 140

Leu Trp His Glu Glu Asn Cys Tyr Gln Phe Ser Ser Gly Ser Phe Asn
145                 150                 155                 160
```

```
Trp Glu Lys Ser Gln Glu Asn Cys Leu Ser Leu Asp Ala His Leu Leu
                165                 170                 175
Lys Ile Asn Ser Thr Asp Glu Leu Glu Phe Ile Gln Gln Met Ile Ala
            180                 185                 190
His Ser Ser Phe Pro Phe Trp Met Gly Leu Ser Met Arg Lys Pro Asn
        195                 200                 205
Tyr Ser Trp Leu Trp Glu Asp Gly Thr Pro Leu Thr Pro His Leu Phe
    210                 215                 220
Arg Ile Gln Gly Ala Val Ser Arg Met Tyr Pro Ser Gly Thr Cys Ala
225                 230                 235                 240
Tyr Ile Gln Arg Gly Thr Val Phe Ala Glu Asn Cys Ile Leu Thr Ala
                245                 250                 255
Phe Ser Ile Cys Gln Lys Lys Ala Asn Leu Leu Arg Ala Gln
            260                 265                 270

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      Artificially synthesized primer sequence
<220> FEATURE:
<221> NAME/KEY: primer_bind
<222> LOCATION: (1)..(27)

<400> SEQUENCE: 5
ggggatcctg atctcataaa gaaacag                                         27

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence:
      Artificially synthesized primer sequence
<220> FEATURE:
<221> NAME/KEY: primer_bind
<222> LOCATION: (1)..(28)

<400> SEQUENCE: 6
gcggatcctg tgctctcaat agattcgc                                        28

<210> SEQ ID NO 7
<211> LENGTH: 1459
<212> TYPE: DNA
<213> ORGANISM: Artificial Sequence
<220> FEATURE:
<223> OTHER INFORMATION: Description of Artificial Sequence:Vector DNA
      of pCd51neg1 containing genomic DNA comprising exons
      encoding a Fc region of human immunoglobulin IgG1

<400> SEQUENCE: 7
ctcgagatcc attgtgctct aaaggagata cccggccaga caccctcacc tgcggtgccc      60
agctgcccag gctgaggcaa gagaaggcca gaaaccatgc ccatgggtc tctgcaaccg      120 ctggccacct tgtacctgct ggggatgctg gtcgcttccg tgctagcgga tcccgagggt      180
gagtactaag cttcagcgct cctgcctgga cgcatcccgg ctatgcagcc ccagtccagg      240
gcagcaaggc aggccccgtc tgcctcttca cccggagcct ctgcccgccc cactcatgct      300
cagggagagg gtcttctggc ttttccccag gctctgggca ggcacaggct aggtgcccct      360
aacccaggcc ctgcacacaa aggggcaggt gctgggctca gacctgccaa gagccatatc      420
```

```
cgggaggacc ctgcccctga cctaagccca ccccaaaggc caaactctcc actccctcag      480
ctcggacacc ttctctcctc ccagattcca gtaactccca atcttctctc tgcagagccc      540
aaatcttgtg acaaaactca cacatgccca ccgtgcccag gtaagccagc ccaggcctcg      600
ccctccagct caaggcggga caggtgccct agagtagcct gcatccaggg acaggcccca      660
gccgggtgct gacacgtcca cctccatctc ttcctcagca cctgaactcc tgggggacc       720 gtcagtcttc ctcttccccc caaaacccaa ggacaccctc atgatctccc ggaccccga       780 ggtcacatgc gtggtggtgg acgtgagcca cgaagaccct gaggtcaagt tcaactggta      840
cgtggacggc gtggaggtgc ataatgccaa gacaaagccg cgggaggagc agtacaacag      900
cacgtaccgg gtggtcagcg tcctcaccgt cctgcaccag gactggctga atggcaagga      960
gtacaagtgc aaggtctcca acaaagccct cccagccccc atcgagaaaa ccatctccaa     1020
agccaaaggt gggacccgtg gggtgcgagg gccacatgga cagaggccgg ctcggcccac     1080
cctctgccct gagagtgacc gctgtaccaa cctctgtcct acagggcagc ccgagaacc      1140 acaggtgtac accctgcccc catcccggga tgagctgacc aagaaccagg tcagcctgac     1200
ctgcctggtc aaaggcttct atcccagcga catcgccgtg gagtgggaga gcaatgggca     1260
gccggagaac aactacaaga ccacgcctcc cgtgctggac tccgacggct ccttcttcct     1320
ctacagcaag ctcaccgtgg acaagagcag gtggcagcag gggaacgtct tctcatgctc     1380
cgtgatgcat gaggctctgc acaaccacta cacgcagaag agcctctccc tgtctccggg     1440
taaatgagtg cgacggccg                                                  1459
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      Artificially synthesized primer sequence
<220> FEATURE:
<221> NAME/KEY: primer_bind
<222> LOCATION: (1)..(27)

<400> SEQUENCE: 8 atgactttg atgacctaaa gatccag                                            27

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:
      Artificially synthesized primer sequence
<220> FEATURE:
<221> NAME/KEY: primer_bind
<222> LOCATION: (1)..(24)

<400> SEQUENCE: 9
cactgtgctc ttaggtttgc cttc                                              24

<210> SEQ ID NO 10
<211> LENGTH: 1514
<212> TYPE: DNA
<213> ORGANISM: Oryctolagus cuniculus
<220> FEATURE:
<221> NAME/KEY: 5'UTR
<222> LOCATION: (1)..(29)
<220> FEATURE:
<221> NAME/KEY: CDS
<222> LOCATION: (30)..(866)
<220> FEATURE:

```
<221> NAME/KEY: 3'UTR
<222> LOCATION: (867)..(1514)

<400> SEQUENCE: 10
tttcactgct tccatctctc gttcttggc atg aat ttg gaa atg gct gtt gac         53
                                Met Asn Leu Glu Met Ala Val Asp
                                  1               5 gac ctc aag gtc aag ccc atg aag gac cag cct gat cag aag tcg aat        101
Asp Leu Lys Val Lys Pro Met Lys Asp Gln Pro Asp Gln Lys Ser Asn
         10                  15                  20 ggg aag aaa cct aaa ggt ctc cgt ttt ctt tct tct ccg tgg tgg tgc        149
Gly Lys Lys Pro Lys Gly Leu Arg Phe Leu Ser Ser Pro Trp Trp Cys
 25                  30                  35                  40 cca gct gct gtg gct ctc gga gtc ctt tgc ctg gga tca ctg atg acc        197
Pro Ala Ala Val Ala Leu Gly Val Leu Cys Leu Gly Ser Leu Met Thr
                 45                  50                  55 att ata atg ctg ggg atg caa tta ttg cag gta tct gac ctc cta aag        245
Ile Ile Met Leu Gly Met Gln Leu Leu Gln Val Ser Asp Leu Leu Lys
             60                  65                  70 caa cag caa gca aac ctc act ctg cag gag aat ata ctg gag gga cag        293
Gln Gln Gln Ala Asn Leu Thr Leu Gln Glu Asn Ile Leu Glu Gly Gln
         75                  80                  85 gtc tta gcc cag cag cag gca gaa gca gct tcc cag gag tca caa agg        341
Val Leu Ala Gln Gln Gln Ala Glu Ala Ala Ser Gln Glu Ser Gln Arg
 90                  95                 100 gaa ctc aaa gaa atg ata gaa act ctt gcc aag agg ctg gat gaa aaa        389
Glu Leu Lys Glu Met Ile Glu Thr Leu Ala Lys Arg Leu Asp Glu Lys
105                 110                 115                 120 tcc aaa aag caa atg gaa ctt aac cat cag tac ctg aat ctc caa gag        437
Ser Lys Lys Gln Met Glu Leu Asn His Gln Tyr Leu Asn Leu Gln Glu
                125                 130                 135 gct ctg aag aga atg gac aac ttt tca ggt cct tgt ccc gaa gac tgg        485
Ala Leu Lys Arg Met Asp Asn Phe Ser Gly Pro Cys Pro Glu Asp Trp
            140                 145                 150 ctc tgg cat gga aaa aac tgt tat ctg ttt tcc tct gga tca ttt aat        533
Leu Trp His Gly Lys Asn Cys Tyr Leu Phe Ser Ser Gly Ser Phe Asn
        155                 160                 165 tgg gaa agt agt caa gag aaa tgc ttg tct ttg gat gcc cag tta ttg        581
Trp Glu Ser Ser Gln Glu Lys Cys Leu Ser Leu Asp Ala Gln Leu Leu
170                 175                 180 aaa att aac agc aca gaa gat ctg ggc ttc atc cag caa gcg act tcc        629
Lys Ile Asn Ser Thr Glu Asp Leu Gly Phe Ile Gln Gln Ala Thr Ser
185                 190                 195                 200 cat tcc agc ttc cca ttc tgg atg gga ttg tct cgg agg aaa ccc gac        677
His Ser Ser Phe Pro Phe Trp Met Gly Leu Ser Arg Arg Lys Pro Asp
                205                 210                 215 tac tca tgg ctc tgg gaa gac ggt tct cct ctg atg ccc cac ttg ttc        725
Tyr Ser Trp Leu Trp Glu Asp Gly Ser Pro Leu Met Pro His Leu Phe
            220                 225                 230 aga ttc cag ggt gct gtt tcc cag agg tac cct tca ggc acc tgt gca        773
Arg Phe Gln Gly Ala Val Ser Gln Arg Tyr Pro Ser Gly Thr Cys Ala
        235                 240                 245 tat ata cag aag gga aat gtt ttt gct gag aac tgc att tta gtt gca        821
Tyr Ile Gln Lys Gly Asn Val Phe Ala Glu Asn Cys Ile Leu Val Ala
250                 255                 260 tac agt atc tgt cag aag aag gca aat ctg ctg aga tca gag tga            866
Tyr Ser Ile Cys Gln Lys Lys Ala Asn Leu Leu Arg Ser Glu
265                 270                 275 atttgaaggc tctggaagaa aagaaagtca atgaactttta ttcaggaatg taagctactc     926
cttgtgacgt aggtgcgaac tctgagagtc ctgagagctg ctcaactcct tatcagaggc      986
```

-continued

```
aaagacgggg gatccagctg cctgatacct tgtagcaaa  agggtttttt tttccccat    1046 cttctatct gtcagtattt atcatctatt gacctaccta catctgtcac ctatctacat    1106
ctattattta tttatctta tctcattatc tatctatctg tccccaacac ccttctctct    1166
tgttcaacca gctgtttcca agcctctgcc agccctcagt ggcacttccc ttttgtattt    1226
aaaatctgac tcctcccaa gctccggagc ccacttcact cagtcttgtc tacctcagtg    1286
cgccttccct gcatgcagac aacacagaga acttgcccaa ctgcaagcag aaagcagaaa    1346
aggagaacta cacatgggaa actgcaacgt gaagaaacag aggaaagatc acactgatca    1406
aactgaaaac aagcgtgcgt tctccacttt aaaatcattg ctcgttggtc tttgtaattg    1466
cagtccatgt ccagactcct gcatgcgcgt gcacacacac acacacac               1514
```

```
<210> SEQ ID NO 11
<211> LENGTH: 278
<212> TYPE: PRT
<213> ORGANISM: Oryctolagus cuniculus

<400> SEQUENCE: 11
```

```
Met Asn Leu Glu Met Ala Val Asp Asp Leu Lys Val Lys Pro Met Lys
 1               5                  10                  15

Asp Gln Pro Asp Gln Lys Ser Asn Gly Lys Lys Pro Lys Gly Leu Arg
            20                  25                  30

Phe Leu Ser Ser Pro Trp Trp Cys Pro Ala Ala Val Ala Leu Gly Val
        35                  40                  45

Leu Cys Leu Gly Ser Leu Met Thr Ile Ile Met Leu Gly Met Gln Leu
    50                  55                  60

Leu Gln Val Ser Asp Leu Leu Lys Gln Gln Ala Asn Leu Thr Leu
 65                  70                  75                  80

Gln Glu Asn Ile Leu Glu Gly Gln Val Leu Ala Gln Gln Ala Glu
                85                  90                  95

Ala Ala Ser Gln Glu Ser Gln Arg Glu Leu Lys Glu Met Ile Glu Thr
            100                 105                 110

Leu Ala Lys Arg Leu Asp Glu Lys Ser Lys Gln Met Glu Leu Asn
        115                 120                 125

His Gln Tyr Leu Asn Leu Gln Glu Ala Leu Lys Arg Met Asp Asn Phe
    130                 135                 140

Ser Gly Pro Cys Pro Glu Asp Trp Leu Trp His Gly Lys Asn Cys Tyr
145                 150                 155                 160

Leu Phe Ser Ser Gly Ser Phe Asn Trp Glu Ser Gln Glu Lys Cys
                165                 170                 175

Leu Ser Leu Asp Ala Gln Leu Leu Lys Ile Asn Ser Thr Glu Asp Leu
            180                 185                 190

Gly Phe Ile Gln Gln Ala Thr Ser His Ser Ser Phe Pro Phe Trp Met
        195                 200                 205

Gly Leu Ser Arg Arg Lys Pro Asp Tyr Ser Trp Leu Trp Glu Asp Gly
    210                 215                 220

Ser Pro Leu Met Pro His Leu Phe Arg Phe Gln Gly Ala Val Ser Gln
225                 230                 235                 240

Arg Tyr Pro Ser Gly Thr Cys Ala Tyr Ile Gln Lys Gly Asn Val Phe
                245                 250                 255

Ala Glu Asn Cys Ile Leu Val Ala Tyr Ser Ile Cys Gln Lys Lys Ala
            260                 265                 270

Asn Leu Leu Arg Ser Glu
        275
```

```
<210> SEQ ID NO 12
<211> LENGTH: 1578
<212> TYPE: DNA
<213> ORGANISM: Sus scrofa
<220> FEATURE:
<221> NAME/KEY: 5'UTR
<222> LOCATION: (1)..(44)
<220> FEATURE:
<221> NAME/KEY: CDS
<222> LOCATION: (45)..(869)
<220> FEATURE:
<221> NAME/KEY: 3'UTR
<222> LOCATION: (870)..(1578)

<400> SEQUENCE: 12
```

| | | | | | | | | | | | |
|---|---|---|---|---|---|---|---|---|---|---|---|
| gtccttggct gctccactcc ctcattcttg gaataaattc agaa atg aca ctt gat | | | | | | | | | | | 56 |
| | | | | | | | | | Met Thr Leu Asp | | |
| | | | | | | | | | 1 | | |

| gac | ctc | aag | agc | aac | agt | atg | aag | gat | caa | cct | gac | gag | aaa | tca | aat | 104 |
|---|---|---|---|---|---|---|---|---|---|---|---|---|---|---|---|---|
| Asp | Leu | Lys | Ser | Asn | Ser | Met | Lys | Asp | Gln | Pro | Asp | Glu | Lys | Ser | Asn | |
| 5 | | | | 10 | | | | 15 | | | | 20 | | | | |

| gga | gat | aaa | gct | gaa | ggt | cct | cgg | agt | ctt | tcc | act | ctg | cgg | tgg | cgc | 152 |
|---|---|---|---|---|---|---|---|---|---|---|---|---|---|---|---|---|
| Gly | Asp | Lys | Ala | Glu | Gly | Pro | Arg | Ser | Leu | Ser | Thr | Leu | Arg | Trp | Arg | |
| | 25 | | | | 30 | | | | 35 | | | | | | | |

| cct | gct | gcc | ctg | att | cta | ggg | tta | ctg | tgc | ctg | gga | tta | ctg | gtg | acc | 200 |
|---|---|---|---|---|---|---|---|---|---|---|---|---|---|---|---|---|
| Pro | Ala | Ala | Leu | Ile | Leu | Gly | Leu | Leu | Cys | Leu | Gly | Leu | Leu | Val | Thr | |
| | 40 | | | | 45 | | | | | 50 | | | | | | |

| gtt | ata | ctg | ctg | ata | ata | cag | ttg | tcc | cag | gtg | tct | gat | ctc | ctg | aag | 248 |
|---|---|---|---|---|---|---|---|---|---|---|---|---|---|---|---|---|
| Val | Ile | Leu | Leu | Ile | Ile | Gln | Leu | Ser | Gln | Val | Ser | Asp | Leu | Leu | Lys | |
| | | 55 | | | | 60 | | | | | 65 | | | | | |

| caa | cag | aaa | gtg | aaa | ctt | act | cac | cag | gaa | gac | atc | ctg | gag | gga | cag | 296 |
|---|---|---|---|---|---|---|---|---|---|---|---|---|---|---|---|---|
| Gln | Gln | Lys | Val | Lys | Leu | Thr | His | Gln | Glu | Asp | Ile | Leu | Glu | Gly | Gln | |
| 70 | | | | 75 | | | | 80 | | | | | | | | |

| gct | tta | gcc | cag | cgc | cag | gcg | gaa | aaa | tct | tcc | cag | gag | tca | caa | agg | 344 |
|---|---|---|---|---|---|---|---|---|---|---|---|---|---|---|---|---|
| Ala | Leu | Ala | Gln | Arg | Gln | Ala | Glu | Lys | Ser | Ser | Gln | Glu | Ser | Gln | Arg | |
| 85 | | | | 90 | | | | 95 | | | | 100 | | | | |

| gaa | ctc | aca | gaa | atg | ata | gaa | act | ctt | gcc | cac | aaa | ttg | gat | gaa | aaa | 392 |
|---|---|---|---|---|---|---|---|---|---|---|---|---|---|---|---|---|
| Glu | Leu | Thr | Glu | Met | Ile | Glu | Thr | Leu | Ala | His | Lys | Leu | Asp | Glu | Lys | |
| | | | 105 | | | | 110 | | | | 115 | | | | | |

| tcc | aag | aaa | ctg | atg | gag | ctt | caa | cag | cag | aac | ttg | aat | ctt | caa | aaa | 440 |
|---|---|---|---|---|---|---|---|---|---|---|---|---|---|---|---|---|
| Ser | Lys | Lys | Leu | Met | Glu | Leu | Gln | Gln | Gln | Asn | Leu | Asn | Leu | Gln | Lys | |
| | | 120 | | | | 125 | | | | 130 | | | | | | |

| gct | ctg | gag | aaa | gcg | gca | aac | ttt | tca | ggt | cct | tgt | ccc | caa | gac | tgg | 488 |
|---|---|---|---|---|---|---|---|---|---|---|---|---|---|---|---|---|
| Ala | Leu | Glu | Lys | Ala | Ala | Asn | Phe | Ser | Gly | Pro | Cys | Pro | Gln | Asp | Trp | |
| | 135 | | | | 140 | | | | 145 | | | | | | | |

| ctc | tgg | cat | gaa | gaa | aac | tgt | tac | aaa | ttt | tcc | tct | ggc | cca | ttt | agt | 536 |
|---|---|---|---|---|---|---|---|---|---|---|---|---|---|---|---|---|
| Leu | Trp | His | Glu | Glu | Asn | Cys | Tyr | Lys | Phe | Ser | Ser | Gly | Pro | Phe | Ser | |
| 150 | | | | 155 | | | | 160 | | | | | | | | |

| tgg | gaa | aaa | agc | cgg | gag | aac | tgc | ttg | tct | ttg | gat | gcc | caa | ctg | ctg | 584 |
|---|---|---|---|---|---|---|---|---|---|---|---|---|---|---|---|---|
| Trp | Glu | Lys | Ser | Arg | Glu | Asn | Cys | Leu | Ser | Leu | Asp | Ala | Gln | Leu | Leu | |
| 165 | | | 170 | | | | 175 | | | | 180 | | | | | |

| aag | att | aat | agc | aca | gac | gat | ctg | gaa | ttc | atc | cag | caa | acc | atc | gcc | 632 |
|---|---|---|---|---|---|---|---|---|---|---|---|---|---|---|---|---|
| Lys | Ile | Asn | Ser | Thr | Asp | Asp | Leu | Glu | Phe | Ile | Gln | Gln | Thr | Ile | Ala | |
| | | | 185 | | | | 190 | | | | 195 | | | | | |

| cat | tcc | agt | ttc | cca | ttc | tgg | atg | ggg | tta | tct | ctg | agg | aaa | ccc | aac | 680 |
|---|---|---|---|---|---|---|---|---|---|---|---|---|---|---|---|---|
| His | Ser | Ser | Phe | Pro | Phe | Trp | Met | Gly | Leu | Ser | Leu | Arg | Lys | Pro | Asn | |
| | | 200 | | | | 205 | | | | 210 | | | | | | |

| aac | tca | tgg | ctc | tgg | gag | gac | ggt | act | cct | ttg | atg | ccc | cac | ttg | ttt | 728 |
|---|---|---|---|---|---|---|---|---|---|---|---|---|---|---|---|---|
| Asn | Ser | Trp | Leu | Trp | Glu | Asp | Gly | Thr | Pro | Leu | Met | Pro | His | Leu | Phe | |
| | 215 | | | | 220 | | | | 225 | | | | | | | |

| aga | ctc | cag | gga | gct | gct | tcc | caa | atg | tat | cct | tca | ggc | acc | tgt | gcg | 776 |
|---|---|---|---|---|---|---|---|---|---|---|---|---|---|---|---|---|
| Arg | Leu | Gln | Gly | Ala | Ala | Ser | Gln | Met | Tyr | Pro | Ser | Gly | Thr | Cys | Ala | |

```
                      230                 235                 240
tat ata cac agg gga att gtt ttt gct gaa aac tgc att tta aat gca       824
Tyr Ile His Arg Gly Ile Val Phe Ala Glu Asn Cys Ile Leu Asn Ala
245                 250                 255                 260 ttc agt ata tgt cag aag agg gcg aat ctc ttg aga gca cag tga           869
Phe Ser Ile Cys Gln Lys Arg Ala Asn Leu Leu Arg Ala Gln
                265                 270 atttgaaagc tttggaagaa aaggagaaga tctttggatt cttttctgga atttaagcta     929
tacttggtca cttaagtgca aaccatgaaa gccctgacaa ctgcctgttg ctctatgagt     989
gcagaactcc ttagcagaga ctgggcctca gctacctgac agcttggtta tcaatagttt    1049
taattctatc cctttctctc tgtgttccct agcgtgtccc aagccccct gcctgccatc     1109 agttaagtcc ctttcctgtt tctattattt ctaagaactt gttgcttaat gcaaggtcgt    1169 aaaattttt ctcctttggt ttctcctagg cattttatag tttctgattt tacatagaaa     1229
cgtataattt attttgggtt aatccgtaag ccatgtttgg atgtaccgaa gtgttttat     1289 tcccccactt ggctactcaa ttgttttcac aatatttgtt gaacagtgca ttatttttt     1349 cactatggct gtctttgcac ttttgtcaac aattattgat acatgcctgg gtctgtttct    1409
gaactctctc ttctgtttcc tttatctatt ctatactctt tgttacagca ccaccatgtt    1469 attttttcc caattttaaa agttttattg aaatatagtt gatttacaat gttgtgagaa     1529
tttcttctgt acaacaaagt gattcaggtc gagcggcccg atatgcttc                1578

<210> SEQ ID NO 13
<211> LENGTH: 274
<212> TYPE: PRT
<213> ORGANISM: Sus scrofa

<400> SEQUENCE: 13

Met Thr Leu Asp Asp Leu Lys Ser Asn Ser Met Lys Asp Gln Pro Asp
  1               5                  10                  15

Glu Lys Ser Asn Gly Asp Lys Ala Glu Gly Pro Arg Ser Leu Ser Thr
             20                  25                  30

Leu Arg Trp Arg Pro Ala Ala Leu Ile Leu Gly Leu Leu Cys Leu Gly
         35                  40                  45

Leu Leu Val Thr Val Ile Leu Ile Ile Gln Leu Ser Gln Val Ser
     50                  55                  60

Asp Leu Leu Lys Gln Gln Lys Val Lys Leu Thr His Gln Glu Asp Ile
 65                  70                  75                  80

Leu Glu Gly Gln Ala Leu Ala Gln Arg Gln Ala Glu Lys Ser Ser Gln
                 85                  90                  95

Glu Ser Gln Arg Glu Leu Thr Glu Met Ile Glu Thr Leu Ala His Lys
            100                 105                 110

Leu Asp Glu Lys Ser Lys Lys Leu Met Glu Leu Gln Gln Asn Leu
        115                 120                 125

Asn Leu Gln Lys Ala Leu Glu Lys Ala Ala Asn Phe Ser Gly Pro Cys
    130                 135                 140

Pro Gln Asp Trp Leu Trp His Glu Glu Asn Cys Tyr Lys Phe Ser Ser
145                 150                 155                 160

Gly Pro Phe Ser Trp Glu Lys Ser Arg Glu Asn Cys Leu Ser Leu Asp
                165                 170                 175

Ala Gln Leu Leu Lys Ile Asn Ser Thr Asp Asp Leu Glu Phe Ile Gln
            180                 185                 190

Gln Thr Ile Ala His Ser Ser Phe Pro Phe Trp Met Gly Leu Ser Leu
        195                 200                 205
```

```
Arg Lys Pro Asn Asn Ser Trp Leu Trp Glu Asp Gly Thr Pro Leu Met
    210             215                 220
Pro His Leu Phe Arg Leu Gln Gly Ala Ala Ser Gln Met Tyr Pro Ser
225             230                 235                 240
Gly Thr Cys Ala Tyr Ile His Arg Gly Ile Val Phe Ala Glu Asn Cys
                245                 250                 255
Ile Leu Asn Ala Phe Ser Ile Cys Gln Lys Arg Ala Asn Leu Leu Arg
            260                 265                 270
Ala Gln

<210> SEQ ID NO 14
<211> LENGTH: 3750
<212> TYPE: DNA
<213> ORGANISM: Rattus norvegicus
<220> FEATURE:
<221> NAME/KEY: 5'UTR
<222> LOCATION: (1)..(91)
<220> FEATURE:
<221> NAME/KEY: CDS
<222> LOCATION: (92)..(1186)
<220> FEATURE:
<221> NAME/KEY: 3'UTR
<222> LOCATION: (1187)..(3750)

<400> SEQUENCE: 14
atttaaactg catcagaagc tcgagcactg gcagttggct gactgaggtc ctctactgtt     60
tcagtttccc attcttggca tgaatttgga a atg gct ttt gat gac aag atg      112
                                  Met Ala Phe Asp Asp Lys Met
                                   1               5 aag cct gtg aat ggc cag cct gat cag aag tca tgt ggc aag aag cct    160
Lys Pro Val Asn Gly Gln Pro Asp Gln Lys Ser Cys Gly Lys Lys Pro
         10                  15                  20 aaa ggg ctg cat ttg ctt tct tcc aca tgg tgg tgc cct gct gct gtg    208
Lys Gly Leu His Leu Leu Ser Ser Thr Trp Trp Cys Pro Ala Ala Val
 25                  30                  35 act ctg gcc atc ctt tgc cta gtg tta tca gtg acc ctt att gta cag    256
Thr Leu Ala Ile Leu Cys Leu Val Leu Ser Val Thr Leu Ile Val Gln
 40                  45                  50                  55 cag aca cag tta ctc cag gta tct gac ctc cta aag caa tac caa gca    304
Gln Thr Gln Leu Leu Gln Val Ser Asp Leu Leu Lys Gln Tyr Gln Ala
             60                  65                  70 aac ctt act cag cag gat cat atc ctg gag ggg cag atg tca gcc cag    352
Asn Leu Thr Gln Gln Asp His Ile Leu Glu Gly Gln Met Ser Ala Gln
         75                  80                  85 aag aaa gca gaa aat gct tca caa gaa tca aag agg gaa ctg aag gaa    400
Lys Lys Ala Glu Asn Ala Ser Gln Glu Ser Lys Arg Glu Leu Lys Glu
 90                  95                 100 cag ata gac acc ctc acc tgg aag cta aac gag aaa tcc aaa gag cag    448
Gln Ile Asp Thr Leu Thr Trp Lys Leu Asn Glu Lys Ser Lys Glu Gln
            105                 110                 115 gag aag ctt ctg cag cag aat cag aac ctc caa gaa gcc ctg cag aga    496
Glu Lys Leu Leu Gln Gln Asn Gln Asn Leu Gln Glu Ala Leu Gln Arg
120                 125                 130                 135 gct gtg aac gct tca gag gag tcc aag tgg gaa ctg aag gaa caa ata    544
Ala Val Asn Ala Ser Glu Glu Ser Lys Trp Glu Leu Lys Glu Gln Ile
            140                 145                 150 gac att ctc aac tgg aag ctg aat ggg ata tcc aaa gag cag aag gag    592
Asp Ile Leu Asn Trp Lys Leu Asn Gly Ile Ser Lys Glu Gln Lys Glu
        155                 160                 165 ctt ctg cag cag aat cag aac ctc caa gaa gcc ctg cag aaa gct gag    640
Leu Leu Gln Gln Asn Gln Asn Leu Gln Glu Ala Leu Gln Lys Ala Glu
```

-continued

```
                   170                 175                 180
aaa tat tca gag gag tcc cag aga gaa ctg aag gaa cag ata gac acc        688
Lys Tyr Ser Glu Glu Ser Gln Arg Glu Leu Lys Glu Gln Ile Asp Thr
185                 190                 195 ctc agc tgg aag cta aac gag aaa tcc aaa gag cag gag gag ctt ctg        736
Leu Ser Trp Lys Leu Asn Glu Lys Ser Lys Glu Gln Glu Glu Leu Leu
200                 205                 210                 215 cag cag aat cag aat ctt caa gaa gcc ctg cag aga gct gca aac tct        784
Gln Gln Asn Gln Asn Leu Gln Glu Ala Leu Gln Arg Ala Ala Asn Ser
                    220                 225                 230 tca ggt cct tgt cca caa gac tgg atc tgg cat aaa gaa aac tgt tac        832
Ser Gly Pro Cys Pro Gln Asp Trp Ile Trp His Lys Glu Asn Cys Tyr
                235                 240                 245 ctc ttc cat ggg ccc ttt aac tgg gaa aaa agt cgg gag aat tgc cta        880
Leu Phe His Gly Pro Phe Asn Trp Glu Lys Ser Arg Glu Asn Cys Leu
            250                 255                 260 tct tta gat gcc cag tta cta caa att agt acc aca gat gat ctg aac        928
Ser Leu Asp Ala Gln Leu Leu Gln Ile Ser Thr Thr Asp Asp Leu Asn
265                 270                 275 ttc gtc tta caa gca act tcc cat tcc acc tcc cca ttt tgg atg gga        976
Phe Val Leu Gln Ala Thr Ser His Ser Thr Ser Pro Phe Trp Met Gly
280                 285                 290                 295 tta cat cgg aaa aat ccc aac cac cca tgg cta tgg gag aac ggc tct       1024
Leu His Arg Lys Asn Pro Asn His Pro Trp Leu Trp Glu Asn Gly Ser
                    300                 305                 310 cct ttg agt ttt caa ttc ttt agg acc agg ggc gtt tct tta cag atg       1072
Pro Leu Ser Phe Gln Phe Phe Arg Thr Arg Gly Val Ser Leu Gln Met
                315                 320                 325 tac tca tca ggc acc tgt gca tat att caa gga gga gtt gtg ttt gct       1120
Tyr Ser Ser Gly Thr Cys Ala Tyr Ile Gln Gly Gly Val Val Phe Ala
            330                 335                 340 gaa aac tgc att tta act gca ttc agc ata tgt cag aag aag gca aat       1168
Glu Asn Cys Ile Leu Thr Ala Phe Ser Ile Cys Gln Lys Lys Ala Asn
345                 350                 355 tta ttg cta act cag tga aactaaggat tctggagaag aacaggagaa              1216
Leu Leu Leu Thr Gln
360 gacctttaac tgttgttttg aaatttaagc tatcctttct tgggtgtaaa acatgtggcc     1276 ttgacagctg tcagttactt tctaactgca gttcacctca acagagacaa agaccagaag     1336 caaaaacccg ggggtccagc tgatggcatc tttgtatcaa agttgtgaa ttcaattgtt      1396 tatccatgta cactggcccc gcccctccca agactcccaa ccaacctgca atccttttt      1456 tctttcttgt tttaaactat gcctcctgtc tgacctgggg gatgctttct gctcaatttc    1516 ctctacctca ggtatgcctt ctgttgctgc atgaaagaca gaatgtagaa aaccttcttc    1576 aagtgcaggc agagagctca agttaaaaaa catgcctaag aaatagcatg caaagaaaca    1636 gaactggaaa agctacactg tacgcaggag ctcatggtct ctaaaaagct atggcttgat    1696 cttcacgact tgggtccatc tccagactgc accatttaca catttatgtt ttttattttt    1756 attttattg tgtgtttatg gatagttggc ctatatgtat ctctgtgtac cacatgagtg     1816 tctccattca gaagagggca tcagattctc tgaaactgga actgcagatg gctgtaagct    1876 actacataga tgtaaagaat tgaattcatg tcctctgaaa gacagtcag tactcttaac     1936 catgaactat ttctccaggt cccgtgatca tttcttgtat cagctatttc ttcacatttg    1996 ctctaccaaa gaacagagct taaaacagta ttttataaag ccatagaata tggccccaaa    2056 acaaaactag aattttctcc ttaaattgca tactttgtag acagtctctc cttgaccctg    2116
```

```
ccatgccatg ctatgactta gaaacataca tgaccaaaat ggatgaaact cagttgaaga    2176
acaagttctt agaatcacct gagctgggta taaaaatatt gttctatggg aacagatgga    2236
tttagaaata tctattatca gggcctccac catccccaca agtcacagac tcttccattt    2296
caaaggaagc tttccattat gctagaggta atatagcata tatgtcatgt atatgagtgt    2356
gtatttgtgt gtgtgagtgt gtgtgttcat atgctagata cgtccttgag aagatgagac    2416
attggcagct ttgtgtgtaa tgaatttgca ataatccaaa tttgtaagta gtttccatgg    2476
ttccttatag tgatgacatc accacagcca agatgatgag catacctgtt gtttctgccc    2536 cttttccaatg cttcctccct agaacaaaca ccaatctgtt gtcagttgtc atttcataga   2596
gtttataatc ttgtttttaa gagagaatct cattatatag ttctgactgc cctgggactc    2656
actacacaga ccagcctggc ctccaccttc cagagttcct cctgcctttg actcacaagt    2716
gctaacactg aaggagtgca ccgccatgta tggctcatgc agtttatgtg aatggaatag    2776
tataacacat ccagattttc tcagttcagt ttcttccact tggtgctatt attttggtat    2836
tcatacatct ctgcctcagt gtttgtatca gttcttcaat ttttttaaaa tgttgatcat    2896
tcccctggtg ggtacatatt gtcattttta tctgtgtatt tgttgatgtc atttgggttg    2956
tttttgtttg gggtcaccta caaataaagc tgctatgaat gcccatggac gattctggtt    3016
tctcatgtaa gcacctctga gtgtgacact tgggtcattc agtgtgtgaa tatatggttg    3076
gccatgttaa ccattgcttt ttgaaatttc caattttttt taaaattagt cgactttaca    3136
tctcaactcc aatttccttc cctcctctcc tctcaatctt cacccacctc cctctcctac    3196
ccccatccac tcttcccttt ctcttcagaa aagaggaggc ttcccacaga tgtcaaccag    3256
ccttagcgta tcaagttgca gtaagaatag gtttatcatc ttctatgaaa gccttaatttt  3316 ttagacttat cactgtatat gcagtatttt gtttgcatgt atgtattggt accacatata    3376
tgcctaatac cagaggaagt cagaagaggg catggtatct tctgagactg gaattacaga    3436 cattttttgag ccatcctaca gactctggaa attgaaccca ggatttctgg aaagttaggc   3496
agtgctctta acccctgaac catctcttca ggccctatag caatctttat tgatatgtaa    3556
ctgtgtataa ttgcactttt agtttgaagt tcttaaatgg caaatagtct tgaatttatt    3616
ttcatgttat catttactgt ctgtacattt tctgtaatga aataactaag catatctttt    3676
gagaatttta ttttcttaca ttttaaatct gaaggattta catacatact ggagaataaa    3736
aacagcctaa tgtg                                                      3750
```

<210> SEQ ID NO 15
<211> LENGTH: 364
<212> TYPE: PRT
<213> ORGANISM: Rattus norvegicus

<400> SEQUENCE: 15

```
Met Ala Phe Asp Asp Lys Met Lys Pro Val Asn Gly Gln Pro Asp Gln
 1               5                  10                  15

Lys Ser Cys Gly Lys Lys Pro Lys Gly Leu His Leu Leu Ser Ser Thr
             20                  25                  30

Trp Trp Cys Pro Ala Ala Val Thr Leu Ala Ile Leu Cys Leu Val Leu
         35                  40                  45

Ser Val Thr Leu Ile Val Gln Gln Thr Gln Leu Leu Gln Val Ser Asp
     50                  55                  60

Leu Leu Lys Gln Tyr Gln Ala Asn Leu Thr Gln Gln Asp His Ile Leu
 65                  70                  75                  80

Glu Gly Gln Met Ser Ala Gln Lys Lys Ala Glu Asn Ala Ser Gln Glu
```

-continued

```
                85                    90                    95
Ser Lys Arg Glu Leu Lys Glu Gln Ile Asp Thr Leu Thr Trp Lys Leu
            100                   105                   110

Asn Glu Lys Ser Lys Glu Gln Glu Lys Leu Leu Gln Gln Asn Gln Asn
            115                   120                   125

Leu Gln Glu Ala Leu Gln Arg Ala Val Asn Ala Ser Glu Glu Ser Lys
    130                   135                   140

Trp Glu Leu Lys Glu Gln Ile Asp Ile Leu Asn Trp Lys Leu Asn Gly
145                   150                   155                   160

Ile Ser Lys Glu Gln Lys Glu Leu Leu Gln Gln Asn Gln Asn Leu Gln
            165                   170                   175

Glu Ala Leu Gln Lys Ala Glu Lys Tyr Ser Glu Glu Ser Gln Arg Glu
            180                   185                   190

Leu Lys Glu Gln Ile Asp Thr Leu Ser Trp Lys Leu Asn Glu Lys Ser
            195                   200                   205

Lys Glu Gln Glu Glu Leu Leu Gln Gln Asn Gln Asn Leu Gln Glu Ala
            210                   215                   220

Leu Gln Arg Ala Ala Asn Ser Ser Gly Pro Cys Pro Gln Asp Trp Ile
225                   230                   235                   240

Trp His Lys Glu Asn Cys Tyr Leu Phe His Gly Pro Phe Asn Trp Glu
            245                   250                   255

Lys Ser Arg Glu Asn Cys Leu Ser Leu Asp Ala Gln Leu Leu Gln Ile
            260                   265                   270

Ser Thr Thr Asp Asp Leu Asn Phe Val Leu Gln Ala Thr Ser His Ser
            275                   280                   285

Thr Ser Pro Phe Trp Met Gly Leu His Arg Lys Asn Pro Asn His Pro
    290                   295                   300

Trp Leu Trp Glu Asn Gly Ser Pro Leu Ser Phe Gln Phe Arg Thr
305                   310                   315                   320

Arg Gly Val Ser Leu Gln Met Tyr Ser Ser Gly Thr Cys Ala Tyr Ile
            325                   330                   335

Gln Gly Gly Val Val Phe Ala Glu Asn Cys Ile Leu Thr Ala Phe Ser
            340                   345                   350

Ile Cys Gln Lys Lys Ala Asn Leu Leu Leu Thr Gln
            355                   360
```